United States Patent [19]
Breuer et al.

[11] Patent Number: 4,801,705
[45] Date of Patent: Jan. 31, 1989

[54] 2-OXO-1-(((SUBSTITUTED SULFONYL)AMINO)-CARBONYL)AZETIDINES

[75] Inventors: Hermann Breuer, Schoenhofen; Jakob-Matthias Drossard, Regensburg; Peter H. Ermann, Donaustauf; Henner Straub, Regensburg; Uwe D. Treuner, Etterzhausen, all of Fed. Rep. of Germany

[73] Assignee: E. R. Squibb & Sons, Inc., Princeton, N.J.

[21] Appl. No.: 877,599

[22] Filed: Jun. 23, 1986

[51] Int. Cl.$^4$ .................. C07D 403/12; C07D 417/14; A61K 31/495; A61K 31/415
[52] U.S. Cl. ..................................... 540/357; 540/360; 540/363; 540/364
[58] Field of Search ................ 540/357, 360, 363, 364

[56] References Cited

U.S. PATENT DOCUMENTS 4,587,047  5/1986  Breuer et al. .
4,670,553  6/1987  Breuer et al. ................... 540/363
4,743,685  5/1988  Breuer et al. ................... 540/363

FOREIGN PATENT DOCUMENTS 85291  8/1983  European Pat. Off. .......... 540/360

OTHER PUBLICATIONS

Breuer, Chem Abs 98, 107072a (1982).
Abstract No. 646 from 1987 ICAAC meeting, "Antimicrobial Activities of 1-Carbacephem Compounds and Their Structure-Relationships", Mochida et al.
"The Proceedings of the Third International Symposium", pp. 32-51, arranged by the Fine Chemicals and Medicinals Group of the Industrial Division of The Royal Society of Chemistry, Cambridge, England, 2nd-4th, Jul., 1984.

Primary Examiner—Mark L. Berch
Attorney, Agent, or Firm—Lawrence S. Levinson; Donald J. Barrack

[57] ABSTRACT

Antibacterial activity is exhibited by β-lactams having a 3-acylamino substituent and having in the 1-position an activating group of the formula

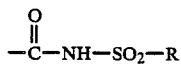

wherein R is

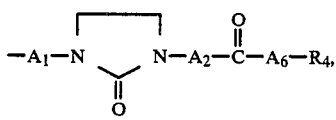

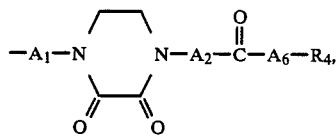

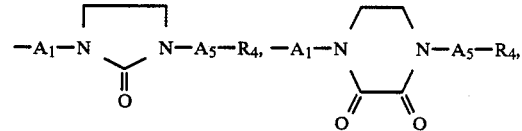

15 Claims, No Drawings

2-OXO-1-(((SUBSTITUTED SULFONYL)AMINO)-CARBONYL)AZETIDINES

BRIEF DESCRIPTION OF THE INVENTION

Compounds having the formula

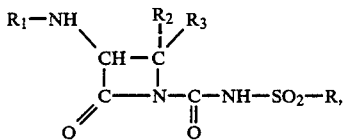  I and pharmaceutically acceptable salts thereof, exhibit antibacterial activity. In formula I, and throughout the specification, the symbols are as defined below.

R is

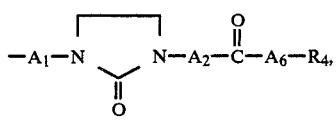

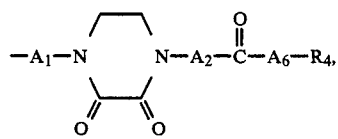

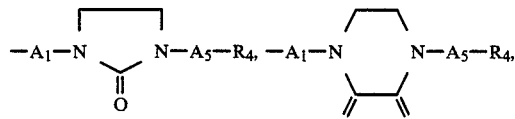

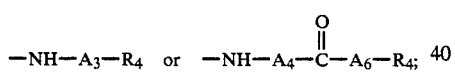

$R_1$ is an acyl group derived from a carboxylic acid;
$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

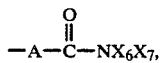

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

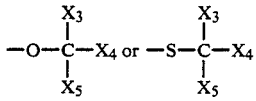

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

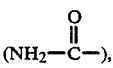

(substituted amino)carbonyl, or cyano (—C≡N)], or

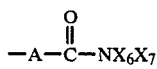

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ is when taken together with the nitrogen atom to which they are attached form a 4, 5, 6 or 7-membered heterocycle];

$A_1$ is a single bond, $$-NH-\overset{O}{\overset{\|}{C}}-,\ -NH-\ or\ -NH-NH-\overset{O}{\overset{\|}{C}}-;$$

$A_2$ is a single bond, $$-NH-,\ -CH_2-CH_2-NH-,\ or\ -\overset{O}{\overset{\|}{C}}-NH-NH-;$$

$A_3$ is —$(CH_2)_p$— wherein p is 0, 1, 2, 3 or 4,

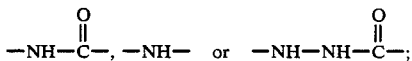

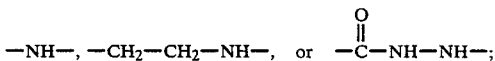

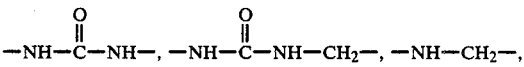

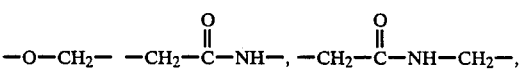

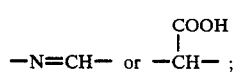

$A_4$ is —NH—, —$(CH_2)_p$—, —$(CH_2)_y$—NH—,

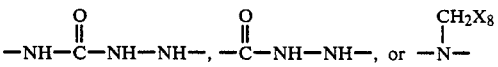

wherein $X_8$ is hydrogen, carboxyl or carbamoyl and p is 0, 1, 2, 3 or 4, and y is 2, 3, or 4;

$A_5$ is

—$(CH_2)_p$—, —NH—$CH_2$—, —N=CH—, or

-continued

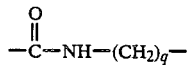

wherein p is 0, 1, 2, 3 or 4, and q is 0 or 1;
A₆ is

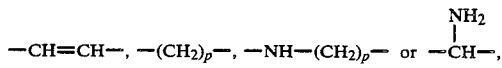

wherein p is 0, 1, 2, 3 or 4; and
R₄ is

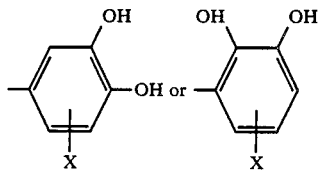

wherein X is hydrogen, halogen, carboxyl, sulfo (—SO₃H), carbamoyl, aminosulfonyl, cyano, alkyl, alkanoyl or alkoxycarbonyl.

The above symbols (e.g., $A_1$, $A_2$, $A_3$, $A_4$, $A_5$ and $A_6$) are used to represent groups of multiple atoms. These groups are inserted in the structural formulas shown herein in the order in which they are presented (i.e., from left to right). For example, if R is

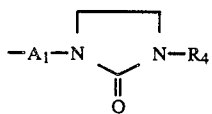

and $A_1$ is

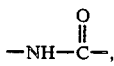

the R group would be

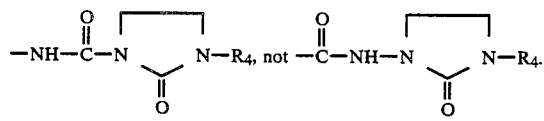

DETAILED DESCRIPTION OF THE INVENTION

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino (—NH₂), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

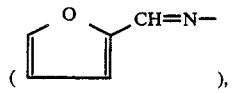

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino[ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX₈X₉ wherein X₈ is hydrogen, alkyl, phenyl, substituted phenyl, phenylalkyl or (substituted phenyl)alkyl, and X₉ is alkyl, phenyl, substituted phenyl, phenylalkyl (substituted phenyl)alkyl, hydroxy, cyano, alkoxy, phenylalkoxy, or amino (—NH₂).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199; issued Oct. 23, 1977, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

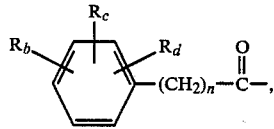

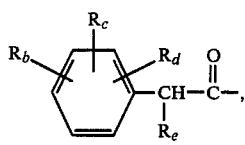

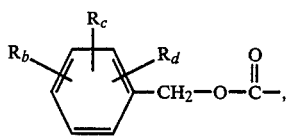

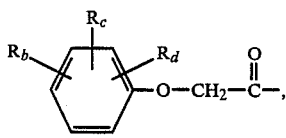

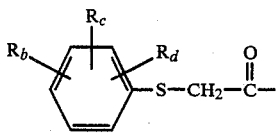

or

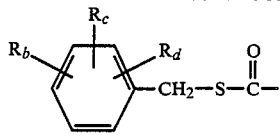

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

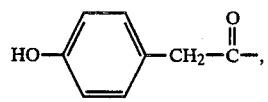

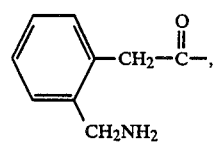

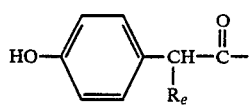

($R_e$ is preferably a carboxyl salt or sulfo salt) and

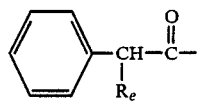

($R_e$ is preferably a carboxyl salt or sulfo salt).

(c) Heteroaromatic groups having the formula

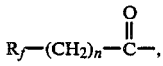

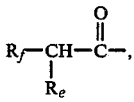

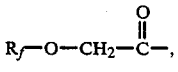

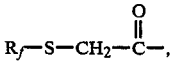

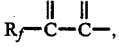

wherein n is 0, 1, 2, or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

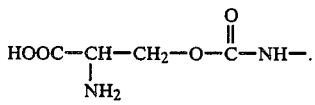

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

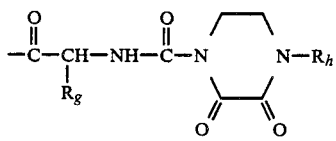

wherein $R_g$ is an aromatic group (including carbocyclic aromatics such as those of the formula

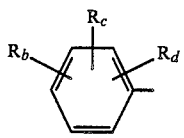

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

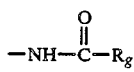

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oximino)arylacetyl groups having the formula

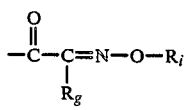

wherein $R_g$ is as defined above and $R_i$ is hydrogen, alkyl, cycloalkyl,

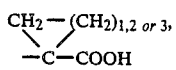

2-pyrrazolylmethyl, (2-oxo-3-pyrrolidinyl)methyl, alkylaminocarbonyl, arylaminocarbonyl (i.e.,

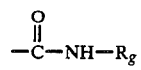

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

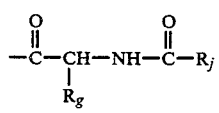

wherein $R_g$ is as defined above and $R_j$ is

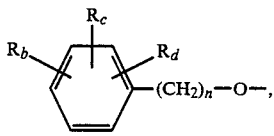

amino, alkylamino, (cyanoalkyl)amino, amido, alkylamido, (cyanoalkyl)amido,

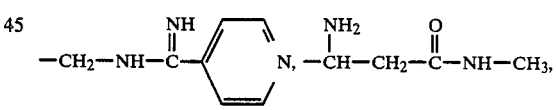

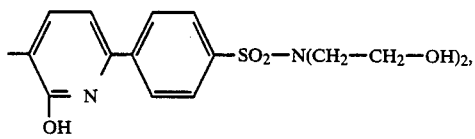

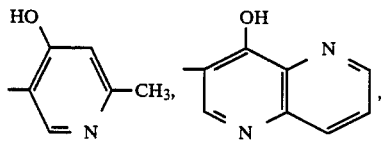

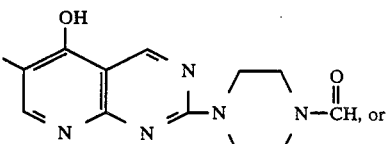

-continued

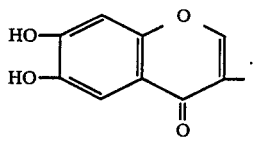

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl-]amino]arylacetyl groups having the formula

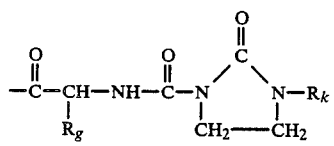

wherein $R_g$ is as defined above and $R_k$ is hydrogen, alkylsulfonyl, arylmethyleneamino (i.e.,

wherein $R_g$ is as defined above), (wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine, choline and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C). Also included within the scope of this invention are racemic mixtures which contain the abovedescribed β-lactams.

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

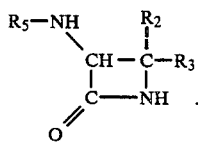
II

In formula II, and throughout the specification, the symbol "$R_5$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula $$O=C=N-SO_2-Y,$$
III wherein Y is a leaving group such as chlorine, yields the corresponding compound having the formula

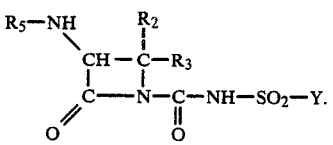
IV

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group "R" can be accomplished using the appropriate nucleophile having the formula

RH,
V optionally in the presence of a base (e.g., triethylamine), and yields the corresponding compound having the formula

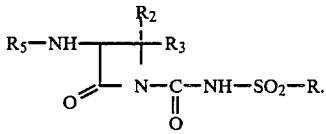

VI

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI. Still another procedure for displacing the leaving group comprises the reaction of a compound of formula IV with a trimethylsilyl derivative of a compound of formula V (i.e., R—Si(CH$_3$)$_3$), optionally in the presence of a base.

Protected forms of a compound of formula V, and of all reactants described herein which contain a catechol moiety, include those compounds wherein the hydroxyl groups are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Deprotection of a compound of formula VI using conventional techniques yields the corresponding key intermediate having the formula

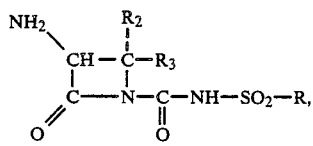

VII or a salt thereof. The particular deprotection reaction used will, of course, depend on the protecting group ("R$_5$") present. If, for example, R$_5$ is a t-butoxycarbonyl protecting group, deprotection can be accomplished by treatment of a compound of formula VI with acid (e.g., formic acid or trifluoroacetic acid). If, for example, R$_5$ is a benzyloxycarbonyl protecting group, deprotection can be accomplished by catalytic hydrogenation of a compound of formula VI. Alternatively, the R$_5$ protecting group can be removed simultaneously with the other catechol protecting groups immediately following the above-described displacement reaction.

Well known acylation techniques can be used to convert an intermediate of formula VII to a corresponding product of formula I. Exemplary techniques include reaction of a compound of formula VII with a carboxylic acid (R$_1$-OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group (R$_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

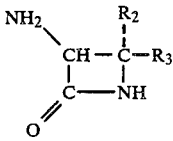

VIII to yield an intermediate having the formula

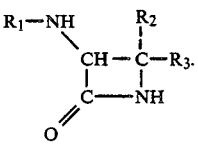

IX

A

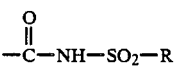

activating group can be introduced in the 1-position of a compound of formula IX (using the procedures described above) to obtain the corresponding product of formula I. In those instances wherein the acyl side-chain "R$_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

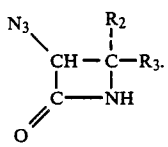

X

A

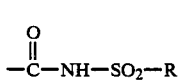

activating group can be introduced in the 1-position of a compound of formula X (using the procedures described above) to obtain the corresponding compound having the formula

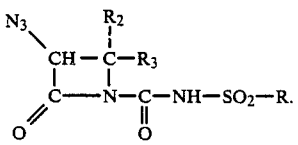

XI

Reduction of an intermediate of formula XI yields the corresponding intermediate having the formula

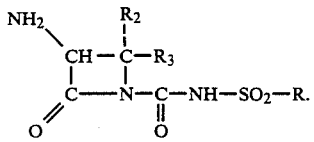    VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

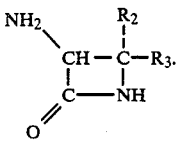    VIII

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

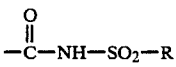

activating group in the 1-position) to yield the products of formula I.

Still another synthesis for preparing the compounds of formula I wherein $R_2$ and $R_3$ are each hydrogen utilizes a 6-acylaminopenicillanic acid having the formula

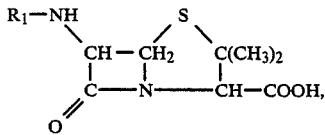    XII or a salt thereof, as the starting material. By adapting procedures described in the literature, 3-acylamino-2-azetidinone can be obtained from the corresponding 6-acylaminopenicillanic acid of formula XII: see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

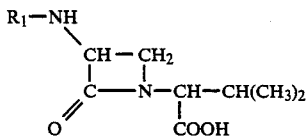    XIII by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

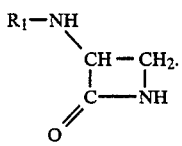    XIV

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A $$-\overset{O}{\underset{\|}{C}}-NH-SO_2-R$$

activating group can be introduced in the 1-position of a compound of formula XIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula

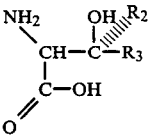    XV

The amino group is first protected (with a protecting group "$R_5$", e.g., t-butoxycarbonyl). The carboxyl group of the protected amino acid is then reacted with an amine having the formula

Z—O—NH$_2$,    XVI wherein Z is alkyl, benzyl or triphenylmethyl, in the presence of a carbodiimide to yield a compound having the formula

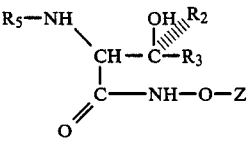    XVII

The hydroxyl group of a compound of formula XVII is converted to a leaving group ("OL) with a reagent, such as methanesulfonyl chloride or pyridine-SO₃ complex.

The fully protected compound having the formula

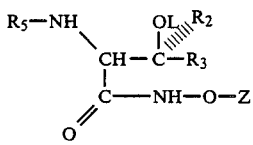                    XVIII is cyclized by treatment with base, e.g., potassium carbonate. The reaction is preferably carried out in an organic solvent or an organic solvent/water mixture under reflux conditions, and yields a compound having the formula

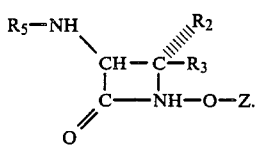                    XIX

Alternatively, cyclization of a compound of formula XVII can be accomplished without first converting the hydroxyl group to a leaving group. Treatment of a compound of formula XVII with triphenylphosphine and diethylazodicarboxylate or with triphenylphosphine, carbon tetrachloride and triethylamine yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the stereochemistry at the carbon atom bearing the R₂ and R₃ substituents when R₂ and R₃ are not the same.

Removal of the protecting group from the 1-position of an azetidinone of formula XIX can be accomplished via sodium reduction when Z is alkyl, and yields an intermediate having the formula

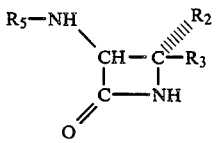                    II (at least one of R₂ and R₃ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound.

A

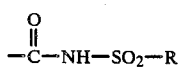

activating group can be introduced in the 1-position of a compound of formula II using the procedures described above, and the resulting compound can be protected and acylated.

The nucleophiles of formula V wherein R is

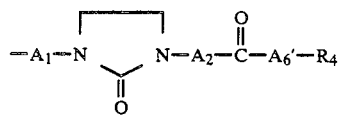

and A₁ and A₂ are each a single bond can be prepared by reacting a silylated derivative of 2-imidazolidinone

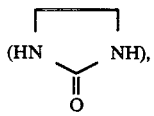

or the anion of 2-imidazolidinone formed with a strong non-nucleophilic base, with an activated, suitably protected derivative of an acid having the formula

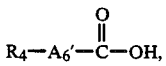                    XX to obtain, upon deprotection, the corresponding compound having the formula

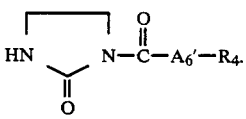                    XXI

As used throughout the specification, the symbol A₆' is —CH=CH—, —(CH₂)$_p$—, or

wherein p is 0, 1, 2, 3 or 4 (i.e., all A₆ groups other than —NH(CH₂)$_p$—). The reaction can be run in an inert organic solvent such as dimethylformamide, acetonitrile, dichloromethane, or tetrahydrofuran. The acid of formula XX can be activated with dicyclohexylcarbodiimide, or a combination of dicyclohexylcarbodiimide and hydroxybenzotriazole. An activated and suitably protected derivative of a compound of formula XX can also be the corresponding acid chloride (prepared with reagents such as phosphorus pentachloride, thionyl chloride, oxalyl chloride or triphenylphosphine/carbon tetrachloride) or a mixed anhydride (prepared with such reagents as diphenylphosphoryl chloride, pivaloyl chloride, or isobutyl chloroformate).

Protected forms of compounds of formula XX include those compounds wherein the hydroxyl groups are protected, if X is carboxyl, that group is protected, and if A₆' is

the amino group is protected. Exemplary protecting groups are silyl, acetyl, benzyl, and methyl for the hydroxyl groups; benzyl, t-butyl and diphenylmethyl for the carboxyl group; and t-butoxycarbonyl and benzyloxycarbonyl for the amino group. Methodology used for deprotecting a compound of formula XXI will depend on the protecting group used: hydrolysis removes silyl and acetyl groups; hydrogenolysis removes benzyl and benzyloxycarbonyl groups; aqueous hydrobromic acid at elevated temperature or boron tribromide removes methyl groups; and trifluoroacetic acid removes t-butoxycarbonyl groups.

The compounds of formula XX wherein $A_6'$ is —$(CH_2)_p$— (and p is 0 or 1) or —CH=CH— are commercially available.

The compounds of formula XX wherein $A_6'$ is $$\overset{NH_2}{\underset{}{-CH-}}$$

can be prepared as described in the literature; see, for example, Physiol. Chemie, 98: 226 (1917) and German Offenlegungschrift No. 2,151,521.

The compounds of formula XX wherein $A_6'$ is —$(CH_2)_p$— and p is 2, 3 or 4 can be formed by conjugation of a compound having the formula $$R_4-\overset{O}{\overset{\|}{C}}H$$

(suitably protected) with a Wittig reagent having the formula $$(\text{C}_6\text{H}_5)_3\text{P}=\text{CH}-(\text{CH}_2)_{p-1}\overset{O}{\overset{\|}{\text{C}}}-\text{OH} \qquad \text{XXII}$$

(suitably protected at the carboxyl group), subsequent hydrogenation of the resulting exocyclic double bond, and deprotection to yield $$R_4-(CH_2)_p-\overset{O}{\overset{\|}{C}}-OH, \qquad \text{XXIII}$$

wherein p is 2, 3 or 4.

The nucleophile of formula V wherein R is $$-A_1-N \underset{\underset{O}{\|}}{\overset{\frown}{\phantom{X}}} N-A_2-\overset{O}{\overset{\|}{C}}-A_6'-R_4,$$

$A_1$ is a single bond and $A_2$ is —NH— can be prepared by reacting an activated and optionally protected derivative of a compound of formula XX with 1-amino-2-imidazolidinone $$(HN \underset{\underset{O}{\|}}{\overset{\frown}{\phantom{X}}} N-NH_2)$$

to yield upon deprotection $$HN \underset{\underset{O}{\|}}{\overset{\frown}{\phantom{X}}} N-NH-\overset{O}{\overset{\|}{C}}-A_6'-R_4. \qquad \text{XXIV}$$

The reaction can be run in an inert solvent such as dimethylformamide. The acid of formula XX can be activated with a mixture of dicyclohexylcarbodiimide, N-hydroxybenzotriazole and 4-dimethylaminopyridine.

The nucleophiles of formula V wherein R is $$-A_1-N \underset{\underset{O}{\|}}{\overset{\frown}{\phantom{X}}} N-A_2-\overset{O}{\overset{\|}{C}}-A_6'-R_4,$$

$A_1$ is a single bond and $A_2$ is —$CH_2$—$CH_2$—NH— can be prepared by reacting an activated and optionally protected derivative of a compound of formula XX with 1-(2-aminoethyl)-2-imidazolidinone $$(HN \underset{\underset{O}{\|}}{\overset{\frown}{\phantom{X}}} N-CH_2CH_2NH_2)$$

to yield upon deprotection $$HN \underset{\underset{O}{\|}}{\overset{\frown}{\phantom{X}}} N-CH_2-CH_2-NH-\overset{O}{\overset{\|}{C}}-A_6'-R_4. \qquad \text{XXV}$$

The nucleophiles of formula V wherein R is $$-A_1-N \underset{\underset{O}{\|}}{\overset{\frown}{\phantom{X}}} N-A_2-\overset{O}{\overset{\|}{C}}-A_6'-R_4,$$

$A_1$ is a single bond and $A_2$ is $$-\overset{O}{\overset{\|}{C}}-NH-NH-$$

can be prepared by reacting $$\text{C}_6\text{H}_5-CH_2-O-\overset{O}{\overset{\|}{C}}-NH-NH-\overset{O}{\overset{\|}{C}}-Cl \qquad \text{XXVI}$$

with a silylated form of 2-imidazolidinone, the anion of 2-imidazolidinone formed with a strong non-nucleophilic base, or with 2-imidazolidinone in the presence of an organic base to yield

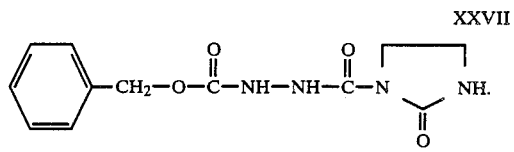

XXVII

Catalytic hydrogenation of the compound of formula XXVII yields the compound having the formula

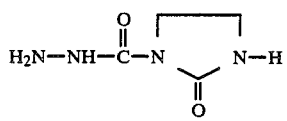

XXVIII which can be coupled with an activated and optionally protected derivative of a compound of formula XX to yield, upon deprotection,

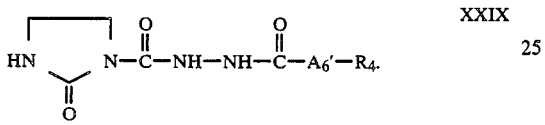

XXIX

Alternatively, the compound of formula XXVIII can be prepared by first reacting 1-chlorocarbonyl-2-imidazolidinone with t-butoxycarbonyl protected hydrazine to yield

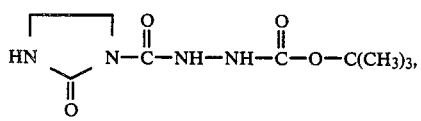

XXX and deprotecting the compound of formula XXX.

The nucleophiles of formula V wherein R is

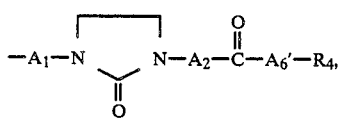

$A_1$ is

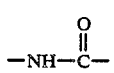

and $A_2$ is a single bond can be prepared by reacting a compound having the formula

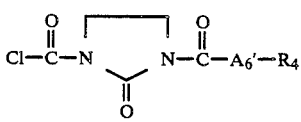

XXXI (suitably protected) with hexamethyldisilazane to yield

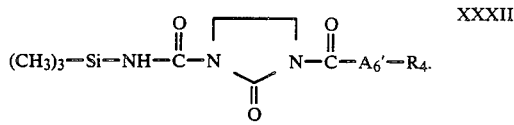

XXXII

The compounds of formula XXXI (suitably protected) can be prepared by reacting a silylated form of a compound of formula XXI (optionally protected) with phosgene.

A non-silylated derivative of a compound of formula XXXII can be prepared by hydrolytic cleavage of the silyl group in a compound of formula XXXII or by reacting a protected form of a compound of formula XXI with chlorosulfonylisocyanate followed by hydrolysis of the resulting intermediate and cleavage of the protecting groups to yield

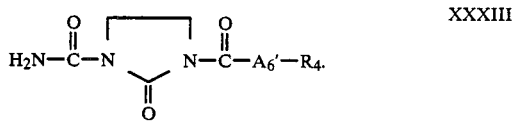

XXXIII

The nucleophiles of formula V wherein R is

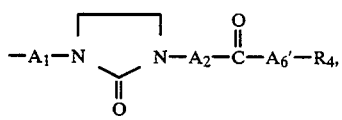

$A_1$ is

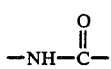

and $A_2$ is —NH— can be prepared by reacting a silylated form of the compound

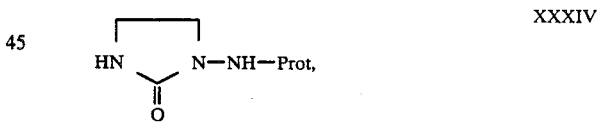

XXXIV wherein the symbol Prot can be an amino protecting group such as t-butoxycarbonyl or benzyloxycarbonyl, with phosgene to yield

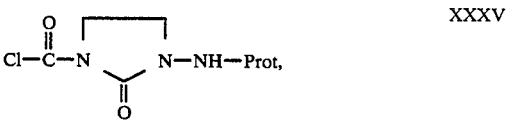

XXXV which can be reacted with hexamethylsilazane to yield

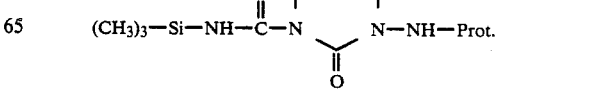

XXXVI

Hydrolytic cleavage of the silyl group in a compound of formula XXXVI yields

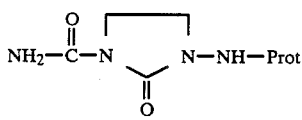   XXXVII

Cleavage of the amino protecting group in a compound of formula XXXVII yields

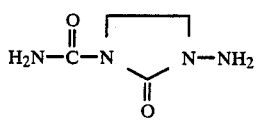   XXXVIII

Reaction of the compound of formula XXXVIII with an optionally protected activated form of a compound of formula XX yields

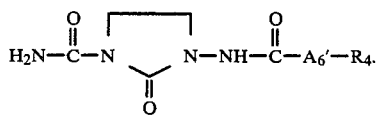   XXXIX

A salt of the compound of formula XXXVIII can be prepared by reacting the compound of formula

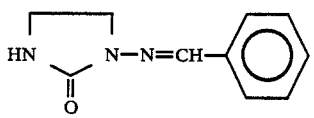   XL with chlorosulfonylisocyanate followed by mild hydrolysis of the reaction product to yield a compound of formula

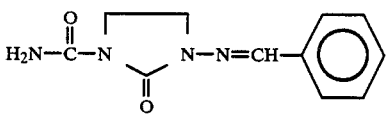   XLI which, on further hydrolysis, e.g., by reflux with diluted aqueous acid yields the salt of the compound of formula XXXVIII.

The nucleophiles of formula V wherein R is

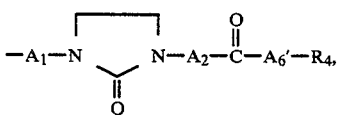

$A_1$ is

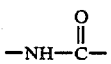

and $A_2$ is —$CH_2$—$CH_2$—NH— can be prepared by first deprotecting 1-(aminocarbonyl)-3-[2-[[(t-butoxy)carbonyl]amino]ethyl]-2-imidazolidinone and coupling the resulting compound with an activated form of a compound of formula XX (optionally protected) to obtain after deprotection

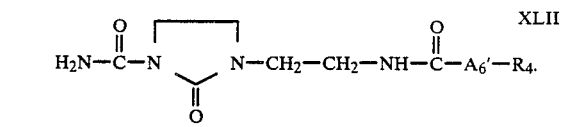   XLII

The nucleophiles of formula V wherein R is

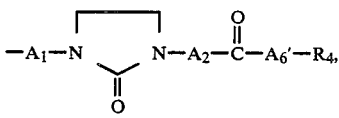

$A_1$ is

and $A_2$ is

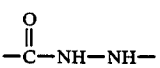

can be prepared by reacting a compound of formula XXIX (optionally silylated and protected) with phosgene to yield an optionally protected derivative of a compound having the formula $$Cl-\overset{O}{\underset{}{C}}-N\phantom{xx}N-\overset{O}{\underset{}{C}}-NH-NH-\overset{O}{\underset{}{C}}-A_6'-R_4.$$   XLIII which can be reacted with hexamethyldisilazane to yield an (optionally protected) compound of the formula $$(CH_3)_3Si-NH-\overset{O}{\underset{}{C}}-N\phantom{xx}N-\overset{O}{\underset{}{C}}-NH-NH-\overset{O}{\underset{}{C}}-A_6'-R_4.$$   XLIV A non-silylated derivative of a compound of formula XLIV can be prepared by reacting a protected form of a compound of formula XXIX with chlorosulfonylisocyanate followed by hydrolysis of the resulting intermediate and cleavage of the protecting groups to yield

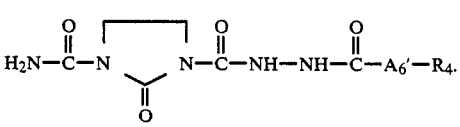   XLV

Alternatively, compound XXVII can be reacted with chlorosulfonylisocyanate followed by hydrolysis of the resulting intermediate and cleavage of the protecting groups to yield the compound

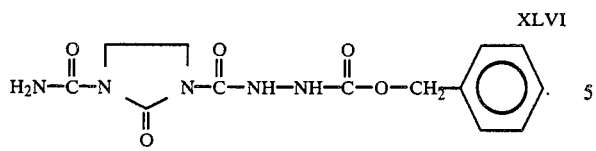　XLVI

Deprotection of XLVI by hydrogenolysis yields

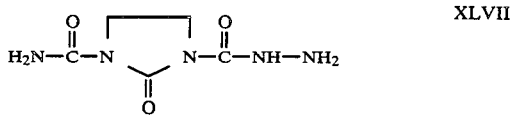　XLVII which can be coupled with an activated (optionally protected) derivative of a compound of formula XX to yield

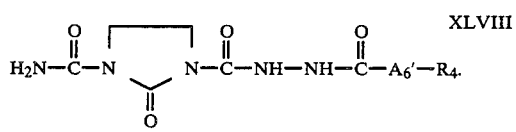　XLVIII

The nucleophiles of formula V wherein R is

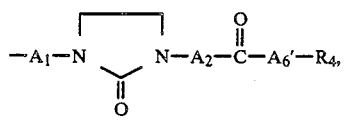

$A_1$ is —NH— and $A_2$ is a single bond can be prepared by coupling the compound of formula XXXIV to an activated form of a compound of formula XX (optionally protected) and cleaving the protecting group to yield

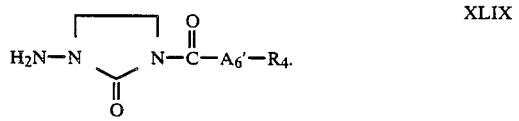　XLIX

The nucleophiles of formula V wherein R is

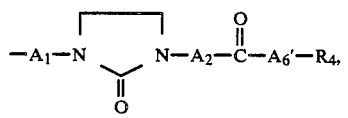

$A_1$ is —NH— and $A_2$ is —NH— can be prepared by coupling a monoprotected (preferably with t-butoxycarbonyl or benzyloxycarbonyl) derivative of 1,3-diamino-2-imidazolidinone with an activated form of a compound of formula XX (optionally protected) and deprotecting the resulting compound to yield

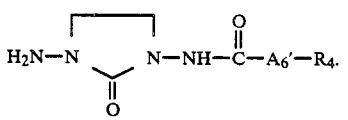　L

The nucleophiles of formula V wherein R is

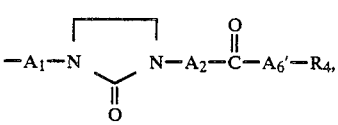

$A_1$ is —NH— and $A_2$ is —CH$_2$—CH$_2$—NH— can be prepared by nitrosating a compound of formula XXV (suitably protected) to yield a compound having the formula

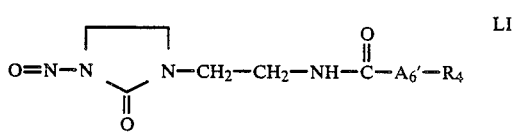　LI (suitably protected) and reducing and deprotecting that compound to yield

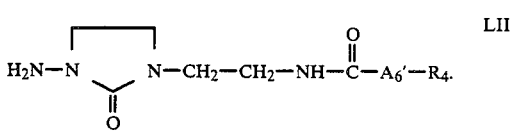　LII

The nucleophiles of formula V wherein R is

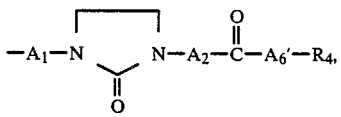

$A_1$ is —NH— and $A_2$ is

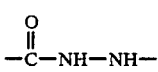

can be prepared by nitrosating, reducing and deprotecting a protected derivative of a compound of formula XXIX. The resulting compound has the formula

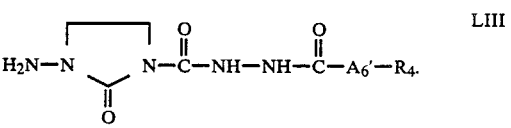　LIII

Alternatively, a compound of formula LIII can be prepared by reacting a compound of formula XXXIV with phosgene to yield

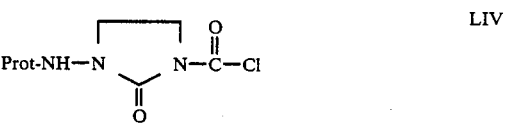　LIV which, on reaction with a monoprotected hydrazine in the presence of base, yields

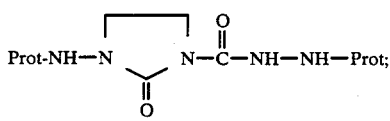  LV (The two protecting groups must be different). Selective removal of the hydrazide protecting group yields

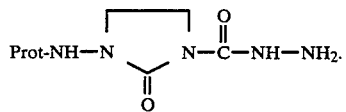  LVI

Coupling of a compound of formula LVI with an activated optionally protected form of a compound of formula XX, followed by deprotection, yields a compound of formula LIII.

The nucleophiles of formula V wherein R is

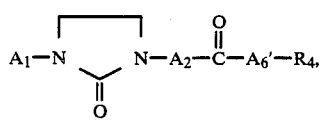

$A_1$ is

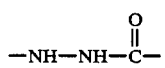

and $A_2$ is a single bond can be prepared by reacting a compound of formula XXXI (preferably a protected derivative thereof) with hydrazine (preferably in monoprotected form) in the presence of a base or with a silylated form of hydrazine or monoprotected hydrazine to yield a protected derivative of

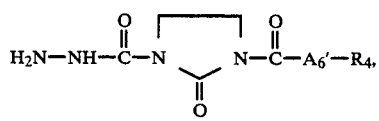  LVII which can be deprotected using conventional techniques.

Alternatively, a compound of formula XXVIII (either a silylated derivative thereof or an anion thereof formed by reaction with a strong base) can be reacted with an activated form of formula XX (suitably protected) and deprotected to yield a compound of formula LVII.

The nucleophiles of formula V wherein R is

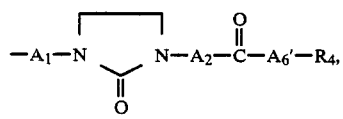

$A_1$ is

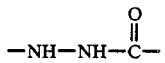

and $A_2$ is —NH— can be prepared by reacting a protected derivative of formula XXXV with a monoprotected derivative of hydrazine in the presence of a base to yield a protected derivative of the compound having the formula

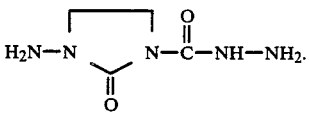  LVIII

The groups used to protect the terminal amino groups in a compound of formula LVIII should be chosen so that the protecting group of the non-hydrazino amino group can be selectively removed. The resulting compound can be coupled with an activated form of an acid of formula XX (or a protected derivative thereof) to yield (after deprotection) a compound having the formula

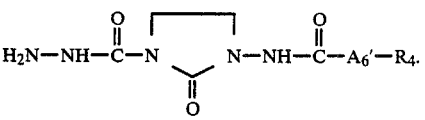  LIX

Alternatively, a compound of formula LV can be selectively deprotected to yield a compound of formula

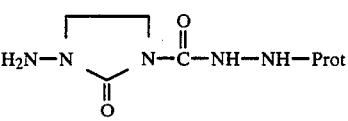  LX which can be coupled to an activated form of a compound of formula XX (or a protected derivative thereof) and deprotected to yield a compound of formula LIX The nucleophiles of formula V wherein R is

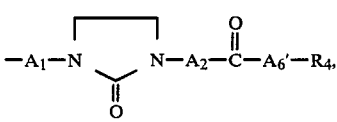

$A_1$ is

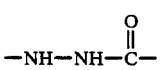

and $A_2$ is —CH$_2$—CH$_2$—NH— can be prepared by sequentially reacting a compound of formula XXV (or a silylated and/or protected derivative thereof) with phosgene followed by hydrazine (or a monoprotected derivative thereof) to yield upon deprotection

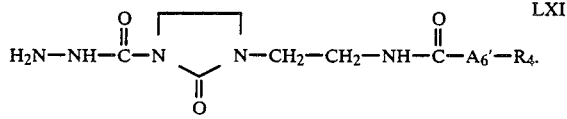 LXI

Alternatively, an amino protected derivative of 1-(2-aminoethyl)-2-imidazolidinone (optionally silylated) can be reacted with phosgene, and then with a monoprotected derivative of hydrazine in the presence of a base to yield a protected derivative of the compound having the formula

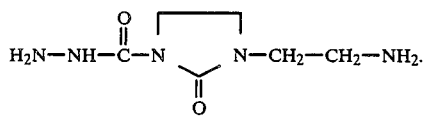 LXII

The groups used to protect the terminal amino groups in a compound of formula LXII should be chosen so that the protecting group on the aminoethyl group can be selectively removed. The resulting monodeprotected compound can be coupled with an activated form of an acid of formula XX (or a protected derivative thereof) to yield (after deprotection) a compound of formula LXI.

the nucleophiles of formula V wherein R is

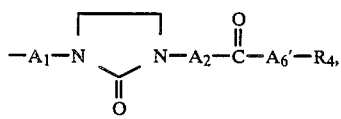

$A_1$ is

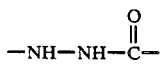

and $A_2$ is

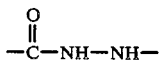

can be prepared by reacting the compound of formula XXVIII (optionally as a silylated derivative thereof) with phosgene to yield a protected derivative of the compound having the formula

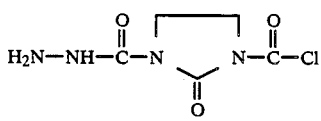 LXIII which can be coupled with a protected derivative of hydrazine to yield a protected derivative of

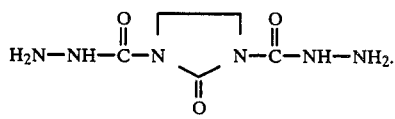 LXIV

The groups used to protect the terminal amino groups in a compound of formula LXIV should be chosen so that one of the protecting groups can be selectively removed. The resulting monodeprotected compound can be coupled with an optionally protected activated form of an acid of formula XX to yield (after deprotection) a compound having the formula

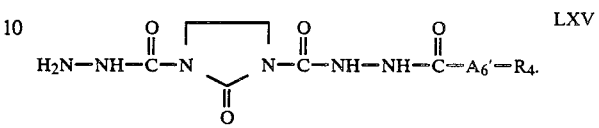 LXV

The nucleophiles of formula V wherein R is

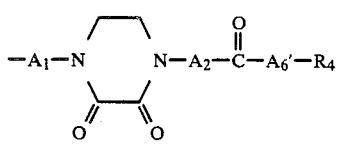

can be prepared using the methodology described above for the preparation of the nucleophiles of formula V wherein R is

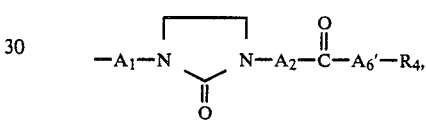

but substituting the appropriate 2,3-piperazinedione reactants for the 2-imidazolidinone reactants.

The nucleophiles of formula V wherein R is

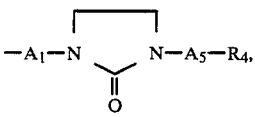

$A_1$ is a single bond and $A_5$ is $-(CH_2)_p-$ can be prepared by reacting an optionally protected derivative of a compound having the formula $$NH_2-(CH_2)_p-R_4 \quad \text{LXVI}$$

with 2-(chloroethyl)isocyanate to yield the compound having the formula

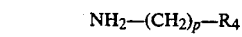 LXVII

The compounds of formula LXVI are readily obtainable using literature procedures. Treatment of LXVII with base yields the compound having the formula

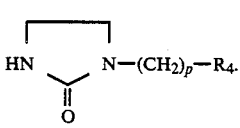 LXVIII

The nucleophiles of formula V wherein R is

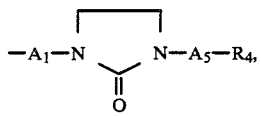

$A_1$ is a single bond and $A_5$ is —N=CH— can be prepared by condensing 1-amino-2imidazolidinone with the aldehyde having the formula

 LXIX (or a methyl or benzyl ether thereof, or a silylated derivative thereof) to yield the compound having the formula

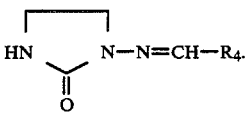 LXX

The nucleophiles of formula V wherein R is

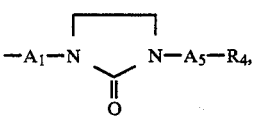

$A_1$ is a single bond and $A_5$ is —NH—CH$_2$— can be prepared by hydrogenation of a compound of the formula LXX to yield a compound of the formula

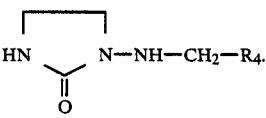 LXXI

The nucleophiles of formula V wherein R is

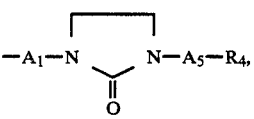

$A_1$ is a single bond and $A_5$ is

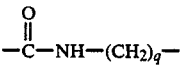

can be prepared by reacting 1-chlorocarbonyl-2-imidazolidinone with a compound having the formula

 LXXII (or an hydroxy protected derivative thereof) in the presence of a base, or with a silylated derivative of a compound of formula LXXII, to yield following deprotection the compound having the formula

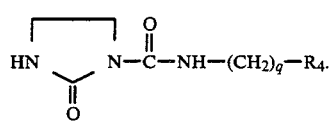 LXXIII

The nucleophiles of formula V wherein R is

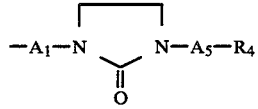

and $A_1$ is

can be prepared by reacting an hydroxy protected derivative of a compound of formula LXVIII, LXX, LXXI or LXXIII (optionally silylated) with phosgene to yield

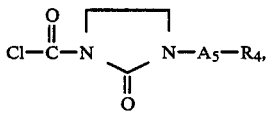 LXXIV which can be reacted with hexamethylsilazane to yield

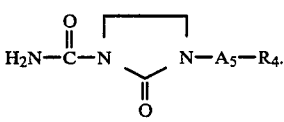 LXXV

The nucleophiles of formula V wherein R is

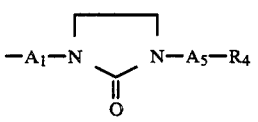

and $A_1$ is —NH— can be prepared by nitrosating a suitably protected derivative of a compound of formula LXVIII, LXX, LXXI, or LXXIII (with, for example, nitrous acid), reducing the resulting compound (using, for example, zinc under acidic conditions) and deprotecting to yield

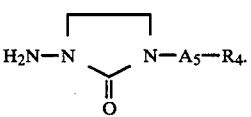 LXXVI

Alternatively, the compounds of formula LXXVI wherein $A_5$ is —N=CH— can be prepared by reacting monoprotected 1,3-diamino-2-imidazolidinone with a compound of formula LXIX (or a protected derivative thereof) and deprotecting the product.

Alternatively, the compounds of formula LXXVI wherein $A_5$ is —NH—CH$_2$— can be prepared by reducing the carbon-nitrogen double bond of those compounds of formula LXXVI wherein $A_5$ is —N=CH— (e.g., with sodium cyanoborohydride).

The nucleophiles of formula V wherein R is

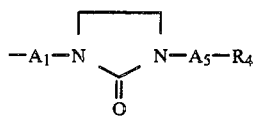

and $A_1$ is

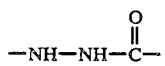

can be prepared by reacting a compound of formula LXXIV with a monoprotected hydrazine in the presence of a base or with a silylated derivative of hydrazine. The products, after deprotection, have the formula

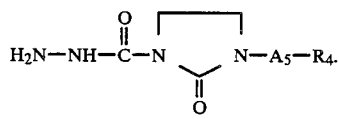 LXXVII

The nucleophiles of formula V wherein R is

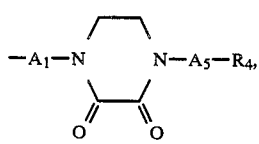

$A_1$ is a single bond and $A_5$ is —(CH$_2$)$_p$— can be prepared by reacting a compound having the formula LXVI (or an hydroxyl protected derivative thereof) with aziridine to yield H$_2$N—CH$_2$—CH$_2$—NH—(CH$_2$)$_p$—R$_4$. LXXVIII A compound of formula LXXVIII can be reacted with a dialkyl oxalate to yield

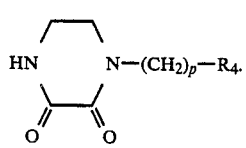 LXXIX

The nucleophiles of formula V wherein R is

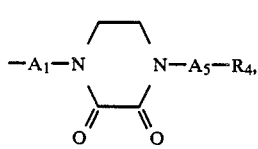

$A_1$ is a single bond and $A_5$ is —N=CH— or —NHCH$_2$— can be prepared using the methodology described above for the preparation of the nucleophiles of formula V wherein R is

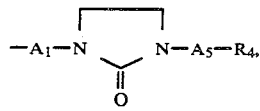

$A_1$ is a single bond and $A_5$ is —N=CH— or —NH—CH$_2$—, but substituting 1-amino-2,3-piperazinedione for 1-amino-2-imidazolidinone. The resulting compounds would have the formulas

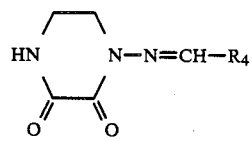 LXXX and

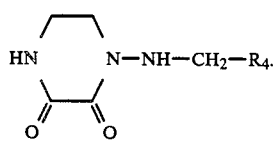 LXXXI

The nucleophiles of formula V wherein R is

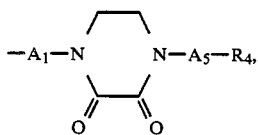

$A_1$ is a single bond and $A_5$ is

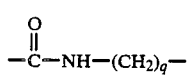

can be prepared by reacting a protected derivative of

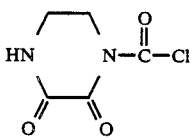 LXXXII with a compound of formula LXXII (or an hydroxyl protected derivative thereof) in the presence of a base or by using a silylated derivative of LXXII. The resulting intermediate can be deprotected to yield

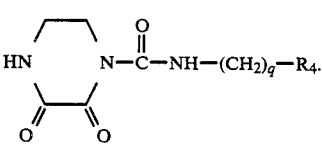 LXXXIII

The nucleophiles of formula V wherein R is

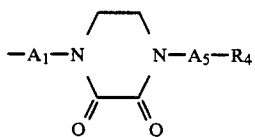

and A₁ is —NH— can be prepared by nitrosation of a protected derivative of a compound having the formula LXXIX, LXXX, or LXXXIII (with, for example, nitrous acid), reducing the resulting compound (using, for example, zinc under acidic conditions) and deprotecting to yield

LXXXIV

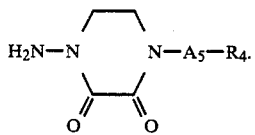

Alternatively, those compounds of formula LXXXIV wherein A₅ is —N=CH— can be prepared by reacting monoprotected, 1,4-diamino-2,3-piperazinedione with a compound of formula LXIX (or a protected derivative thereof) and deprotecting the product.

Alternatively, those compounds of formula LXXXIV wherein A₅ is —NH—CH₂— can be prepared by reduction of the carbon-nitrogen bond of those compounds of formula LXXXIV wherein A₅ is —N=CH— (e.g., with sodium cyanoborohydride).

The nucleophiles of formula V wherein R is

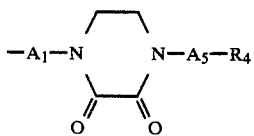

and A₁ is

can be prepared by reacting a hydroxy protected derivative of the formula

LXXXV

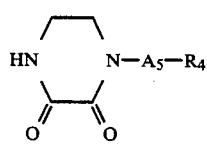

with phosgene to yield

LXXXVI

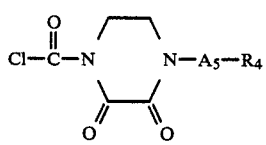

which can be reacted with hexamethyldisilizane to yield

LXXXVII

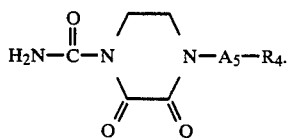

The nucleophiles of formula V wherein R is

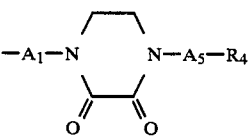

and A₁ is

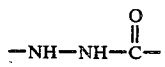

can be prepared by reacting a compound of formula LXXXVI with a protected derivative of hydrazine to yield (upon deprotection)

LXXXVIII

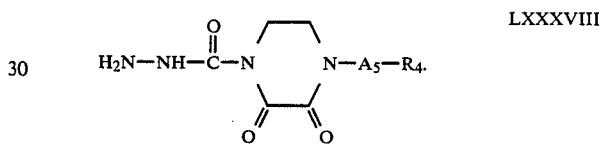

The nucleophiles of formula V wherein R is —NH—A₃—R₄ and A₃ is —(CH₂)$_p$— have been described; see formula LXVI.

The nucleophiles of formula V wherein R is —NH—A₃—R₄ and A₃ is

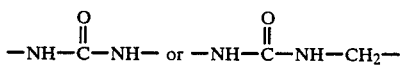

can be prepared by reacting a compound of formula XXVI with a compound of formula LXVI, wherein p is 0 or 1, (optionally protected) in the presence of base or with a silylated form of LXVI followed by removal of any protecting groups.

The nucleophiles of formula V wherein R is —NH—A₃—R₄ and A₃ is

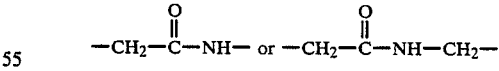

can be prepared by coupling an N-protected glycine derivative with a compound of formula LXVI, wherein p is 0 or 1, (optionally protected) followed by deprotection.

The nucleophiles of formula V wherein R is —NH—A₃—R₄ and A₃ is —NH—CH₂— can be prepared by reacting a protected derivative of the aldehyde of formula LXIX with monoprotected hydrazine followed by reduction of the carbon-nitrogen double bond and subsequent deprotection.

The nucleophiles of formula V wherein R is —NH—A₃—R₄ and A₃ is —O—CH₂— can be prepared by reacting a suitably protected derivative of the compound of the formula

HO—CH$_2$—R$_4$    LXXXIX with N-hydroxybenzotriazole (using, for example, Mitsunobu conditions: the presence of triphenylphosphine and diethylazodicarboxylate) to yield a protected derivative of the compound

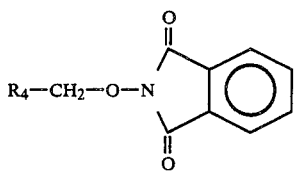    XC which can be deprotected to the compound

R$_4$—CH$_2$—O—NH$_2$,    XCI

The nucleophiles of formula V wherein R is

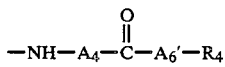

and A$_4$ is —NH— can be prepared by reacting an optionally protected hydrazine with an activated, protected derivative of an acid of formula XX to obtain, after deprotection, a compound of the formula

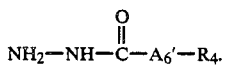    XCII

The nucleophiles of formula V wherein R is

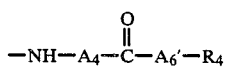

and A$_4$ is —(CH$_2$)$_p$— and p is 0 can be prepared by reacting ammonia with an activated, protected derivative of an acid of formula XX to obtain, after deprotection, a compound having the formula

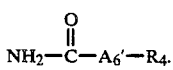    XCIII

The nucleophiles of formula V wherein R is

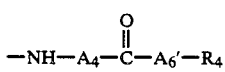

and A$_4$ is —(CH$_2$)$_p$— and p is 1 can be prepared by treatment of an optionally protected compound of the formula

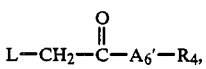    XCIV wherein L is a leaving group, with an inorganic azide to form a compound (optionally protected) of the formula

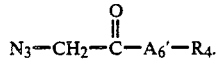    XCV

Reduction of the azido group (e.g., using hydrogen sulfide and triethylamine) yields a compound of the formula

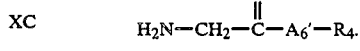    XCVI

Alternatively, a compound of formula XCIV can be reacted with hexamethylentetramin having the formula

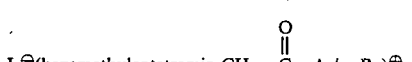    XCVII

L$^\ominus$(hexamethylentetramin-CH$_2$—C—A$_6'$—R$_4$)$^\oplus$, which on treatment with a strong acid yields a compound of the formula

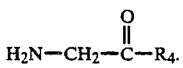    XCVIII

The nucleophile of formula V wherein R is

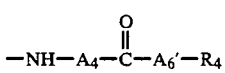

and A$_4$ is —(CH$_2$)$_y$—NH— can be prepared by reacting a (optionally monoprotected) compound of formula NH$_2$—(CH$_2$)$_y$—NH$_2$    XCIX with an activated, optionally protected derivative of an acid of formula XX to obtain, after deprotection, a compound having the formula

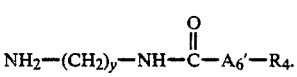    C

The nucleophiles of formula V wherein R is

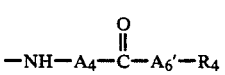

and A$_4$ is

can be prepared by reacting

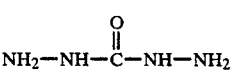

with an activated, protected derivative of an acid of formula XX to obtain, after deprotection, a compound of the formula

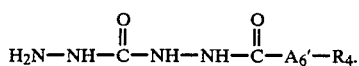

The nucleophiles of formula V wherein R is

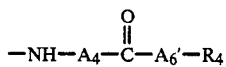

and $A_4$ is

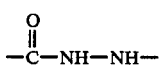

can be prepared by reacting

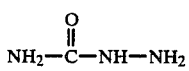

(in the presence of a base or a silylating agent) with an activated, optionally protected derivative of formula XX to obtain, after deprotection, a compound having the formula

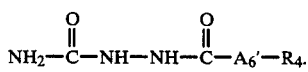
CII

The nucleophile of formula V wherein R is

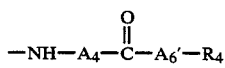

and $A_4$ is

can be prepared by reacting an optionally protected hydrazine derivative of the formula $$NH_2-NH-CH_2-X_8 \qquad CIII$$

with an activated, optionally protected derivative of an acid of formula XX to obtain, after deprotection, a compound having the formula

CIV

The nucleophiles of formula V wherein R is

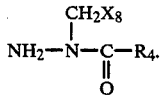

and $A_6$ is $-NH-(CH_2)_p-$ can be prepared by reacting an optionally protected compound of the formula

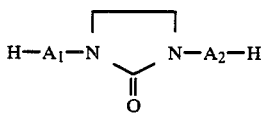
CI with an isocyanate of the formula $$O=C=N-(CH_2)_p-R_4 \qquad CVI$$

to yield, after deprotection, a compound of the formula

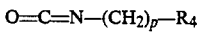
CVII

Alternatively, a compound of formula CVI, optionally protected, can be reacted with phosgene to yield a compound of the formula

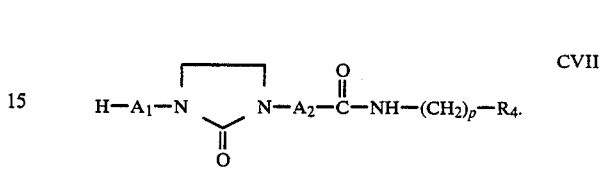
CVIII which on treatment with a compound of formula LXVI yields a compound of formula CVII.

Alternatively, the nucleophiles of formula V wherein R is

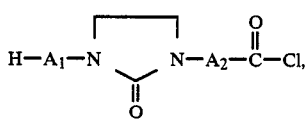

$A_1$ is

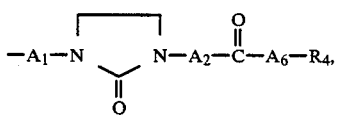

and $A_6$ is $-NH-(CH_2)_p-$ can be prepared by reacting a compound of the formula

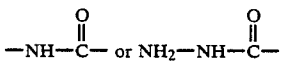
CIX (optionally silylated) with phosgene to yield a compound of the formula

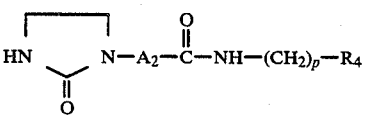
CX

A compound of formula CX can be reacted with hexamethyldisilazane followed by hydrolysis of the remaining silyl group on the nitrogen to yield the corresponding compound having the formula

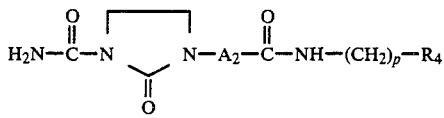
CXI or with monoprotected hydrazine to yield, after deprotection,

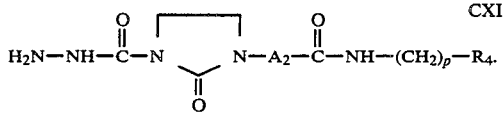
CXII

The nucleophiles of formula V wherein R is

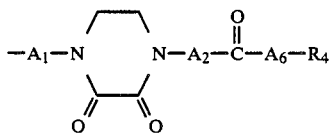

and $A_6$ is —NH—$(CH_2)_p$— can be prepared using the methodology described above for the preparation of the nucleophiles of formula V wherein R is

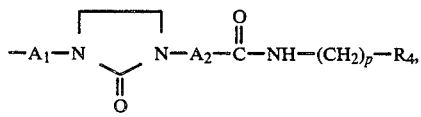

but substituting the appropriate 2,3-piperazinedione reactants for the 2-imidazolidinone reactants.

The nucleophiles of formula V wherein R is

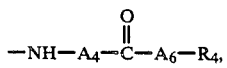

$A_4$ is —NH— and $A_6$ is —NH—$(CH_2)_p$— can be prepared by reacting optionally monoprotected hydrazine with a compound of formula CVI to yield

CXIII

Alternatively, the compound of formula XXVI can be reacted with a compound of formula LXVI in the presence of base to yield, after cleavage of the benzyloxycarbonyl protecting group, a compound of formula CXIII.

The nucleophiles of formula V wherein R is

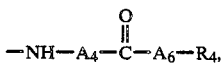

$A_4$ is —$(CH_2)_p$— and $A_6$ is —NH—$(CH_2)_p$— can be prepared by reacting an N-protected, activated compound of the formula

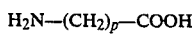
CXIV with a compound of formula LXVI to yield

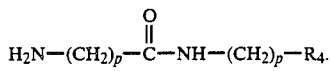
CXV

The nucleophiles of formula V wherein R is

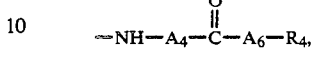

$A_4$ is —$(CH_2)_y$—NH—, and $A_6$ is —NH—$(CH_2)_p$— can be prepared by reacting an optionally monoprotected derivative of a compound of the formula

CXVI with a compound of formula CVI to yield

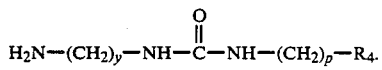
CXVII

The nucleophiles of formula V wherein R is

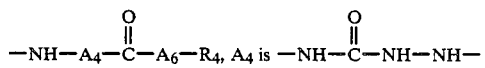

and $A_6$ is —NH—$(CH_2)_p$— can be prepared by reacting an optionally monoprotected derivative of a compound of the formula

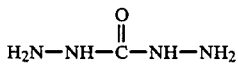
CXVIII with a compound of formula CVI to yield

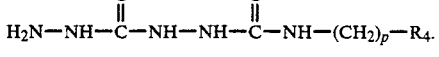
CXIX

Alternatively, a monoprotected derivative of a compound of formula CXVIII can be reacted with phosgene to yield a protected derivative of

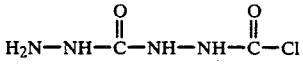
CXX which can be treated with a compound of formula LXVI to yield a compound of formula CXIX.

The nucleophiles of formula V wherein R is

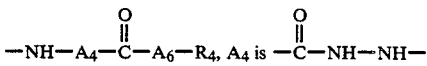

and $A_6$ is —NH—$(CH_2)_p$— can be prepared by reacting semi-carbazide with a compound of formula CV to yield

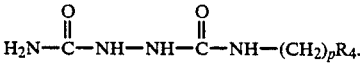
CXXI

Alternatively, a compound of formula LXVI can be reacted with phosgene to yield

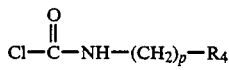 CXXII which can be reacted with semicarbazide, preferably in the presence of base, to yield a compound of formula CXXI.

The nucleophiles of formula V wherein R is

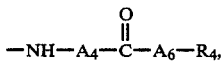

$A_4$ is

and $A_6$ is —NH—$(CH_2)_p$— can be prepared by reacting an optionally protected compound of formula CIV with a compound of formula CVI to yield, after deprotection, a compound of the formula

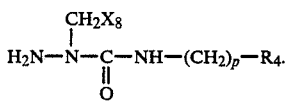 CXXIII

Alternatively, a suitably protected derivative of a compound of formula CIV can be reacted with phosgene to yield a protected derivative of

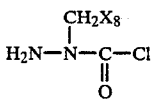 CXXIV which can be reacted with a compound of formula LXVI, preferably in the presence of base, to yield, after deprotection, a compound of formula CXXIII.

The compounds of formula I wherein $R_1$ is

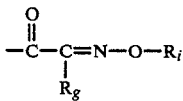

and $R_g$ is 2-amino-4-thiazolyl and $R_i$ is methyl, ethyl, carboxymethyl, 1-carboxy-1-methylethyl, 1-carboxy-1-ethyl or

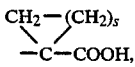

wherein s is 1, 2 or 3. The use of these preferred $R_1$ acyl groups yields a product which exists as the syn or anti isomer or as a mixture of isomers. The syn isomer exhibits greater activity than the anti isomer.

The following examples are specific embodiments of this invention.

EXAMPLE 1

(S)-2-Amino-N-[1-[[[[3-[(3,4-dihydroxybenzoyl)amino]-2-oxo-1-imidazolidinyl]sulfonyl]amino]carbonyl]-2-oxo-2-azetidinyl]-α-(methoxyimino)-4-thiazoleacetamide, triethylamine salt (1:1)

(A)

1-[[3,4-Bis(acetyloxy)benzoyl]amino]-2-imidazolidinone

1-Amino-2-imidazolidinone (2.61 g, 0.026 mol) was dissolved in 200 ml of dichloromethane. The solution was cooled to 0° C. and 4.1 ml of triethylamine was added, followed by 7.5 g of 3,4-bis(acetyloxy)benzoyl chloride (0.029 mol). The mixture was stirred at 0° C. for 1 hour and at room temperature for an additional hour. The precipitate was filtered off to yield 8.3 g of 1-[[3,4-bis(acetyloxy)benzoyl]amino]-2-imidazolidinone.

(B)

(S)-[1-[[[[3-[[3,4-bis(acetyloxy)benzoyl]amino]-2-oxo-1-imidazolidinyl]sulfonyl]amino]carbonyl]-2-oxo-3-azetidinyl]carbamic acid, phenylmethyl ester 1-[[3,4-Bis(acetyloxy)benzoyl]amino]-2-imidazolidinone (3.2 g, 0.01 mol) was suspended in 50 ml of ethyl acetate. N-Methyl-N-(trimethylsilyl)trifluoracetamide (3.99 g, 0.02 mol) was added, and the mixture was stirred for 45 minutes and heated to 80° C. (bath) for 30 minutes. The clear solution was added at 0° C. to a solution of (S)-[1-[[(chlorosulfonyl)amino]carbonyl]-2-oxo-3-azetidinyl]carbamic acid, phenylmethyl ester (0.01 mol), prepared from 2.2 g of (S)-(2-oxo-3-azetidinyl)carbamic acid, phenylmethyl ester and 0.9 ml of chlorosulfonyl isocyanate in 60 l of ethyl acetate at room temperature (1 hour). The mixture was stirred with brine (twice), dried with magnesium sulfate and evaporated to yield, after trituration with ether, 5.6 g of crude (S)-[1-[[[[3-[[3,4-bis(acetyloxy)benzoyl]amino]-2-oxo-1-imidazolidinyl]sulfonyl]amino]carbonyl]-2-oxo-3-azetidinyl]carbamic acid, phenylmethyl ester.

(C)

(S)-[1-[[[[3-[(3,4-dihydroxybenzoyl)amino]-2-oxo-1-imidazolidinyl]sulfonyl]amino]carbaonyl]-2-oxo-3-azetidinyl]carbamic acid, phenylmethyl ester Crude (S)-[1-[[[[3-[[3,4-bis(acetyloxy)benzoyl]amino]-2-oxo-1-imidazolidinyl]sulfonyl]amino]carbonyl]-2-oxo-3-azetidinyl]carbamic acid, phenylmethyl ester (5.6 g, 0.008 mol) was dissolved in 200 ml of tetrahydrofuran. The solution was added, with stirring, to a solution of 112 g (1.5 mol) of ammonium acetate in 900 ml of water. The mixture was well stirred for 3½ hours, when only traces of starting material could be detected (tlc). The solution was evaporated to a small volume, then lyophilized. The product obtained was suspended with a small amount of water and isolated by filtration to yield 2.9 g of the ammonium salt of (S)-[1-[[[[3-[(3,4-dihydroxybenzoyl)amino]-2-oxo-1-imidazolidinyl]sulfonyl]amino]carbonyl]-2-oxo-3-azetidinyl]carbamic acid, phenylmethyl ester.

This material was suspended with 25 ml of water, layered with 100 ml of ethyl acetate and acidified (ice cooling) to pH 1.5 by the addition of 2N hydrochloric acid. The ethyl acetate phase was washed with water, dried (magnesium sulfate) and evaporated to yield 1.9 g of (S)-[1-[[[[3-[(3,4-dihydroxybenzoyl)amino]-2-oxo-1- imidazolidinyl]sulfonyl]amino]carbonyl]-2-oxo-3-azetidinyl]carbamic acid, phenylmethyl ester.

(D)
(S)-3-Amino-N-[[3-[(3,4-dihydroxybenzoyl)amino]-2-oxo-1-imidazolidinyl]sulfonyl]-2-oxo-1-azetidinecarboxamide, trifluoroacetate salt (S)-1-[[[[3-[(3,4-dihydroxybenzoyl)amino]-2-oxo-1-imidazolidinyl]sulfonyl]amino]carbonyl]-2-oxo-3-azetidinyl]carbamic acid, phenylmethyl ester (1.7 g, 0.003 mol) was added at room temperature to a mixture prepared from 5 ml of trifluoroacetic acid and 1.2 ml of thioanisole. The mixture was stirred at room temperature overnight. The trifluoroacetic acid was evaporated and the residue was treated with ether to yield 1.6 g of (S)-3-amino-N-[[3-[(3,4-dihydroxybenzoyl)amino]-2-oxo-1-imidazolidinyl]sulfonyl]-2-oxo-1-azetidinecarboxamide, trifluoroacetate salt.

(E)
(S)-2-Amino-N-[1-[[[[3-[(3,4-dihydroxybenzoyl)amino]-2-oxo-1-imidazolidinyl]sulfonyl]amino]carbonyl]-2-oxo-2-azetidinyl]-α-(methoxyimino)-4-thiazoleacetamide, triethylamine salt (1:1)

(S)-3-Amino-N-[[3-[(3,4-dihydroxybenzoyl)amino]-2-oxo-1imidazolidinyl]sulfonyl]-2-oxo-1-azetidinecarboxamide, trifluoroacetate salt (0.54 g, 0.001 mol) was dissolved at room temperature in 10 ml of dimethylformamide. Then, 0.32 g (0.001 mol) of (Z)-2-amino-α-(methoxyimino)-4-thiazoleacetic acid, N-hydroxybenzotriazole ester was added, followed by 0.14 ml (0.001 mol) of triethylamine. The mixture was stirred at room temperature overnight. The dimethylformamide was evaporated in vacuo and the residue triturated with ether to yield 0.7 g of crude product. The crude product was dissolved in a mixture of 10 ml of acetone and 10 ml of water. The pH of the solution was adjusted to 6.5 by the addition of sodium bicarbonate solution. The acetone was evaporated in vacuo and the aqueous solution purified by column chromatography on HP-20 eluting with water, then with water/acetone (9:1), yielding 0.27 g of (S)-2-amino-N-[1-[[[[3-[(3,4-dihydroxybenzoyl)amino]-2-oxo-1-imidazolidinyl]sulfonyl]amino]carbonyl]-2-oxo-2-azetidinyl]-α-(methoxyimino)-4-thiazoleacetamide, triethylamine salt (1:1), melting point 186° C., dec.

EXAMPLE 2

2-[[[1-(2-Amino-4-thiazolyl)-2-[[1-[[[[3-[(3,4-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt (A)
2-[[[1-(2-Amino-4-thiazolyl)-2-[[1-[[[[3-[(3,4-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (Z)-2-Amino-α-[[1-(diphenylmethoxycarbonyl)-1-methylethoxy]imino]-4-thiazoleacetic acid (0.88 g, 0.002 mol) was dissolved in 20 ml of dimethylformamide followed by 0.3 g of N-hydroxybenzotriazole (containing 13% water), followed by 0.5 g of dicyclohexylcarbodiimide and 0.28 ml of triethylamine. The mixture was stirred at room temperature for 1 hour, then 1.08 g (0.002 mol) of (S)-3-amino-N-[[3-[(3,4-dihydroxybenzoyl)amino]-2-oxo-1-imidazolidinyl]sulfonyl]-2-oxo-1-azetidinecarboxamide, trifluoroacetate salt (see Example 1D) was added. The mixture was stirred at room temperature overnight. The precipitate (dicyclohexylurea) was filtered off and the filtrate evaporated in vacuo. Trituration of the remaining syrup with ether yielded 1.8 g of the title compound in crude form.

(B)
2-[[[1-(2-Amino-4-thiazolyl)-2-[[1-[[[[3-[(3,4-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt 2-[[[1-(2-Amino-4-thiazolyl)-2-[[1-[[[[3-[(3,4-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (1.8 g, 0.002 mol) was suspended in 3 ml of anisole. At −10° C., 15 ml of trifluoroacetic acid was added dropwise and the mixture stirred at this temperature for 1 hour. Addition of ca. 100 ml of ether at −10° C. precipitated the crude acid of the title compound (1.3 g). The crude product was suspended in 50 ml of water and the pH of the suspension was adjusted to 6.5 by the addition of sodium bicarbonate solution to form an almost clear solution. After lyophilization of the filtered solution, 1.1 g of crude product was obtained.

Chromatography on HP-20 (elution with water and water/acetone 90:10) yielded 0.17 g of pure product, melting point >240° C. and 0.23 g of slightly contaminated product.

EXAMPLE 3

[3S(Z)]-2-[[[1-(2-Amino-4-thiazolyl)-2-[[1-[[[[2-(3,4dihydroxybenzoyl)hydrazino;9 sulfonyl]amino]carbonyl]-2-oxo-3-azetidinyl]amino]-2-oxoethylidene]amino]oxy]-2-methylpropanoic acid, disodium salt (A)
(S)-[1-[[[[2-(3,4-Dihydroxybenzoyl)hydrazino]sulfonyl]amino]carbonyl]-2-oxo-3-azetidinyl]carbamic acid, phenylmethyl ester To a suspension of 1.6 g (0.01 mol) of 3,4-dihydroxybenzoic acid, hydrazide in 20 ml of ethyl acetate was added 11.4 ml of trimethylsilyl chloride (0.09 mol) and 8.4 ml of triethylamine (0.06 mol). The mixture was stirred at room temperature overnight, filtered (5.8 g of triethylamine hydrochloride) and evaporated to yield silylated 3,4-dihydroxybenzoic acid, hydrazide as a syrup. The syrup was dissolved in 30 ml of dichloromethane and added dropwise to a solution of (S)-[1-[[(chlorosulfonyl)amino]carbonyl]-2-oxo-3-azetidinyl]-carbamic acid, phenylmethyl ester, prepared from 2.2 g (0.01 mol) of (S)-(2-oxo-3-azetidinyl)carbamic acid, phenylmethyl ester and 0.9 ml of chlorosulfonyl isocyanate in 70 ml of ethyl acetate. The mixture was stirred overnight at room temperature and washed with 50 ml of brine. The organic phase was dried (magnesium sulfate), evaporated and the residue treated with ether to yield 3.8 g of crude (S)-[1-[[[[2-(3,4-dihydroxybenzoyl)-hydrazino]sulfonyl]amino]carbonyl]-2-oxo-3-azetidinyl]carbamic acid, phenylmethyl ester. The crude (S)-[1-[[[[2-(3,4-dihydroxybenzoyl)hydrazino]sulfonyl]amino]carbonyl]-2-oxo-3-azetidinyl]carbamic acid, phenylmethyl ester was converted to the sodium salt (acetone/water; sodium bicarbonate) which was purified by column chromatography (HP-20, elution with water, then acetone/water 1:9) to yield 1.2 g of the pure sodium salt of (S)-[1-[[[[2-(3,4-dihydroxybenzoyl)hydrazino]sulfonyl]-2-oxo-1-azetidinyl]carbamic acid, phenylmethyl ester, from which 0.8 g of (S)-[1-[[[[2-(3,4-dihydroxybenzoyl)hydrazino]sulfonyl]amino]carbonyl]-2-oxo-3-azetidinyl]carbamic acid, phenylmethyl ester were obtained.

(B)
(S)-3-Amino-N-[[2-(3,4-dihydroxybenzoyl)hydrazino]sulfonyl]-2-oxo-1-azetidinecarboxamide, trifluoroacetate salt (S)-[1-[[[[2-(3,4-Dihydroxybenzoyl)hydrazino]sulfonyl]amino]carbonyl]-2-oxo-3-azetidinyl]carbamic acid, phenylmethyl ester (0.8 g) was added to a mixture of 3 ml of trifluoroacetic acid and 0.75 ml of thioanisole and the mixture was stirred overnight at room temperature. The trifluoroacetic acid was removed in vacuo and the residue triturated with ether to yield 0.5 g of (S)-3-amino-N-[[2-(3,4-dihydroxybenzoyl)hydrazino]sulfonyl]-2-oxo-1-azetidinecarboxamide, trifluoroacetate salt.

(C)
[3S(Z)]-2-[[[1-(2-Amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]-2-methylpropanoic acid, diphenylmethyl ester (Z)-2-Amino-α-[[1-(diphenylmethoxycarbonyl)-1-methylethoxy]imino]-4-thiazoleacetic acid (0.44 g, 0.001 mol) was dissolved in 10 ml of dimethylformamide and 0.15 ml of triethylamine (0.0011 mol) was added, followed (after cooling to −30° C.) by 0.21 ml (0.001 mol) of diphenylchlorophosphate. The reaction mixture was stirred at −10° C. for 2 hours and at 0° C. for 1 hour, evaporated in vacuo to remove the dimethylformamide and triturated with ether to yield 1.1 g of crude [3S(Z)]-2-[[[1-(2-amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]-2-methylpropanoic acid, diphenylmethyl ester, which was treated with water at pH 3 to yield 0.7 g of material, which was used in the next step without further purification.

(D)
[3S(Z)]-2-[[[1-(2-Amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]-2-methylpropanoic acid, disodium salt Trifluoroacetic acid (10 ml) was added dropwise at −10° C. to a suspension of 0.7 g of [3S(Z)]-2-[[[1-(2-amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]-2-methylpropanoic acid, diphenylmethyl ester in 2 ml of anisole. The mixture was stirred at −10° C. for one hour and the trifluoroacetate salt of the product was precipitated from the reaction mixture at −10° C., yielding 0.5 g of crude product.

The crude material was converted to the disodium salt (acetone/water, pH 6.5) and purified by column chromatography (HP-20, elution with water) to yield 0.09 g of the title compound, melting point >235° C., dec.

EXAMPLE 4

[3S(Z)]-2-[[[1-(2-Amino-4-thiazolyl)-2-[[1-[[[[[3-[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, disodium salt (A)
3-[3,4-Bis(acetyloxy)benzoyl]-2-oxo-1-imidazolidinecarboxamide 3-Amino-2-oxo-1-imidazolidinecarboxamide, monohydrochloride (12 g 0.006 mol) was suspended in 300 ml of dichloromethane. The suspension was cooled to 0° C. and 29.2 ml of triethylamine (0.198 mol) was added; the mixture was stirred for another 20 minutes. [3,4-Bis(acetyloxy)benzoyl]chloride (10.5 g) dissolved in 200 ml of dichloromethane was added dropwise with stirring at 0° C. and the mixture was stirred overnight at room temperature, filtered and treated with 50 ml of water. After stirring for 5 minutes, 3-[3,4-bis(acetyloxy)benzoyl]-2-oxo-1-imidazolidinecarboxamide crystallized out (7.2 g) contaminated with some triethylamine hydrochloride. The impurity was removed by treatment with water to yield 6.6 g of 3-[3,4-bis(acetyloxy)benzoyl]-2-oxo-1-imidazolidinecarboxamide, melting point 222°–224° C.

(B)
3-(3,4-Dihydroxybenzoyl)-2-oxo-1-imidazolidinecarboxamide

To a suspension of 6.2 g (0.017 mol) of 3-[3,4-bis(acetyloxy)benzoyl]-2-oxo-1-imidazolidinecarboxamide in 50 ml of a 1:1 mixture of ethanol/water was added dropwise 2.1 ml of ammonia. After stirring for 10 minutes, a clear solution formed from which 3-(3,4-dihydroxybenzoyl)-2-oxo-1-imidazolidinecarboxamide began to crystallize after 15 minutes, yielding 3.8 g.

(C)
(S)-[1-[[[[[3-[(3,4-Dihydroxybenzoyl)amino]-2-oxo-1-imidazolidinyl]carbonyl]amino]sulfonyl]amino]carbonyl]-2-oxo-3-azetidinyl]carbamic acid, phenylmethyl ester 3-(3,4-Dihydroxybenzoyl)-2-oxo-1-imidazlidinecarboxamide (1.4 g, 0.005 mol) was suspended in 30 ml of ethyl acetate and 4.1 ml (0.023 mol) of N-methyl-N-(trimethylsilyl)trifluoroacetamide was added. After stirring for 1 hour, a clear solution of silylated 3-(3,4-dihydroxybenzoyl)-2-oxo-1-imidazolidinecarboxamide had formed. It was added to a solution of (S)-[1-[[(chlorosulfonyl)amino]carbonyl]-2-oxo-3-azetidinyl]carbamic acid, phenylmethyl ester, prepared from 1.1 g (0.005 mol) of (S)-(2-oxo-3-azetidinyl)carbamic acid, phenylmethyl ester and 0.5 ml of chlorosulfonylisocyanate in 30 ml of ethyl acetate at room temperature. The mixture was stirred overnight at room temperature, stirred for 30 minutes with 30 ml of brine, dried (magnesium sulfate), evaporated and the residue treated with ether to yield 2.8 g of (S)-[1-[[[[[3-[(3,4-dihydroxybenzoyl)amino]-2-oxo-1-imidazolidinyl]carbonyl]amino]sulfonyl]amino]carbonyl]-2-oxo-3-azetidinyl]carbamic acid, phenylmethyl ester.

(D)
(S)-N-[[[3-Amino-2-oxo-1-azetidinyl)carbonyl]amino]-sulfonyl]-3-[(3,4-dihydroxybenzoyl)amino]-2-oxo-1-imidazolidinecarboxamide, trifluoroacetate salt (S)-[1-[[[[[3-[(3,4-Dihydroxybenzoyl)amino]-2-oxo-1-imidazolidinyl]carbonyl]amino]sulfonyl]amino]carbonyl]-2-oxo-3-azetidinyl]carbamic acid, phenylmethyl ester (1.4 g) was added to a mixture of 6 ml of trifluoroacetic acid and 1.5 ml of thioanisole. The mixture was stirred overnight at room temperature. The trifluoroacetic acid was removed in vacuo and the residue triturated with ether to yield 1.4 g of crude (S)-N-[[[(3-amino-2-oxo-1-azetidinyl)carbonyl]amino]sulfonyl]-3-[(3,4-dihydroxybenzoyl)amino]-2-oxo-1-imidazolidinecarboxamide, trifluoroacetate salt.

(E)
[3S(Z)]-2-[[[1-(2-Amino-4-thiazolyl)-2-[[1-[[[[[3--[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester (Z)-2-Amino-α-[[1-(diphenylmethoxycarbonyl)-1-methylethoxy]imino]-4-thiazoleacetic acid (0.88 g, 0.002 mol) and 0.3 ml of triethylamine were dissolved in 20 ml of dimethylformamide. The mixture was cooled to −30° C. 0.42 ml of Diphenylchlorophosphate (0.002 mol) was added dropwise followed by 1.2 g (0.002 mol) of (S)-N-[[[(3-amino-2-oxo-1-azetidinyl)carbonyl]amino]sulfonyl]-3-[(3,4-dihydroxybenzoyl)amino]-2-oxo-1-imidazolidinecarboxamide, trifluoroacetate salt 0.3 ml of triethylamine and 10 ml of dimethylformamide. The mixture was stirred for 2 hours at −10° C. and for 1 hour at 0° C. The dimethylformamide was removed in vacuo and the residue treated with water at pH 3 to yield 2.0 g of crude [3S(Z)]-2-[[[1-(2-amino-4-thiazolyl)-2-[[1-[[[[[3-[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester.

(F)
[3S(Z)]-2-[[[1-(2-Amino-4-thiazolyl)-2-[[1-[[[[[3--[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, disodium salt To a suspension of 2 g of crude [3S(Z)]-2-[[[1-(2-amino-4-thiazolyl)-2-[[1-[[[[[3-[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester in 5 ml of anisole was added at −10° C. 30 ml of trifluoroacetic acid. The mixture was stirred at −10° C. for 1 hour and the crude reaction product was precipitated by addition of ether at −10° C. The material was converted to the sodium salt (acetone/water; pH 6.5) and purified by column chromatogrphy on HP-20 (elution with water) yielding 0.3 g of [3S(Z)]-2-[[[1-(2-amino-4-thiazolyl)-2-[[1-[[[[[3-[(3,4-dihydroxybenzoyl)amino]-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, disodium salt, melting point >250° C., dec.

EXAMPLE 5
[3S(Z)]-2-[[[1-(2-Amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, disodium salt

(A) 1-[3,4-Bis(acetyloxy)benzoyl]-2-imidazolidinone

2-Imidazolidinone (8.6 g, 0.1 mol) was suspended in 300 ml of anhydrous ethyl acetate. To the stirred suspension was added at room temperature 38 ml of chlorotrimethylsilane (0.3 mol) followed by 42 ml of triethylamine (0.3 mol). The mixture was stirred overnight at room temperature, the precipitate filtered off and the filtrate evaporated in vacuo to yield 34.2 g of a solid residue. The residue was redissolved with 150 ml of ethyl acetate and cooled to 0° C. To the stirred solution was added dropwise a solution of 17.6 g of [3,4-bis(acetyloxy)benzoyl]chloride (0.068 mol) in 50 ml of ethyl acetate (1 hour). The reaction mixture was stirred at room temperature overnight. The crystals were filtered off, yielding 18.2 g of crude 1-[3,4-bis(acetyloxy)benzoyl]-2-imidazolidinone contaminated with 2-imidazolidinone. The crude material was suspended in 100 ml of water, the suspension stirred for 2 hours and filtered to yield 14.2 g of pure 1-[3,4-bis(acetyloxy)benzoyl]-2-imidazolidinone, melting point 154°–156° C.

(B) 1-(3,4-Dihydroxybenzoyl)-2-imidazolidinone

1-[3,4-Bis(acetyloxy)benzoyl]-2-imidazolidinone (11 g, 0.035 mol) was suspended in a mixture of 50 ml of ethanol and 50 ml of water, 4.2 ml (0.07 mol) of aqueous ammonia solution was added with stirring. After 15 minutes, a clear solution was formed, which was evaporated to a small volume. 1-(3,4-Dihydroxybenzoyl)-2-imidazolidinone crystallized out yielding 6.1 g of the title compound, melting point 208°–210° C.

(C)
(S)-[1-[[[[3-(3,4-Dihydroxybenzoyl)-2-oxo-1-imidazolidinyl]sulfonyl]amino]carbonyl]-2-oxo-3-azetidinyl]carbamic acid, phenylmethyl ester 1-(3,4-Dihydroxybenzoyl)-2-imidazolidinone (2.2 g, 0.01 mol) was suspended in 70 ml of ethyl acetate. To the suspension was added 6.1 ml (0.033 mol) of N-methyl-N-(trimethylsilyl)trifluoroacetamide with stirring. After 30 minutes, a clear solution was formed (solution A).

Simultaneously, 2.2 g (0.01 mol) of (S)-(2-oxo-3-azetidinyl)carbamic acid, phenylmethyl ester was suspended in 70 ml of ethyl acetate. To the suspension was added with stirring at room temperature 1 ml of chlorosulfonyl isocyanate, to form a clear solution (B) which was stirred for 1 hour at room temperature. At 0° C., solution A was added to solution B and the mixture was stirred at room temperature overnight, washed with 100 ml of brine, dried with magnesium sulfate, evaporated and triturated with ether to yield 7.0 g of crude amorphous (S)-[1-[[[[3-(3,4-dihydroxybenzoyl)-2-oxo-1-imidazolidinyl]sulfonyl]amino]carbonyl]-2-oxo-3-azetidinyl]carbamic acid, phenylmethyl ester.

The crude material was converted to the sodium salt (aqueous acetone, sodium bicarbonate, pH 6–6.5, lyophilization) of which 4 g were obtained. The sodium salt was purified by column chromatography on HP-20

(eluting with water, water/acetone (95:5) and water/acetone (9:1)).

2.3 g of the sodium salt of (S)-[1-[[[[3-(3,4-dihydroxybenzoyl)-2-oxo-1-imidazolidinyl]sulfonyl]amino]carbonyl]-2-oxo-3-azetidinyl]carbamic acid, phenylmethyl ester was obtained, which was converted to (S)-[1-[[[[3-(3,4-dihydroxybenzoyl)-2-oxo-1-imidazolidinyl]sulfonyl]amino]carbonyl]-2-oxo-3-azetidinyl]carbamic acid, phenylmethyl ester (by dissolution in water, acidification, extraction with ethyl acetate, evaporation and treatment with ether; yield was 2.1 g.

(D)
(S)-3-Amino-N-[[3-(3,4-dihydroxybenzoyl)-2-oxo-1-imidazolidinyl]sulfonyl]-2-oxo-1-azetidinecarboxamide, trifluoroacetate salt (S)-[1-[[[[3-(3,4-Dihydroxybenzoyl)-2-oxo-1-imidazolidinyl]sulfonyl]amino]carbonyl]-2-oxo-3-azetidinyl]carbamic acid, phenylmethyl ester (2.1 g, 0.004 mol) was added to a stirred mixture formed from 10 ml of trifluoroacetic acid and 2.5 ml of thioanisole. The mixture was stirred overnight at room temperature, evaporated in vacuo and the solid residue triturated with ether to yield 2.1 g of crude (S)-3-amino-N-[[3-(3,4-dihydroxybenzoyl)-2-oxo-1-imidazolidinyl]sulfonyl]-2-oxo-1-azetidinecarboxamide, trifluoroacetate salt.

(E)
[3S(Z)]-2-[[[1-(2-Amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (Z)-2-Amino-α-[[1-(diphenylethoxycarbonyl)-1-methylethoxy]imino]-4-thiazoleacetic acid (0.88 g) was dissolved in 20 ml of dimethylformamide, 0.30 ml of triethylamine was added, and after cooling to −30° C., 0.42 ml of diphenylchlorophosphate was added. The mixture was stirred for 1 hour at −30° C. To the mixture was added 1.1 g of (S)-3-amino-N-[[3-(3,4-dihydroxybenzoyl)-2-oxo-1-imidazolidinyl]sulfonyl]-2-oxo-1-azetidinecarboxamide, trifluoroacetate salt followed by 0.30 ml of triethylamine and 10 ml of dimethylformamide. The reaction mixture was stirred at −10° C. for 2 hours and at 0° C. for 1 hour. The solvent was evaporated in vacuo and the residue was triturated with ether; the residue solidified slowly. The crude material was suspended in water, the pH of the suspension was adjusted to 3.5. After filtration and drying, 1.6 g of crude [3S(Z)]-2-[[[1-(2-amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester was obtained.

(F)
[3S(Z)]-2-[[[1-(2-Amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, disodium salt Crude [3S(Z)]-2-[[[1-(2-amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (1.6 g) was suspended in 4 ml of anisole. At −10° C., 20 ml of trifluoroacetic acid was dropped into the suspension and the mixture was stirred at −10° C. for 1 hour. Crude [3S(Z)]-2-[[[1-(2-amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid was precipitated by the addition of ether at −10° C., yielding 1 g.

The crude was converted to the sodium salt (water/acetone:sodium bicarbonate, pH 6) and purified by column chromatography on HP-20 (eluting with water), yielding 130 mg of pure [3S(Z)]-2-[[[1-(2-amino-4-thiazolyl)-2-[[1-[[[[3-(3,4-dihydroxybenzoyl)-2-oxo-1-imidazolidinyl]sulfonyl]amino]carbonyl]-2-oxo-3-azetidinyl]amino]-2-oxoethylidene]amino]oxy]-2-methylpropanoic acid, disodium salt.

EXAMPLE 6

[3S(Z)]-2-[[[1-(2-Amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]acetic acid, disodium salt (A)
(S)-3-Amino-N-[[2-(3,4-dihydroxybenzoyl)hydrazino]sulfonyl]-2-oxo-1-azetidinecarboxamide 7.4 ml of bis(trimethylsilyl)acetamide (0.03 mol) was added to a suspension of 2.47 g (0.005 mol) of (S)-[1-[[[[2-(3,4-dihydroxybenzoyl)hydrazino]sulfonyl]amino]carbonyl]-2-oxo-3-azetidinyl]carbamic acid, phenylmethyl ester (see Example 3A) in 40 ml of acetonitrile. After stirring for 15 minutes, a clear solution was obtained. One gram of palladium on charcoal (10%) was added and hydrogen was passed through the solution with stirring. The catalyst was filtered off and 2 ml of methanol were added to the solution, followed by a few drops of acetic acid. The mixture was stirred for 2 hours with cooling (ice/water) and the precipitate was filtered off, washed with acetonitrile and petroleum ether to yield 1.5 g of (S)-3-amino-N-[[2-(3,4-dihydroxybenzoyl)hydrazino]sulfonyl]-2-oxo-1-azetidinecarboxamide.

(B)
[3S(Z)]-2-[[[1-(2-Amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]acetic acid, diphenylmethyl ester (Z)-2-Amino-α-[[(diphenylmethoxycarbonyl)methoxy]imino]-4-thiazoleacetic acid (1.65 g, 0.004 mol) was dissolved in 40 ml of anhydrous dimethylformamide, 1.7 ml of triethylamine (0.012 mol) was added and, after cooling to −30° C., 0.88 ml of diphenylchlorophosphate was added with stirring. The mixture was stirred at −30° C. for 1 hour. 1.43 g (0.004 mol) of (S)-3-amino-N-[[2-(3,4-dihydroxybenzoyl)hydrazino]sulfonyl]-2-oxo-1-azetidinecarboxamide was added followed by 5 ml of dimethylformamide and 0.56 ml of triethylamine (0.004 mol). The reaction mixture was stirred for 2 hours at −10° C. and for 1 hour at 0° C. The dimethylformamide was removed in vacuo and the residue stirred overnight with ether. It solidified to yield 5.3 g of material which was treated with 250 ml of water and 250 ml of ethyl acetate. The pH of the mixture was adjusted to 2–2.5 by the addition of 2N hydrochloric acid. The insoluble material was filtered off yielding 1.1 g of crude [3S(Z)]-2-[[[1-(2-amino-4-thiazolyl)-2-[[1-[[[[2-(3,4-dihydroxybenzoyl)hydrazino]sulfonyl]amino]carbonyl]-2-oxo-3-azetidinyl- ]amino]-2-oxoethylidene]amino]oxy]acetic acid, diphenylmethyl ester.

(C)
[3S(Z)]-2-[[[1-(2-Amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]acetic acid, disodium salt To a suspension of 1.1 g of [3S(Z)]-2-[[[1-(2-amino-4-thiazolyl)-2-[[1-[[[[2-(3,4-dihydroxy-benzoyl)hydrazino]sulfonyl]amino]carbonyl]-2-oxo-3-azetidinyl]amino]-2-oxoethylidene]amino]oxy]acetic acid, diphenylmethyl ester in 2.2 ml of anisole was added 11 ml of trifluoroacetic acid at −10° C. The mixture was stirred at −10° C. for 1 hour. Then, at the same temperature, 60 ml of ether was added to precipitate [3S(Z)]-2-[[[1--(2-amino-4-thiazolyl)-2-[[1-[[[[2-(3,4-dihydroxybenzoyl)hydrazino]sulfonyl]amino]carbonyl]-2-oxo-3-azetidinyl]amino]-2-oxoethylidene]amino]oxy]acetic acid, trifluoroacetate salt (yield: 0.7 g). The crude material was converted to the sodium salt (acetone/water; sodium bicarbonate→pH 6) which was purifed by HP-20 column chromatography (eluting with water).

EXAMPLE 7

2-[[[1-(2-Amino-4-thiazolyl)-2-[[1-[[[[2-[(3,4-dihydroxybenzylidene)amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt (A)
1-[[(3,4-Dihydroxyphenyl)methylene]amino]-2-imidazolidinone To a solution of 61.4 g (0.446 mol) of 1-amino-2-imidazolidinone hydrochloride in 300 ml of 80% aqueous ethanol were added 223 ml of 2N sodium hydroxide (0.446 mol) and a solution of 61.6 g (0.446 mol) of 3,4-dihydroxybenzaldehyde in 300 ml of 80% aqueous ethanol. The mixture was stirred for 20 minutes at room temperature, and the precipitate filtered off by suction, washed with ethanol and dried in vacuo (yield: 34.5 g; melting point 257° C., dec).

(B)
1-[[[3,4-Bis[(trimethylsilyl)oxy]phenyl]methylene]amino]-3-(trimethylsilyl)-2-imidazolidinone To a mixture of 5.0 g (22.6 mmol) of 1-[[(3,4-dihydroxyphenyl)methylene]amino]-2-imidazolidinone and 8.1 g (74.6 mmol) of chlorotrimethylsilane in 200 ml of ethyl acetate was added 7.5 g (74.6 mmol) of triethylamine. After stirring overnight at ambient temperature, the precipitate was filtered off and the filtrate evaporated in vacuo to afford 8.8 g of 1-[[[3,4-bis[(trimethylsilyl)oxy]phenyl]methylene]amino]-3-(trimethylsilyl)-2-imidazolidinone.

(C)
(S)-[1-[[[[3-[[(3,4-Dihydroxyphenyl)methylene]amino]-2-oxo-1-imidazolidinyl]sulfonyl]amino]carbonyl]-2-oxo-3-azetidinyl]carbamic acid, phenylmethyl ester, monosodium salt To a suspension of 4.37 g (19.9 mmol) of (S)-(2-oxo-3-azetidinyl)carbamic acid, phenylmethyl ester in 100 ml of ethyl acetate were added 2.81 g (19.9 mmol) of chlorosulfonyl isocyanate and the mixture was stirred for one hour at room temperature. The resulting solution was cooled to 0° C., and a solution of 8.7 g (19.9 mmol) of 1-[[[3,4-bis[(trimethylsilyl)oxy]phenyl]methylene]amino]-3-(trimethylsilyl)-2-imiazolidinone and 3.96 g of N-methyl-N-(trimethylsilyl)trifluoroacetamide (19.9 mol) in 50 ml of ethyl acetate was added dropwise. The reaction mixture was stirred overnight at ambient temperature, washed twice with brine, dried with sodium sulfate and evaporated in vacuo. The residue was dissolved in methanol/water and the pH adjusted to 6.5 by adding 1N sodium hydroxide. After evaporation of the methanol, the aqueous solution was freeze-dried (yield: 9.3 g; melting point 180° C., dec).

(D)
[3S(Z)]-2-[[[1-(2-Amino-4-thiazolyl)-2-[[1-[[[[3-[[(3,4--dihydroxyphenyl)methylene]amino]-2-oxo-1-imidazolidinyl]sulfonyl]amino]carbonyl]-2-oxo-3-azetidinyl]amino]-2-oxoethylidene]amino]-oxy]-2-methylpropanoic acid, diphenylmethyl ester, monosodium salt To a solution of 4.0 g (7 mmol) of (S)-[1-[[[[3-[[(3,4-dihydroxyphenyl)methylene]amino]-2-oxo-1-imidazolidinyl]sulfonyl]amino]carbonyl]-2-oxo-3-azetidinyl]carbamic acid, phenylmethyl ester, monosodium salt in 70 ml of dimethylformamide was added 2 g of palladium on charcoal (10%), and hydrogen was bubbled through the mixture for four hours at room temperature. The catalyst was filtered off, and the filtrate added to a solution of 3.1 g (7 mmol) of (Z)-2-amino-α-[[1-(diphenylmethoxycarbonyl)-1-methylethoxy]imino]-4-thiazoleacetic acid, 0.11 g (0.7 mmol) of N-hydroxybenzotriazole and 1.6 g (7.7 mmol) of dicyclohexylcarbodiimide in 50 ml of dimethylformamide. After stirring overnight at room temperature, dicyclohexylurea was filtered off by suction and the filtrate evaporated in vacuo. The residue was washed with ether and purified by column chromatography on HP-20 (yield:1.3 g; melting point 185° C., dec).

(E)
2-[[[1-(2-Amino-4-thiazolyl)-2-[[1-[[[[2-[(3,4-dihydroxybenzylidene)amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt 1.19 g (1.39 mmol) of [3S(Z)]-2-[[[1-(2-amino-4-thiazolyl)-2-[[1-[[[[3-[[(3,4-dihydroxy-phenyl)methylene]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt was dissolved in 10 ml of anisole and cooled to 0° C. 20 ml of trifluoroacetic acid was added dropwise, and after stirring for one hour at 0° C., the mixture was stirred into 1 liter of ether-petroleum ether 1:1. The precipitate was filtered off by suction and dried in vacuo (0.8 g).

The resulting substance was dissolved in methanol/water and the pH adjusted to 6.5 by adding 0.1N sodium hydroxide. Methanol was evaporated in vacuo and the aqueous solution freeze-dried to afford 0.8 g of crude product which was purified by column chromatography on HP-20 (eluting with water) to yield 0.15 g of the title compound, melting point 259° C., dec.

EXAMPLE 8

2-[[[1-(2-Amino-4-thiazolyl)-2-[[1-[[[[3-[(2-carboxy-4,5-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt (A) 1-[(t-Butoxycarbonyl)amino]-2-imidazolidinone A mixture of 20.6 g (150 mmol) of 1-amino-2-imidazolidinone hydrochloride, 29.2 g (157 mmol) of tributylamine and 103 g (473 mmol) of dicarbonic acid, bis(1,1-dimethylethyl ester was stirred at 100° C. overnight. After cooling, the mixture was evaporated in vacuo and the residue recrystallized from ethyl acetate, yielding 19.67 g of 1-[(t-butoxycarbonyl)amino]-2-imidazolidinone which was purified by column chromatography on silica gel with ethyl acetate as eluent.

(B) 1-[(t-Butoxycarbonyl)amino]-3-(trimethylsilyl)-2-imidazolidinone

While cooling, 10.55 g (97.1 mmol) of trimethylsilylchloride was dropped into a solution of 19.55 g (97.1 mmol) of 1-[(t-butoxycarbonyl)amino]-2-imidazolidinone and 9.83 g (97.1 mmol) of triethylamine in 900 ml of absolute ethyl acetate. After stirring overnight, the salt was filtered off and the filtrate evaporated in vacuo to yield 24.18 g of 1-[(t-butoxycarbonyl)amino]-3-(trimethylsilyl)-2-imidazolidinone, melting point 132.1° C.

(C) (S)-[1-[[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt 6.13 g (43.3 mmol) of chlorosulfonyl isocyanate was added to a solution of 8.65 g (39.3 mmol) of (S)-(2-oxo-3-azetidinyl)carbamic acid, phenylmethyl ester in 500 ml of absolute ethyl acetate. After stirring for 30 minutes, 11.83 g (43.3 mmol) of 1-[(6-butoxycarbonyl)amino]-3-(trimethylsilyl)-2-imidazolidinone was added. The mixture was stirred overnight and extracted three times with water. After drying, the ethyl acetate was removed in vacuo. The residue was dissolved in water/methanol 1:1 and the pH adjusted to 6.5 with 1N sodium hydroxide. When the methanol was distilled off in vacuo, (S)-[1-[[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt precipitated from the solution. The product was filtered off, washed with water and dried in vacuo, yielding 8.0 g. The filtrate was evaporated to dryness and the residue (14.7 g) triturated with a small amount of water, yielding 4.4 g. Freeze drying of the mother liquor afforded 7.27 g of crude product. The total yield of (S)-[1-[[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt was 12.4 g, melting point 196°-225° C.

(D) [3S(Z)]-2-[[[1-(2-amino-4-thiazolyl)-2-[[1-[[[[3-[[(1,1-dimethylethoxy)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt 2.42 g (5.5 mmol) of (Z)-2-amino-α-[[1-(diphenylmethoxycarbonyl)-1-methylethoxy]imino]4-thiazoleacetic acid, 0.84 g (5.5 mmol) of N-hydroxybenzotriazole and 1.7 g (8.25 mmol) of dicyclohexylcarbodiimide were dissolved in 50 ml of absolute dimethylformamide and stirred for 30 mintues. (Solution A)

3.20 g (5.5 mmol) of (S)-[1-[[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt was dissolved in 100 ml of absolute dimethylformamide and 1.5 g of palladium on charcoal was added. Hydrogen was bubbled through the solution for 40 minutes. The catalyst was filtered off and the filtrate was added dropwise to solution A.

After stirring overnight, dicyclohexylurea was filtered off, the solvent evaporated in vacuo and the residue triturated with ether to afford 4.86 g of crude product. This material was dissolved in acetone/water and the pH corrected to 6.5. When acetone was distilled off in vacuo, a gummy precipitate separated. The mother liquor was decanted and freeze-dried to yield 2.92 g of pure [3S(Z)]-2-[[[1-(2-amino-4-thiazolyl)-2-[[1-[[[[3-[[(1,1-dimethylethoxy)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt.

(E) [3S(Z)]-2-[[[2-[[1-[[[(3-Amino-2-oxo-1-imidazolidinyl)sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt 2.8 g (3.35 mmol) of [3S(Z)]-2-[[[1-(2-amino-4-thiazolyl)-2-[[1-[[[[3-[[(1,1-dimethylethoxy)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt was suspended in 6.4 ml of anisole and, at −10° C., 12.8 ml of trifluoroacetic acid was added dropwise. After stirring for 2 hours at 0° C., 100 ml of ether was added and the precipitate was collected by filtration and dried in vacuo (2.76 g). The crude product was dissolved in water/methanol, and the pH adjusted to 6.5 with 1N potassium hydroxide. Evaporation of the methanol and freeze-drying yielded 3.0 g of crude product which was dissolved in water and chromatographed on XAD under mplc-conditions with water as eluent to yield 0.59 g (0.95 mmol). of [3S(Z)]-2-[[[2-[[1-[[[(3-amino-2-oxo-1-imidazolidinyl)sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt.

(F)

2-[[[1-(2-Amino-4-thiazolyl)-2-[[1-[[[3-[(2-carboxy-4,5-dihydroxybenzoyl)amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt 0.17 g (0.95 mmol) of β,β-dihydroxyphthalic anhydride was added to a solution of 0.56 g (0.95 mmol) of [3S(Z)]-2-[[[2-[[1-[[[(3-amino-2-oxo-1-imidazolidinyl)-sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt in 10 ml of absolute dimethylformamide. The bright yellow solution was stirred overnight and then an additional 17 mg of β,β-dihydroxyphthalic anhydride was added. After 4 hours, the dimethylformamide was evaporated in vacuo, the residue dissolved in water and the pH brought to 6.5 with 1N potassium hydroxide. After freeze-drying the solution, the crude product (0.87 g) was chromatographed on XAD-2 under mplc-conditions with water as eluent. The freeze-dried fractions yielded 0.25 g of the title compound, melting point 240°–265° C.

EXAMPLE 9

[2S-[2α,3β(Z)]]-2-[[[1-(2-Amino-4-thiazolyl)-2-[[1-[[[[4-[(3,4-dihydroxybenzoyl)amino]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt (A)
3,4-bis(Acetyloxy)-N-(2,3-dioxo-1-piperazinyl)benzamide To a solution of 7.0 g (54.2 mmol) of 1-amino-2,3-piperazinedione in 140 ml of water were added 140 ml of tetrahydrofuran and dropwise a filtered solution of 27.9 g (108.4 mmol) of 3,4-bis(acetyloxy)benzoyl chloride in 140 ml of tetrahydrofuran at room temperature. After 2 hours, 6.0 g (59.4 mmol) of triethylamine was added dropwise and after stirring for 20 hours, the resulting crystals were filtered off, washed with water/tetrahydrofuran 1:1 and dried in vacuo (60° C.); yield: 10.9 g; melting point 210°–212° C.

When the mother liquor was concentrated to a third of its volume, a mixture of 3,4-bis(acetyloxy)-N-(2,3-dioxo-1-piperazinyl)benzamide and diacetoxybenzoic acid precipitated (15.7 g). This mixture was stirred for 6 hours with 150 ml of 1N sodium bicarbonate solution, filtered, washed with water and dried in vacuo to yield 4.3 g of 3,4-bis(acetyloxy)-N-(2,3-dioxo-1-piperazinyl)-benzamide.

(B)
N-(3,4-Dihydroxyphenylcarbonylamino)piperazindione

To a suspension of 12.13 g (34.7 mmol) of 3,4-bis-(acetyloxy)-N-(2,3-dioxo-1-piperazinyl)benzamide in 290 ml of methanol and 80 ml of water was added 29 ml of 25N potassium hydroxide solution (72.9 mmol), and the mixture was stirred for 1 hour at room temperature. The pH of the solution was brought to 6.9 with dilute hydrochloric acid, the solution was then concentrated to 100 ml and the precipitate filtered off, washed with water and dried in vacuo (60°–70° C.); yield: 7.85 g, melting point 294° C.

(C)
(S)-1-[[[[4-[(3,4-Dihydroxybenzoyl)amino]-2,3-dioxo-1-piperazinyl]sulfonyl]amino]carbonyl]-2-oxo-3-azetidinyl]carbamic acid, phenylmethyl ester To a suspension of 1.90 g (7.16 mmol) of N-(2,3-dioxo-1-piperazinyl)-3,4-dihydroxybenzamide in 30 ml of absolute ethyl acetate was added 5.70 g (28.64 mmol) of N-methyl-N-(trimethylsilyl)trifluoroacetamide, and the mixture was stirred for 3 hours at 60° C. The clear solution was evaporated to dryness and the crystalline residue suspended in 30 ml of ethyl acetate (solution A).

To a suspension of 1.58 g (7.16 mmol) of (S)-(2-oxo-3-azetidinyl)carbamic acid, phenylmethyl ester in 50 ml of ethyl acetate was added 1.01 g (7.16 mmol) of chlorosulfonyl isocyanate. After stirring for 1 hour at room temperature, the solution was cooled to 0° C. and 24 ml of dichloromethane and 2.17 g (21.48 mmol) of triethylamine were added (solution B).

To solution B, solution A was added dropwise at 0° C. After stirring overnight, ice was added and the pH brought to 1 with 3N hydrochloric acid. After stirring for 3 hours, the phases were separated.

The organic phase was washed with water and the aqueous phase back-extracted two times with ethyl acetate.

The combined organic phases were dried and evaporated to afford 3.0 g of crude material which was triturated with ether to yield 2.94 g of (S)-[1-[[[[4-[(3,4-dihydroxybenzoyl)amino]-2,3-dioxo-1-piperazinyl]sulfonyl]amino]carbonyl]-2-oxo-3-azetidinyl]carbamic acid, phenylmethyl ester.

(D)
(S)-3-Amino-N-[[4-[(3,4-dihydroxybenzoyl)amino]-2,3-dioxo-1-piperazinyl]sulfonyl]-2-oxo-1-azetidinecarboxamide, trifluoroacetate salt To a mixture of 12 ml of trifluoroacetic acid and 3 ml of thioanisole was added 2.92 g (4.94 mmol) of (S)-[1-[[[[4-[(3,4-dihydroxybenzoyl)amino]-2,3-dioxo-1-piperazinyl]sulfonyl]amino]carbonyl]-2-oxo-3-azetidinyl]carbamic acid, phenylmethyl ester at 0° C. After stirring overnight at 10° C., 150 ml of ether was added and the resulting precipitate was filtered off, washed with ether and dried in vacuo. For further purification, the salt was triturated two times with dichloromethane; yield: 2.56 g; melting point 206°–210° C.

(E)
[2S-[2α,3β(Z)]]-2-[[[1-(2-Amino-4-thiazolyl)-2-[[1-[-[[[4-[(3,4-dihydroxybenzoyl)amino]-2,3-dioxo-1-piperazinyl]sulfonyl]amino]carbonyl]-2-oxo-3-azetidinyl]amino]-2-oxoethylidene]amino]oxy]-2-methylpropanoic acid, diphenylmethyl ester To a solution of 1.94 g (4.42 mmol) of (Z)-2-amino-α-[[1-(diphenylmethoxycarbonyl)-1-methylethoxy]amino]-4-thiazoleacetic acid and 1.34 g (8.84 mmol) of triethylamine in 45 ml of absolute dimethylformamide was added dropwise at −30° C. and under nitrogen protection 1.19 g (4.42 mmol) of diphenylchlorophosphate. After stirring for 1 hour, a solution of 2.52 g (4.42 mmol) of (S)-3-amino-N-[[4-[(3,4-dihydroxybenzoyl)amino]-2,3-dioxo-1-piperazinyl]sulfonyl]-2-oxo-1-azetidinecarboxamide, trifluoroacetate salt in 18 ml of dimethylformamide and subsequently 0.90 g (8.84 mmol) triethylamine were added. After stirring for 2 hours at −10° C. and an additional hour at 0° C., the dimethylformamide was evaporated in vacuo and to the residue were added 36 ml of ice water and 72 ml of ethyl acetate. When the pH was adjusted to 1.7 with hydrochloric acid, an oil separated which was isolated and triturated twice with acetone to afford crude crystalline product (1.38 g). Evaporation of the acetone mother liquors and trituration of the residue with ether yielded another 1.37 g of crude title compound; yield: 2.75 g; melting point 191°–195° C.

(F)

[2S-[2α,3β(Z)]]-2-[[[1-(2-Amino-4-thiazolyl)-2-[[1-[-[[[4-[(3,4-dihydroxybenzoyl)amino]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt To a suspension of 1.33 g (1.51 mmol) of [2S-[2α,3β(Z)]]-2-[[[1-(2-amino-4-thiazolyl)-2-[[1-[[[[4-[(3,4-dihydroxybenzoyl)amino]-2,3-dioxo-1-piperazinyl]sulfonyl]amino]carbonyl]-2-oxo-3-azetidinyl]amino]-2-oxoethylidene]amino]oxy]-2-methylpropanoic acid, diphenylmethyl ester in 2.6 ml of anisole was added dropwise at 0° C., 13 ml of trifluoroacetic acid. After stirring for 1.5 hours, the excess trifluoroacetic acid was distilled off in vacuo. Ether was added to the residue and the resulting crystalline material was filtered off, washed with ether and dried in vacuo (1.07 g). 1.39 g of this crude material was dissolved in 40 ml of acetone/water 1:1 and the pH adjusted to 6.5 with 1N sodium hydroxide. The freeze-dried product was dissolved in 10 ml of water and chromatographed on HP-20 with water as eluent. Yield of freeze-dried product was 0.65 g; melting point 255° C. dec.

EXAMPLE 10

[3S(Z)]-2-[[[1-(2-Amino-4-thiazolyl)-2-[[1-[[[[(2-carboxy-4,5-dihydroxyphenyl)amino]sulfonyl]amino]-2-oxo-3-azetidinyl]amino]-2-oxoethylidene]amino]oxy]-2-methylpropanoic acid, trisodium salt (A) 2-Amino-4,5-dihydroxybenzoic acid 2-Amino-4,5-dimethoxybenzoic acid (9.86 g, 0.05 mol) was mixed with 250 ml of aqueous hydrobromic acid and the mixture was refluxed for 3 hours, evaporated in vacuo and treated with ether to yield 13.3 g of the crude hydrochloride of 2-amino-4,5-dihydroxybenzoic acid. This material was dissolved in a small amount of ice water and the pH of the solution was adjusted to 4 by the addition of sodium bicarbonate solution, precipitating 2-amino-4,5-dihydroxybenzoic acid; yield: 5.4 g; melting point 245° C., dec.

(B)

(S)-4,5-Dihydroxy-2-[[[[[2-oxo-3-[[(phenylmethoxy)carbonyl]amino]-1-azetidinyl]carbonyl]amino]sulfonyl]amino]benzoic acid To a suspension of 1.76 g (0.008 mol) of (S)-(2-oxo-3-azetidinyl)carbamic acid, phenylmethyl ester in 80 ml of ethyl acetate was added 0.7 ml (0.008 mol) of chlorosulfonyl isocyanate at room temperature for 1 hour to yield a solution of (S)-[1-[[(chlorosulfonyl)amino]carbonyl]-2-oxo-3-azetidinyl]carbamic acid, phenylmethyl ester. The solution was cooled to 0° C. and a solution of silylated 2-amino-4,5-dihydroxybenzoic acid, prepared from 1.35 g (0.008 mol of 2-amino-4,5-dihydroxybenzoic acid in 80 ml of ethyl acetate by the addition of 4.45 ml (0.024 mol) of N-methyl-N-(trimethylsilyl)trifluoroacetamide and warming to 50° C. for 60 minutes, was added dropwise. The reaction mixture was stirred overnight at room temperature. Then ice water (~200 ml) was added and stirring was continued for an additional 30 minutes. The two phases were separated, the aqueous phase was layered with ethyl acetate and acidified to pH 2 (2N hydrochloric acid). The organic phase was dried and evaporated. On treatment with ether, 2.4 g of a solid residue was obtained.

(C)

(S)-2-[[[[(3-Amino-2-oxo-1-azetidinyl)carbonyl]amino]sulfonyl]amino]-4,5-dihydroxybenzoic acid 4 Grams (0.008 mol) of (S)-4,5-dihydroxy-2-[[[[[2-oxo-3-[[(phenylmethoxy)carbonyl]amino]-1-azetidinyl]carbonyl]amino]sulfonyl]amino]benzoic acid was added at 10° C. to a stirred mixture of 3.2 ml of thioanisole and 14 ml of trifluoroacetic acid. The mixture was stirred overnight at 10° C., evaporated and treated with ether to yield 4.6 g of crude (S)-2-[[[[(3-amino-2-oxo-1-azetidinyl)carbonyl]amino]sulfonyl]amino]-4,5-dihydroxybenzoic acid.

(D)

[3S(Z)]-2-[[[1-(2-Amino-4-thiazolyl)-2-[[1-[[[[(2-carboxy-4,5-dihydroxyphenyl)amino]sulfonyl]amino]-2-oxo-3-azetidinyl]amino]-2-oxoethylidene]amino]oxy]-2-methylpropanoic acid, diphenylmethyl ester To a solution of 3.52 g (0.008 mol) of (Z)-2-amino-α-[[1-(diphenylmethoxycarbonyl)-1-methylethoxy]imino]-4-thiazoleacetic acid in 80 ml of dimethylformamide was added 3.3 ml (0.024 mol) of triethylamine under a nitrogen atmosphere. After cooling to −30° C., 2.29 g (0.008 ml) of diphenylchlorophosphate was added dropwise and the mixture was stirred at −30° C. for 1 hour. Then, at the same temperature, 3.3 ml (0.024 mol) of triethylamine was added, followed by 0.008 mol of (S)-2-[[[[(3-amino-2-oxo-1-azetidinyl)carbonyl]amino]sulfonyl]amino]-4,5-dihydroxybenzoic acid (crude material from preceding step). The mixture was stirred at −10° C. for 2 hours and at 0° C. for 1 hour. The solvent was removed in vacuo and the remaining syrup treated with 80 ml of ethyl acetate and 40 ml of ice water and the pH of the mixture adjusted to 1.5–2 by the addition of 2N hydrochloric acid. The two phases were separated and the aqueous phase was washed two times with 50 ml of ethyl acetate each. The combined organic phases were washed with water, dried (magnesium sulfate) and evaporated to a volume of ca. 40 ml. Addition of ether (200 ml) precipitated the title compound in crude form; yield: 6.2 g.

(E)

[3S(Z)]-2-[[[1-(2-Amino-4-thiazolyl)-2-[[1-[[[[(2-carboxy-4,5-dihydroxyphenyl)amino]sulfonyl]amino]-2-oxo-3-azetidinyl]amino]-2-oxoethylidene]amino]oxy]-2-methylpropanoic acid, trisodium salt To a suspension of 6.2 g of crude [3S(Z)]-2-[[[1-(2-amino-4-thiazolyl)-2-[[1-[[[[(2-carboxy-4,5-dihydroxyphenyl)amino]sulfonyl]amino]-2-oxo-3-azetidinyl]amino]-2-oxoethylidene]amino]oxy]-2-methylpropanoic acid, diphenylmethyl ester in 12.4 ml of anisole, cooled to −10° C., was added 62 ml of trifluoroacetic acid. The mixture was stirred at −10° C. for 1 hour. Then, at the same temperature, 250 ml of ether was added to precipitate 4 g of [3S(Z)]-2-[[[1-(2-amino-4-thiazolyl)-2-[[1-[[[[(2-carboxy-4,5-dihydroxyphenyl)amino]sulfonyl]amino]-2-oxo-3-azetidinyl]amino]-2-oxoethylidene]amino]oxy]-2- methylpropanoic acid, trifluoroacetate salt. The crude salt was dissolved in a mixture of 50 ml of water and 20 ml of acetone, and the pH was adjusted to 5.5 by the addition of sodium bicarbonate solution (ice cooling). The acetone was removed in vacuo and the aqueous solution lyophilized to yield 3.2 g of crude title compound, which was purified by chromatography on HP-20 (900×25, elution with water, 12 ml fractions); yield: 0.3 g.

EXAMPLE 11

[[[[[(S)-3-[[(Z)-(2-Amino-4-thiazolyl)][(2-carboxy-2-methylethoxy)imino]acetyl]amino]-2-oxo-1-azetidinyl]-carbonyl]amino]sulfonyl]amino]-3,4-dihydroxybenzeneacetic acid, trisodium salt (A) 3,4-Dihydroxy-α-[[[[(S)-2-oxo-3-[[(phenylmethoxy)carbonyl]amino]-1-azetidinyl]carbonyl]amino]sulfonyl]benzeneacetic acid, disodium salt 28.0 ml (0.144 mol) of N-methyl-N-trimethylsilyltrifluoroacetamide was added to a suspension of 5.50 g (0.030 mol) of 3,4-dihydroxyphenylglycine in 90 ml of dry acetonitrile. Within 5 minutes, a clear brown solution was obtained and the temperature raised to 40° C. After stirring for an additional 10 minutes at this temperature, the solution was evaporated in vacuo and the oily residue was redissolved in 90 ml of dry ethyl acetate (solution A).

To a suspension of 6.61 g (0.030 mol) of (S)-(2-oxo-3-azetidinyl)carbamic acid, phenylmethyl ester in 240 ml of dry ethyl acetate, 2.62 ml (0.030 mol) of chlorosulfonyl isocyanate was added and the mixture was stirred for 1 hour at room temperature to form a solution of (S)-[1-[[(chlorosulfonyl)amino]carbonyl]-2-oxo-3-azetidinyl]carbamic acid, phenylmethyl ester. After cooling to 0° C., a solution of 12.54 ml (0.090 mol) of triethylamine in 60 ml of dry dichloromethane was dropped in, followed by the dropwise addition of the freshly prepared solution A (0° C.). Overnight the mixture was stirred well at room temperature, then poured into ice water and acidified to pH 2 by the addition of 1N hydrochloric acid. The two phases was separated and the aqueous phase was extracted twice with ethyl acetate. 200 ml of ice water were added to the combined organic phases and the pH of the mixture was adjusted to pH 6.5 by the addition of 1N sodium hydroxide. The aqueous phase was separated, washed again with ethyl acetate, concentrated in vacuo and finally freeze dried; yield: 13.11 g.

(B) [[[[(S)-3-[[(Z)-(2-Amino-4-thiazolyl)][(2-carboxy-2-methylethoxy)imino]acetyl]amino]-2-oxo-1-azetidinyl]-carbonyl]amino]sulfonyl]amino]-3,4-dihydroxybenzeneacetic acid, diphenylmethyl ester A solution of 13.07 g (23.7 mmol) of 3,4-dihydroxy-α-[[[[(S)-2-oxo-3-[[(phenylmethoxy)carbonyl]amino]-1-azetidinyl]carbonyl]amino]sulfonyl]benzeneacetic acid, disodium salt in 160 ml of dry dimethylformamide was added to a suspension of 2.10 g of 10% palladium on charcoal in 60 ml of dry dimethylformamide, and hydrogen was bubbled through the mixture at 20° C. for 20 minutes. The catalyst was removed by filtration and washed with 30 ml of dry dimethylformamide.

Into a solution of 10.40 g (23.7 mmol) of (Z)-2-amino-α-[[1-(diphenylmethoxycarbonyl)-1-methylethoxy]imino]-4-thiazoleacetic acid in 200 ml of dry dimethylformamide, 9.89 ml (23.7 mmol) of triethylamine was dropped with cooling to −30° C., followed by the dropwise addition of 4.90 ml (23.7 mmol) diphenyl-chlorophosphate. After stirring at −30° C. for 90 minutes, the above prepared filtrate was added dropwise at −30° C. and the mixture was stirred at −10° C. for 2 hours and at 0° C. overnight. After the removal of the solvent in vacuo, the residue was taken up in ice cold buffer solution (pH 2, citrate) and ethyl acetate and acidified to pH 2 by the addition of 2N hydrochloric acid. An insoluble dark tar was removed by suction and the organic phase of the filtrate was separated, washed with 0.01N hydrochloric acid (pH 2), dried (magnesium sulfate) and evaporated in vacuo. The oily residue (24.5 g) became crystalline by repeated stirring with ether containing a trace of ethyl acetate, yield: 11.53 g. This crude material was used in the next step without further purification.

(C) [[[[[(S)-3-[[(Z)-(2-Amino-4-thiazolyl)][(2-carboxy-2-methylethoxy)imino]acetyl]amino]-2-oxo-1-azetidinyl]-carbonyl]amino]sulfonyl]amino]-3,4-dihydroxybenzeneacetic acid, trisodium salt To a suspension of 10.83 g (13.6 mmol) of the crude [[[[[(S)-3-[[(Z)-(2-amino-4-thiazolyl)][(2-carboxy-2-methylethoxy)imino]acetyl]amino]-2-oxo-1-azetidinyl]-carbonyl]amino]sulfonyl]amino]-3,4-dihydroxybenzeneacetic acid, diphenylmethyl ester in 45 ml of dry dichloromethane at −10° C., a cold solution of 11 ml of anisole in 110 ml of trifluoroacetic acid was added. After being stirred at 0° C. for 10 minutes, the clear solution was evaporated in vacuo at 0°–5° C. and the residue was treated with dry ether. The solid was collected by suction, washed with dry ether, dried in vacuo to give 7.28 g of impure [[[[[(S)-3-[[(Z)-(2-amino-4-thiazolyl)][(2-carboxy-2-methylethoxy)imino]acetyl]amino]-2-oxo-1-azetidinyl]carbonyl]amino]sulfonyl]amino]-3,4-dihydroxybenzeneacetic acid, trifluoroacetate salt.

This crude trifluoroacetic acid salt was taken up in ice water and ethyl acetate, and the pH of the mixture was adjusted to 6.0 by the addition of 0.5N sodium hydroxide. After stirring for 10 minutes, the aqueous phase was separated, washed with ethyl acetate and freeze dried. MPLC of this material (8.22 g) on XAD-2 eluting with water yielded, after freeze drying the appropriate fractions, 2.25 g of the title compound.

EXAMPLE 12

[3S(Z)]-2-[[[1-(2-Amino-4-thiazolyl)-2-[[1-[[[[2-[[-(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanoic acid, disodium salt (A) 4-Aminocatechol trifluoroacetate A solution of 7.76 g (50.0 mmol) of 4-nitrocatechol in 350 ml of ethyl acetate containing 38.5 ml (50.0 mmol) of trifluoroacetic acid was hydrogenated in the presence of 3.4 g of palladium (10%) on charcoal for 40 minutes. The catalyst was filtered off and the filtrate was evaporated iin vacuo to leave a residue which was stirred with dry ether, collected by suction and dried in vacuo (over potassium hydroxide); yield: 11.3 g; melting point 145°–154° C., dec.

(B)
2-[[[(3,4-Dihydroxyphenyl)amino]carbonyl]hydrazinecarboxylic acid, phenylmethyl ester 15.64 ml (80.0 mmol) of N-methyl-N-trimethylsilyltrifluoroacetamide was added to a suspension of 4.80 g (20.0 mmol) of 4-aminocatechol trifluoroacetate in 80 ml of dry acetonitrile. After stirring for 30 minutes, the dark solution was evaporated in vacuo and the dark residue was redissolved in 25 ml of dichloromethane. A solution of 4.56 g (20.0 mmol) of 2-(chlorocarbonyl)hydrazinecarboxylic acid, phenylmethyl ester in 50 ml of dichloromethane was slowly dropped in with stirring at 10° C. (40 minutes), and stirring was continued for 2 hours at room temperature. After evaporation in vacuo, the residue was taken up in a few ml of methanol and stirred until it became crystalline. The suspension was diluted with ether, and the precipitate was collected by suction; yield: 6.09 g, melting point 204° C., dec.

(C) N-(3,4-Dihydroxyphenyl)hydrazinecarboxamide, hydrochloride

A solution of 5.03 g (15.85 mmol) of 2-[[[(3,4-dihydroxyphenyl)amino]carbonyl]hydrazinecarboxylic acid, phenylmethyl ester in 250 ml of methanol containing 2.64 ml (31.70 mmol) of hydrochloric acid was hydrogenated in the presence of 0.5 g of 10% palladium on charcoal for 5 minutes. The catalyst was filtered off and the solvent was distilled off in vacuo to leave a solid which was stirred with a few ml of dry ether; yield after drying in vacuo: 3.36 g; melting point 170°-180° C., dec.

(D)
(S)-[1-[[[[2-[[(3,4-Dihydroxyphenyl)amino]carbonyl]hydrazino]sulfonyl]amino]carbonyl]-2-oxo-3-azetidinyl]carbamic acid, phenylmethyl ester 2.93 ml (15.0 mmol) of N-methyl-N-trimethylsilyltrifluoroacetamide was added to a suspension of 1.10 g (5.0 mmol) of N-(3,4-dihydroxyphenyl)hydrazinecarboxamide, hydrochloride in 10 ml of dry ethyl acetate. After stirring for 1 hour at 50° C., the clear solution was evaporated in vacuo and the residue was redissolved in 10 ml of dry ethyl acetate (solution A).

To a suspension of 1.10 g (5.0 mmol) of (S)-(2-oxo-3-azetidinyl)carbamic acid, phenylmethyl ester in 40 ml of dry ethyl acetate, 0.45 ml (5.00 mmol) of chlorosulfonyl isocyanate was added with stirring and the mixture was stirred for 1 hour at room temperature and then cooled to 0° C. After the addition of 10 ml of dry dichloromethane and 2.09 ml (15.0 mmol) of triethylamine, solution A was dropped in with stirring at 0° C. After stirring overnight at 0° C., the reaction mixture was poured into 10 ml of an ice cold buffer solution (citrate pH 2). The pH was maintained by the addition of 2N hydrochloric acid (pH=2). The organic layer was separated and the aqueous phase was extracted with ethyl acetate. The organic layers were combined, washed with brine, dried (magnesium sulfate) and evaporated in vacuo to leave a residue which became crystalline by stirring with a few ml of ethyl acetate. After diluting with dry ether, the precipitate was collected by suction, washed with ether and dried in vacuo; yield: 1.53 g, melting point 130° C. dec.

(E)
(S)-3-Amino-1-[[[[2-[[(3,4-dihydroxyphenyl)amino]carbonyl]hydrazino]sulfonyl]amino]carbonyl]-2-oxoazetidine At 0° C., 1.02 g (2.0 mmol) of (S)-[1-[[[[2-[[(3,4-dihydroxyphenyl)amino]carbonyl]hydrazino]sulfonyl]amino]carbonyl]-2-oxo-3-azetidinyl]carbamic acid, phenylmethyl ester was added to a mixture of 3.31 ml of trifluoroacetic acid and 0.78 ml (6.63 mmol) of thioanisole. After stirring overnight at room temperature, the dark brown solution was dropped into 40 ml of dry ether (0° C.) and the precipitated material was collected by suction (1.15 g) and stirred with 10 ml of dry dichloromethane; yield: 0.92 g. This material was used in the next step without further purification.

(F)
[3S(Z)]-2-[[[1-(2-Amino-4-thiazolyl)-2-[[1-[[[[2-[-[(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanoic acid, diphenylmethyl ester Into a −30° C. cold mixture of 0.66 g (1.5 mmol) of (Z)-2-amino-α-[[1-(diphenylmethoxycarbonyl)-1-methylethoxy]imino]-4-thiazoleacetic acid in 13 ml of dry dimethylformamide, 0.63 ml (4.5 mmol) of triethylamine was dropped, followed by 0.33 ml (1.5 mmol) of diphenylchlorophosphate. After stirring at −30° C. for 1 hour, 0.42 ml (3.0 mmol) of triethylamine was dropped in, followed by the addition of 0.80 g (1.5 mmol) of (S)-3-amino-1-[[[[2-[[(3,4-dihydroxyphenyl)amino]carbonyl]hydrazino]sulfonyl]amino]carbonyl]-2-oxoazetidine. The mixture was stirred for 2 hours at −10° C. and an additional 2 hours at 0° C. The solvent was removed in vacuo and the residue was taken up in a few ml of ethyl acetate and ice water. The pH of the mixture was corrected to pH=2 the addition of dilute hydrochloric acid. The insoluble material was collected by suction[1] and stirred with a few ml of ethyl acetate until it became crystalline; yield after drying in vacuo: 0.31 g. This material was used in the next step without further purification.

[1] From the organic layer of the filtrate, additional [3S(Z)]-2-[[[1-(2-amino-4-thiazolyl)-2-[[1-[[[[2-[[(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanic acid, diphenylmethyl ester was obtained. This material, however, was markedly impurer.

(G)
[3S(Z)]-2-[[[1-(2-Amino-4-thiazolyl)-2-[[1-[[[[2-[-[(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanoic acid, disodium salt To a suspension of 0.25 g (0.314 mmol) of the crude [3S(Z)]-2-[[[1-(2-amino-4-thiazolyl)-2-[[1-[[[[2-[-[(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanoic acid, diphenylmethyl ester in 1.8 ml of dry dichloromethane, 0.37 ml of anisole was added, followed by 3.7 ml of −10° C. cold trifluoroacetic acid. After stirring at 0° C. for 30 minutes, the solvent was removed in vacuo at 0° C.-5° C. The residue was taken up in a few ml of cold water and ether, and the pH was adjusted to 6.0 by the addition of dilute sodium hydroxide (1%). The aqueous phase was freeze dried (0.27 g) and then purified by MPLC on XAD-2 resin eluting with water. Freeze drying of the appropriate fractions gave 0.12 g of [3S(Z)]-2-[[[1-(2-amino-4-thiazolyl)-2-[[1-[[[[2-[-[(3,4-dihydroxyphenyl)amino]carbonyl]hydrazino]sulfonyl]amino]carbonyl]-2-oxo-3-azetidinyl]amino]-2-oxoethylidene]amino]oxy-2-methylpropanoic acid, disodium salt.

EXAMPLE 13

[3S(Z)]-2-[[[1-(2-Amino-4-thiazolyl)-2-[[1-[[[[2-[2-(3,4-dihydroxybenzoyl)hydrazino]carbonyl]hydrazino]sulfonyl]amino]carbonyl]-2-oxo-3-azetidinyl]amino]-2-oxoethylidene]amino]oxy]-2-methylpropanoic acid, disodium salt

(A) 3,4-Dihydroxybenzoic acid, 2-[[2-[(phenylmethoxy)carbonyl]hydrazino]carbonyl]-hydrazide 19.52 ml (0.10 mol) of N-methyl-N-trimethylsilyltrifluoroacetamide was added to a suspension of 4.20 g (0.025 mol) of 3,4-dihydroxybenzoic acid, hydrazide in 25 ml of dry acetonitrile. Stirring was continued at room temperature until a clear solution was formed (40 minutes). After evaporation in vacuo at 30°–40° C., the residue was dissolved in 25 ml of dry dichloromethane. This solution was dropped into a stirred suspension of 5.72 g (25.0 mmol) of [[[(phenylmethoxy)carbonyl]hydrazino]carbonyl]chloride at 5° C. After stirring for 1 hour at 0° C., the mixture was evaporated in vacuo and the oily residue was stirred with ether containing 4 ml of methanol until it became crystalline; yield after washing with ether and drying in vacuo: 8.77 g.

(B) 3,4-Dihydroxybenzoic acid, 2-(hydrazinocarbonyl)hydrazide, hydrochloride A solution of 3.60 g (10.0 mmol) of 3,4-dihydroxybenzoic acid, 2-[[2-[(phenylmethoxy)carbonyl]hydrazino]carbonyl]hydrazide in 90 ml of dry methanol containing 1.67 ml (20.0 mmol) of concentrated hydrochloric acid was hydrogenated in the presence of 0.36 g of 10% palladium on charcoal for 15 minutes. After the removal of the catalyst by filtration and of the solvent by evaporation in vacuo, the crude solid (2.61 g) was stirred with a few ml of dry ether; yield: 2.41 g.

(C) (S)-[1-[[[[2-[[2-[(3,4-Dihydroxybenzoyl)hydrazino]carbonyl]hydrazino]sulfonyl]amino]carbonyl]-2-oxo-3-azetidinyl]carbamic acid, phenylmethyl ester 3.52 ml (0.018 mol) of N-methyl-N-trimethylsilyltrifluoroacetamide was added to a suspension of 1.31 g (0.015 mol) of 3,4-dihydroxybenzoic acid, 2-(hydrazinocarbonyl)hydrazide, hydrochloride in 10 ml of dry ethyl acetate. After stirring for 2 hours at 50° C., the almost clear solution was evaporated in vacuo and the residue was dissolved in 15 ml of dry ethyl acetate (solution A).

To a suspension of 1.10 g (0.005 mol) of (S)-(2-oxo-3-azetidinyl)carbamic acid, phenylmethyl ester in 40 ml of dry ethyl acetate, 0.45 ml (0.005 mol) of chlorosulfonyl isocyanate was added with stirring and the mixture was stirred for 1 hour at room temperature and then cooled to 0° C. After the addition of 10 ml of dry dichloromethane and 2.09 ml (0.015 mol) of triethylamine, solution A was dropped in with stirring at 0° C. After stirring overnight at 0° C., the reaction mixture was poured into 10.0 ml of an ice cold buffer solution (citrate pH 2). The pH was maintained by the addition of 2N hydrochloric acid (pH=2). The organic layer was separated and the aqueous phase was extracted with ethyl acetate. The organic layers were combined, washed with brine, dried (magnesium sulfate) and evaporated in vacuo to leave a solid foam which became crystalline by stirring with ether/petroleum ether (1:1); yield: 2.61 g.

(D) (S)-3-Amino-1-[[[[2-[[2-(3,4-dihydroxybenzoyl)hydrazino]carbonyl]hydrazino]sulfonyl]amino]carbonyl]-2-oxo-1-azetidinecarboxamide, trifluoroacetate salt At 0° C., 1.10 g (2.0 mmol) of (S)-[1-[[(chlorosulfonyl)amino]carbonyl]-2-oxo-3-acetidinyl]carbamic acid, phenylmethyl ester was added to a mixture of 3.31 ml of trifluoroacetic acid and 0.78 ml (6.63 mmol) of thioanisole. After stirring oveernight at room temperature, the yellow solution was dropped into 40 ml of dry ether and the precipitated material was collected by suction (0.97 g) and stirred with 10 ml of dichloromethane; yield: 0.81 g.

(E) [3S(Z)]-2-[[[1-(2-Amino-4-thiazolyl)-2-[[1-[[[[2-[[2-(3,4-dihydroxybenzoyl)hydrazino]carbonyl]hydrazino]sulfonyl]amino]carbonyl]-2-oxo-3-azetidinyl]amino-2-oxoethylidene]amino]oxy]-2-methylpropanoic acid, diphenylmethyl ester Into a −30° C. cold mixture of 0.66 g (1.5 mmol) of (Z)-2-amino-α-[[1-(diphenylmethoxycarbonyl)-1-methylethoxy]imino]-4-thiazoleacetic acid in 13 ml of dry dimethylformamide, 0.63 ml (4.5 mmol) of triethylamine was dropped, followed by 0.33 ml (1.5 mmol) of diphenylchlorophosphate. After stirring at −30° C. for 1 hour, 0.42 ml (3.0 mmol) of triethylamine was dropped in, followed by the addition of 0.80 g (1.5 mmol) of (S)-3-amino-1-[[[[2-[[2-(3,4-dihydroxybenzoyl)hydrazino]carbonyl]hydrazino]sulfonyl]amino]carbonyl]-2-oxo-1-azetidinecarboxamide, trifluoroacetate salt. The mixture was stirred for 2 hours at −10° C. and overnight at 0° C. The solvent was removed in vacuo and the residue was taken up in a few ml of ethyl acetate and ice water. The pH of the mixture was corrected to pH=2 by the addition of dilute hydrochloric acid. The insoluble material was collected by suction[(1)] and [(1)]From the organic layer of the filtrate, an additional amount of [3S(Z)]-2-[[[1-(2-amino-4-thiazolyl)-2-[[1-[[[[2-[[2-(3,4-dihydroxybenzoyl)hydrazino]carbonyl]hydrazino]sulfonyl]amino]carbonyl]-2-oxo-3-azetidinyl]amino]-2-oxoethylidene]amino]oxy]-2-methylpropanoic acid, diphenylmethyl ester was obtained. This material, however, was markedly less pure; yield: 0.33 g. stirred with a few ml of ethyl acetate until it became crystalline; yield after drying in vacuo: 0.79 g.

(F) [3S(Z)]-2-[[[1-(2-Amino-4-thiazolyl)-2-[[1-[[[[2-[[2-(3,4-dihydroxybenzoyl)hydrazino]carbonyl]hydrazino]sulfonyl]amino]carbonyl]-2-oxo-3-azetidinyl]amino]-2-oxoethylidene]amino]oxy]-2-methylpropanoic acid, disodium salt To a suspension of 0.71 g (0.85 mmol) of crude [3S-(Z)]-2-[[[1-(2-amino-4-thiazolyl)-2-[[1-[[[[2-[[2-(3,4-dihydroxybenzoyl)hydrazino]carbonyl]hydrazino]sulfonyl]amino]carbonyl]-2-oxo-3-azetidinyl]amino]-2-oxoethylidene]amino]oxy]-2-methylpropanoic acid, diphenylmethyl ester in 5 ml of dry dichloromethane, 1.0 ml of anisole was added, followed by 10 ml of −10° C. cold trifluoroacetic acid. After stirring at 0° C. for 30 minutes, the solvent was removed in vacuo at 0°–5° C.

to leave a residue which solidified by stirring with ether (0.46 g). This crude trifluoroacetic acid salt of [3S-(Z)]-2-[[[1-(2-amino-4-thiazolyl)-2-[[1-[[[2-[[2-(3,4-dihydroxybenzoyl)hydrazino]carbonyl]hydrazino]sulfonyl]amino]carbonyl]-2-oxo-3-azetidinyl]amino]-2-oxoethylidene]amino]oxy]-2-methylpropanoic acid, disodium salt was suspended in a few ml of cold water and the pH was adjusted to 6.0 by the addition of dilute sodium hydroxide (1%). MPLC-purification on XAD-2 resin eluting with water yielded, after freeze drying the approximate fractions, 0.15 g of [3S(Z)]-2-[[[1-(2-amino-4-thiazolyl)-2-[[1-[[[2-[[2-(3,4-dihydroxybenzoyl)hydrazino]carbonyl]hydrazino]sulfonyl]amino]carbonyl]-2-oxo-3-acetidinyl]amino]-2-oxoethylidene]amino]oxy]-2-methylpropanoic acid, disodium salt as a colorless powder.

EXAMPLE 14

[3S(Z)]-2-[[[1-(2-Amino-4-thiazolyl)-2-[[1-[[[-[2-[amino(3,4-dihydroxyphenyl)acetyl]hydrazino]sulfonyl]amino]carbonyl]-2-oxo-3-acetidinyl]amino]-2-oxoethylidene]amino]oxy]-2-methylpropanoic acid, monosodium salt (A)

(S)-[1-[[[[2-[(3,4-dihydroxyphenyl)[[(phenylmethoxy)carbonyl]amino]acetyl]hydrazino]sulfonyl]amino]carbonyl]-2-oxo-3-azetidinyl]carbamic acid, phenylmethyl ester 3.91 ml (0.020 mol) of N-Methyl-N-trimethylsilyltrifluoroacetamide was added to a suspension of 2.97 g (0.010 mol) of 3,4-dihydroxy-α-[[(phenylmethoxy)carbonyl]amino]benzoic acid, hydrazide of dry ethyl acetate. After stirring for 3 hours at 50° C., the clear solution was evaporated in vacuo and the residue was dissolved in 20 ml of dry ethyl acetate (solution A).

To a suspension of 2.20 g (0.010 mol) of (S)-(2-oxo-3-azetidinyl)carbamic acid, phenylmethyl ester in 80 ml of dry ethyl acetate, 0.90 ml (0.010 mol) of chlorosulfonylisocyanate was added with stirring and the mixture was stirred for 1 hour at room temperature and then cooled to 0° C. After the addition of 20 ml of dry dichloromethane and 4.18 ml (0.030 mol) of triethylamine, solution A was dropped in with stirring at 0° C. Stirring was continued for 10 minutes at 0° C. and 2.5 hours at room temperature. Then the reaction mixture was poured into 150 ml of an ice cold buffer solution (citrate pH 3). The pH was maintained by the addition of 2N hydrochloric acid (pH=3). The organic layer was separated and the aqueous phase was extracted with ethyl acetate. The organic layers were combined, washed with brine, dried (magnesium sulfate) and evaporated in vacuo to leave a solid foam. This crude mixture of diastereomers of (S)-[1-[[[[2-[(3,4-dihydroxyphenyl)[[(t-butyloxy)carbonyl]amino]acetyl]hydrazino]sulfonyl]amino]carbonyl]-2-oxo-3-azetidinyl]carbamic acid, phenylmethyl ester was stirred with petroleum ether containing a few ml of ether until it became crystalline; yield: 7.1 g. The crystalline mixture of diastereomers of (S)-[1-[[[[2-[(3,4-dihyroxyphenyl)[[(t-butyloxy)carbonyl]amino]acetyl]hydrazino]sulfonyl]amino]carbonyl]-2-oxo-3-azetidinyl]carbamic acid, phenylmethyl ester was dissolved in 35 ml of methanol. After the addition of 17 ml of water, the pH of the solution was adjusted to 6.0 by the addition of dilute (1%) sodium hydroxide solution. The solution was concentrated in vacuo until an oil was separated which solidified by stirring with ether; yield: 3.3 g.

Freeze drying of the aqueous phase yielded, after stirring with ether, an additional 2.5 g of (S)-[1-[[[[2-[(3,4-dihydroxyphenyl)[[(t-butyloxy)carbonyl]amino]acetyl]hydrazino]sulfonyl]amino]carbonyl]-2-oxo-3-azetidinyl]carbamic acid, phenylmethyl ester.

(B)

[3S(Z)]-2-[[[1-(2-Amino-4-thiazolyl)-2-[[1-[[[2-[[[(t-butyloxy)carbonyl]amino](3,4-dihydroxyphenyl)acetyl]hydrazino]sulfonyl]amino]carbonyl]2-oxo-3-azetidinyl]amino]-2-oxoethylidene]amino]oxy]-2-methylpropanoic acid, diphenylmethyl ester 1.29 g (2.0 mmol) of (S)-[1-[[[[2-[(3,4-dihydroxyphenyl)[[(t-butyloxy)carbonyl]amino]acetyl]hydrazino]sulfonyl]amino]carbonyl]-2-oxo-3-azetidinyl]carbamic acid, phenylmethyl ester was dissolved in 20 ml of dry dimethylformamide and hydrogenated in the presence of 0.13 g palladium on charcoal (10%) for 15 minutes. The catalyst was removed by filtration and washed twice with 5 ml of dimethylformamide (filtrate A).

Into a −30° C. mixture of 0.88 g (20 mmol) (Z)-2-amino-α-[[1-(diphenylmethoxycarbonyl)-1-methylethoxy]imino]-4-thiazoleacetic acid in 18 ml of dry dimethylformamide, 0.84 ml (6.0 mmol) of triethylamine was dropped, followed by 0.42 ml (2.0 mmol) of diphenylchlorophosphate. Stirring was continued at −30° C. for 1 hour. Then the filtrate A was dropped in at −30° C. The mixture was stirred for 1 hour at −10° C. and for an additional 2.5 hours at 0° C. The solvent was removed in vacuo and the residue was taken up in ethyl acetate and 35 ml of ice cold buffer solution (citrate pH 2). The pH of the mixture was corrected to pH=2 by the addition of dilute hydrochloric acid and the aqueous phase was extracted three times with ethyl acetate. The combined organic phases were washed with buffer solution (citrate pH 2) and brine, dried (magnesium sulfate) and evaporated in vacuo.

The residue was dissolved in a few ml of ethyl acetate and the mixture of diastereomers of [3S(Z)]-2-[[[1--(2-amino-4-thiazolyl)-2-[[1-[[[2-[[[(t-butyloxy)carbonyl]amino](3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, diphenylmethyl ester was precipitated by the addition of ether while vigorously stirring; yield: 1.8 g.

(C)

[3S(Z)]-2-[[[1-(2-Amino-4-thiazolyl)-2-[[1-[[-[[2-[amino(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, monosodium salt To a suspension of 1.7 g (1.87 mmol) of crude [3S (Z)]-2-[[[1-(2-amino-4-thiazolyl)-2-[[1-[[[2-[[[(t-butyloxy)carbonyl]amino](3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, diphenylmethyl ester in 5 ml of dichloromethane, 1.7 ml of anisole was added, followed by 17 ml of −10° C. cold trifluoroacetic acid. After stirring at 0° C. for 30 minutes, the solvent was removed in vacuo at 0°-5° C. to leave a residue which solidified upon stirring with ether; yield: 1.34 g. 1.1 g (1.26 mmol) of this salt was suspended in a few ml of cold water and the pH was adjusted to 6.0 by the addition of dilute sodium hydroxide (1%). This solution was purified by column chromatography on HP-20 resin eluting with water. Freeze drying of the appropriate fractions yielded 0.55 g of [3S(Z)]-2-[[[1-(2-amino-4-thiazolyl)-2-[[1-[[[[2-[amino(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, monosodium salt as a mixture of diastereomers.

EXAMPLE 15

[3S(Z)]-2-[[[1-(2-Amino-4-thiazolyl)-2-[[1-[[[[2-[(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, disodium salt (A) 3,4-Dihydroxyphenyl acethydrazide A solution of 13.6 g (0.066 mol) of dicyclohexylcarbodiimide in 60 ml of dry tetrahydrofuran was dropped into a solution of 10.28 g (0.060 mol) of 3,4-dihydroxyphenylacetic acid, 8.9 g (0.066 mol) of (t-butoxycarbonyl)hydrazide, 0.74 g (0.006 mol) of 4-dimethylaminopyridine and 0.93 g (0.006 mol) of N-hydroxybenzotriazole. Stirring was continued for 4.5 hours at room temperature. The precipitated dicyclohexylurea was filtered off and the filtrate was evaporated in vacuo. The residue was taken up in ethyl acetate and washed successively with dilute sodium bicarbonate solution, buffer solution (citrate pH 3) and brine. After drying (magnesium sulfate) and evaporation in vacuo, the residue (17.6 g) was purified by column chromatography on silica gel eluting with ethyl acetate/toluene (2:1). The appropriate fractions were combined and evaporated in vacuo and the residue was stirred with ether; yield: 9.77 g, melting point 150°-152° C., dec.

3.58 g (12.7 mmol) of the t-butoxycarbonyl protected precursor was added to a −10° C. cold mixture of 1.38 ml (12.7 mmol) of anisole and 40 ml of trifluoroacetic acid. After stirring for 30 minutes at 0° C., the solvent was removed in vacuo and the residue was stirred with dry ether, collected by suction and dried in vacuo over phosphorous pentoxide; yield: 3.77 g. 2.59 ml (14.0 mmol) of N-methyl-N-trimethylsilyltrifluoroacetamide was added to a suspension of 1.38 g (4.65 mmol) of this trifluoroacetic acid salt in 20 l of dry acetonitrile. After stirring for 30 minutes at room temperature, the mixture was evaporated in vacuo and the residue was taken up in a few ml of dry ether and 0.6 ml of methanol was added. The solution was evaporated again in vacuo and the residue was stirred with petroleum ether until the sticky material became crystalline; yield: 0.79 g.

(B)

(S)-[1-[[[[2-[(3,4-Dihydroxyphenyl)acetyl]hydrazino]sulfonyl]amino]carbonyl]-2-oxo-3-azetidinyl]carbamic acid, phenylmethyl ester 1.95 ml (10.0 mmol) of N-methyl-N-trimethylsilyltrifluoroacetamide (95%) was added to a suspension of 0.91 g (5.0 mmol) of 3,4-dihydroxyphenylacetylhydrazide in 15 ml of dry ethyl acetate. After stirring for 1 hour at 50°-55° C., the almost clear solution was evaporated in vacuo and the residue was dissolved in 10 ml of dry ethyl acetate (solution A).

To a suspension of 1.10 g of (S)-(2-oxo-3-azetidinyl)carbamic acid, phenylmethyl ester (5.0 mmol) in 40 ml of dry ethyl acetate, 0.45 ml (5.0 mmol) of chlorosulfonyl isocyanate was added with stirring. The mixture was stirred for 1 hour at room temperature and then cooled to 0° C. After the dropwise addition of a solution of 2.09 ml (15.0 mmol) of triethylamine in 10 ml of dry dichloromethane and solution A, stirring was continued for 2.5 hours at 0° C. Ice water was added, and the organic layer was separated and washed successively with cold buffer solution (citrate pH 2) and brine. Drying (magnesium sulfate) and evaporation in vacuo gave a residue which solidified by stirring with ether; yield: 2.1 g.

(C)

(S)-3-Amino-N-[[[2-[(3,4-dihydroxyphenyl)acetyl]hydrazino]sulfonyl]-2-oxo-1-azetidinecarboxamide, trifluoroacetate salt At 0° C., 0.60 g (1.23 mmol) of (S)-[1-[[[[2-[(3,4-dihydroxyphenyl)acetyl]hydrazino]sulfonyl]amino]carbonyl]-2-oxo-3-azetidinyl]carbamic acid, phenylmethyl ester was added to a mixture of 2.04 ml of trifluoroacetic acid and 0.48 ml (4.8 mmol) of thioanisole. After stirring overnight at room temperature, the solvent was removed in vacuo and the residue was stirred with dry dichloromethane. The precipitate was collected by suction and dried in vacuo over phosphorous pentoxide; yield: 0.6 g.

(D)

[3S(Z)]-2-[[[1-(2-Amino-4-thiazolyl)-2-[[1-[[[[2-[(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, diphenylmethyl ester Into a −30° C. cold mixture of 0.55 g (1.25 mmol) (Z)-2-amino-α-[[1-(diphenylmethoxycarbonyl)-1-methylethoxy]imino]-4-thiazoleacetic acid in 12.5 ml of dry dimethylformamide, 0.53 ml of triethylamine was dropped, followed by 0.34 g (1.25 mmol) of diphenylchlorophosphate. After stirring at −30° C. for 1 hour, 0.35 ml (2.5 mmol) of triethylamine was dropped in, followed by the addition of 0.58 g (ca. 1.2 mmol) of (S)-3-amino-N-[[[2-[(3,4-dihydroxyphenyl)acetyl]hydrazino]sulfonyl]-2-oxo-1-azetidinecarboxamide, trifluoroacetate salt. The mixture was stirred for 2 hours at −10° C. and 1 hour at 0° C. The solvent was removed in vacuo, and the residue was taken up in 12.5 ml of ethyl acetate and 5 ml of ice water. The pH of the mixture was corrected to 1.5 by the addition of dilute hydrochloric acid. The organic layer was separated and the aqueous phase was extracted twice with 4 ml of ethyl acetate. The combined organic layers were washed with buffer solution (citrate pH 2) and brine and dried (magnesium sulfate). The solvent was distilled off in vacuo to leave a solid foam which became crystalline by stirring with ether; yield: 1.08 g. This material was used in the next step without any further purification.

(E)

[3S(Z)]-2-[[[1-(2-Amino-4-thiazolyl)-2-[[1-[[[[2-[(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, disodium salt To a suspension of 1.07 g of [3S(Z)]-2-[[[1-(2-amino-4-thiazolyl)-2-[[1-[[[[2-[(3,4-dihydroxyphenyl)acetyl]hydrazino]sulfonyl]amino]-carbonyl]-2-oxo-3-azetidinyl]amino]-2-oxoethylidene]amino]oxy]-2-methylpropanoic acid, diphenylmethyl ester in 7 ml of dry dichloromethane, 3.0 ml of anisole was added, followed by 30 ml −10° C. cold trifluoroacetic acid. After stirring at 0° C. for 10 minutes, the solvent was removed in vacuo and the residue was taken up in ice water and ether. The pH of the mixture was adjusted to 6.5 by the addition of dilute sodium hydroxide (1%). The organic layer was separated and the aqueous phase was freeze dried. Reversed phase chromatography of the crude product on HP-20 resin eluting with water yielded, after freeze drying the appropriate fractions, 0.14 g of [3S(Z)]-2-[[[1-(2-amino-4-thiazolyl)-2-[[1-[[[[2-[(3,4-dihydroxyphenyl)acetyl]hydrazino]sulfonyl]amino]carbonyl]-2-oxo-3-azetidinyl]amino]-2-oxoethylidene]amino]oxy]-2-methylpropanoic acid, disodium salt as a colorless powder; melting point >220° C., dec.

EXAMPLE 16

[3S(Z)]-2[[[1-(2-Amino-4-thiazolyl)-2-[[1-[[[[(2-cyano-4,5-dihydroxyphenyl)amino]sulfonyl]amino]carbonyl]-2-oxo-3-azetidinyl]amino]-2-oxoethylidene]amino]oxy]-2-methylpropanoic acid, disodium salt

(A) 2-Amino-4,5-dihydroxybenzonitrile

To a solution of 15.65 g (87.83 mmol) of 2-amino-4,5-dimethoxybenzonitrile in 440 ml of dry dichloromethane was added dropwise at −78° C., 66.0 g (263.5 mmol) of boron tribromide. The mixture was stirred overnight while the mixture was allowed to warm to room temperature. After the addition of 180 ml of water, the resulting precipitate was filtered off and dried in vacuo (37.6 g). The crude material was dissolved in 570 ml of methanol, 0.5 ml of concentrated hydrochloric acid was added and the mixture was refluxed for 1 hour. Evaporation to dryness yielded 18.75 g of 2-amino-4,5-dihydroxybenzonitrile as the hydrobromide salt.

11.5 g (50.0 mmol) of the salt was dissolved in 80 ml of water and the pH was brought to 5.8 by the addition of 2N sodium hydroxide. The resulting precipitate was filtered off and dried over phosphorous pentoxide; yield: 5.2 g. Extraction of the aqueous phase with ether yielded another 0.75 g of the material. The combined product was dissolved in ethyl acetate, a dark colored residue was filtered off and the filtrate was treated with charcoal. Evaporation of the solvent yielded 5.74 g of pure product as cream colored crystals; melting point 205.5° C.

(B) (S)-[1-[[[[(2-cyano-4,5-dihydroxyphenyl)amino]sulfonyl]amino]carbonyl]-2-oxo-3-azetidinyl]carbamic acid, phenylmethyl ester To a suspension of 4.5 g (30.0 mmol) of 2-amino-4,5-dimethoxybenzonitrile in 60 ml of absolute ethyl acetate was added 12.0 g (60.0 mmol) of N-methyl-N-(trimethylsilyl)trifluoroacetamide. After stirring for 1.5 hours, the clear solution was evaporated to dryness, finally at high vacuum at 50° C. The residue was dissolved in 55 ml of ethyl acetate (solution A). To a suspension of 6.6 g (30.0 mmol) of (S)-(2-oxo-3-azetidinyl)carbamic acid, phenylmethyl ester in 150 ml of ethyl acetate was added 4.65 g (33.0 mmol) of chlorosulfonyl isocyanate. After stirring for 1 hour, the solution was cooled to 0° C. and 50 ml of dichloromethane and 9.0 g (90.0 mmol) of triethylamine (dropwise) were added. To this mixture, solution A was added dropwise at 0° C. and after stirring overnight at room temperature, the mixture was poured into ice water. The pH was adjusted to 2.0 with 3N hydrochloric acid. The organic phase was separated and the aqueous phase extracted twice with ethyl acetate. The combined organic phases were extracted twice with brine and dried over sodium sulfate. Evaporation of the solvent yielded 13.5 g of crude product which was slurried twice, each time with 200 ml of ether for 2 hours; yield of crystalline material after drying: 6.5 g. When petroleum ether was added to the ether layers, another 3.5 g of pure product was precipitated. Total yield: 10.0 g; melting point 111.9° C., dec.

(C) (S)-3-Amino-N-[[(2-cyano-4,5-dihydroxyphenyl)amino]sulfonyl]-2-oxo-1-azetidinecarboxamide, trifluoroacetate ester 6.2 g (13.0 mmol) of (S)-[1-[[[[(2-cyano-4,5-dihydroxyphenyl)amino]sulfonyl]amino]carbonyl]-2-oxo-3-azetidinyl]carbamic acid, phenylmethyl ester was added at −10° C. to a mixture of 32 ml of trifluoroacetic acid and 8 ml of thioanisole. After stirring overnight at 0° C., the mixture was poured into 200 ml of dichloromethane. The separated oil was isolated and treated with 125 ml of ether to yield a crystalline material which was filtered off, washed with ether and petroleum ether and dried in vacuo; yield: 3.0 g. Evaporation of the dichloromethane solution and trituration of the residue with ether and again dichloromethane yielded 1.7 g; total yield: 4.7 g, melting point 216.7° C.

(D) [3S(Z)]-2[[[1-(2-Amino-4-thiazolyl)-2-[[1-[[[[(2-cyano-4,5-dihydroxyphenyl)amino]sulfonyl]amino]carbonyl]-2-oxo-3-azetidinyl]amino]-2-oxoethylidene]amino]oxy]-2-methylpropanoic acid, diphenylmethyl ester To a solution of 2.60 g (6.0 mmol) of (Z)-2-amino-α-[[-(diphenylmethoxycarbonyl)-1-methylethoxy]imino]-4-thiazoleacetic acid and 1.80 g (18.0 mmol) of triethylamine in 60 ml of absolute dimethylformamide was added dropwise at −30° C., 1.60 g (6.0 mmol) of diphenylchlorophosphate. After stirring for one hour, 1.2 g (12.0 mmol) of triethylamine and 2.7 g (6.0 mmol) of (S)-3-amino-N-[[(2-cyano-4,5-dihydroxyphenyl)amino]sulfonyl]-2-oxo-1-azetidinecarboxamide, trifluoroacetate salt was added. After stirring for 2 hours at −10° C. and 1.5 hours at 0° C., the dimethylformamide was evaporated in vacuo and to the residue were added 50 ml of ice water and 100 ml of ethyl acetate. The pH was adjusted to 1.5 with 1N hydrochloric acid. The phases were separated and the aqueous phase was extracted twice with ethyl acetate. The combined organic phases were washed with dilute hydrochloric acid and twice with water. Drying and evaporation of the solvent yielded after trituration with ether 5.0 g of crude product (quant.).

(E) [3S(Z)]-2[[[1-(2-Amino-4-thiazolyl)-2-[[1-[[[[(2-cyano-4,5-dihydroxyphenyl)amino]sulfonyl]amino]carbonyl]-2-oxo-3-azetidinyl]amino]-2-oxoethylidene]amino]oxy]-2-methylpropanoic acid, disodium salt To a suspension of 2.3 g (3.0 mmol) of [3S(Z)]-2[[[1--(2-amino-4-thiazolyl)-2-[[1-[[[[(2-cyano-4,5-dihydroxyphenyl)amino]sulfonyl]amino]carbonyl]-2-oxo-3-azetidinyl]amino]-2-oxo-ethylidene]amino]oxy]-2-methylpropanoic acid, diphenylmethyl ester in 5.5 ml of anisole was added dropwise at −10° C. 28 ml of trifluoroacetic acid. After stirring for one hour, 120 ml of ether was added and the resulting precipitate was filtered off, washed with ether and petroleum ether and dried in vacuo; yield: 1.4 g.

1.0 g of the crude salt was dissolved in 40 ml of water and the pH was brought to 6.4 with 1N sodium hydroxide. Freeze drying yielded 1.1 g of crude sodium salt of which 0.9 g were chromatographed on XAD under MPLC conditions with water as eluent. Yield of pure freeze dried product was 0.19 g; melting point 246°–249° C., dec.

EXAMPLE 17

[3S(Z)]-2-[[[1-(2-Amino-4-thiazolyl)-2-[[1-[[[[2-[(3,4-d-ihydroxyphenyl)amino]-2-oxoethyl]amino]sulfonyl]amino]carbonyl]-2-oxo-3-acetidinyl]amino]-2-oxoethylidene]amino]oxy]-2-methylpropanoic acid, disodium salt (A)
[2-[(3,4-Dimethoxyphenyl)amino]-2-oxoethyl]carbamic acid, phenylmethyl ester To a suspension of 25.9 g (124 mmol) of N-(phenylmethoxycarbonyl)glycine in 370 ml of dichloromethane, were added at 0° C., 0.74 ml of dimethylformamide and 18.8 g (148 mmol) of oxalylchloride. The mixture was allowed to warm to room temperature and was then added dropwise to a mixture of 19.0 g (124 mmol) of 3,4-dimethoxyaniline (sublimed) and washed with 10% hydrochloric acid solution and twice with water, and dried over sodium sulfate. After the evaporation of the solvent, the residue was triturated with ether and dried in vacuo; yield: 26.3 g.

(B) 2-Amino-N-(3,4-dihydroxyphenyl)acetamide

To a solution of 26.2 g (76.2 mmol) of [2-[(3,4-dimethoxyphenyl)amino]-2-oxoethyl]carbamic acid in 1 liter of absolute dichloromethane was added dropwise at −60° C. 63.1 g of boron tribromide. After stirring overnight at room temperature, 180 ml of water was added at 0° C. The resulting precipitate was filtered off and dried in vacuo. To a solution of 26.1 g of crude 2-amino-N-(3,4-dihydroxyphenyl)acetamide hydrobromide salt in 600 ml of methanol was added 8 ml of concentrated hydrochloric acid and the mixture was refluxed for 1 hour. Evaporation to dryness yielded 16.5 g of the hydrobromide salt of 2-amino-N-(3,4-dihydroxyphenyl)acetamide. To a solution of 15.4 g of 2-amino-N-(3,4-dihydroxyphenyl)acetamide hydrobromide salt in 175 ml of water was added sodium bicarbonate until the pH reached 6.7. The resulting precipitate was filtered off with suction and dried in vacuo; yield: 10.5 g.

(C)
(S)-[1-[[[[2-[(3,4-Dihydroxyphenyl)amino]-2-oxoethyl]amino]sulfonyl]amino]carbonyl]-2-oxo-3-azetidinyl]-carbamic acid, phenylmethyl ester To a suspension of 1.24 g (6.79 mmol) of 2-amino-N-(3,4-dihydroxyphenyl)acetamide in 30 ml of absolute acetonitrile was added 2.71 g (13.6 mmol) of N-methyl-N-(trimethylsilyl)trifluoroacetamide. After stirring for two hours, the clear solution was evaporated to dryness, finally at high vacuum at 55° C. The residue was dissolved in 30 ml of ethyl acetate (solution A). To a suspension of 1.5 g (6.79 mmol) of (S)-(2-oxo-3-azetidinyl)carbamic acid, phenylmethyl ester in 40 ml of ethyl acetate was added 0.96 g (6.79 mmol) of chlorosulfonyl isocyanate. After stirring for one hour, the solution was cooled to 0° C. and 15 ml of dichloromethane and subsequently 2.06 g (20.37 mmol) of triethylamine (dropwise) was added. To this mixture, solution A was added dropwise and after stirring overnight at room temperature, 30 ml of ice water was added. The pH was adjusted to 1 with 3N hydrochloric acid, the phases were separated and the organic phase was dried over sodium sulfate. After the evaporation of the solvent, the residue was triturated with ether, filtered and dried in vacuo; yield: 1.63 g.

(D)
(S)-3-Amino-N-[[[2-[(3,4-dihydroxyphenyl)amino]-2-oxoethyl]amino]sulfonyl]-2-oxo-1-azetidinecarboxamide, trifluoroacetate salt To a suspension of 1.4 g (2.76 mmol) of (S)-[1[[[[2-[(3,4-dihydroxyphenyl)amino]-2-oxoethyl]amino]sulfonyl]amino]carbonyl]-2-oxo-3-azetidinyl]carbamic acid, phenylmethyl ester in 1.1 g of thioanisole was added 3 ml of trifluoroacetic acid and the mixture was stirred overnight at room temperature. 50 ml of ether was added and the resulting crystals were filtered off, washed twice with ether and finally triturated with dichloromethane; yield: 1.22 g.

(E)
[3S(Z)]-2-[[[1-(2-Amino-4-thiazolyl)-2-[[1-[[[[2-[(3,4-dihydroxyphenyl)amino]-2-oxoethyl]amino]sulfonyl]amino]carbonyl]-2-oxo-3-azetidinyl]-amino]-2-oxoethylidene]amino]oxy]-2-methylpropanoic acid, disodium salt To a solution of 1.12 g (2.55 mmol) of (Z)-2-amino-α-[[1-(diphenylmethoxycarbonyl)-1-methylethoxy]imino]-4-thiazoleacetic acid and 0.77 g (7.64 mmol) of triethylamine in 45 ml of absolute dimethylformamide was added dropwise at −30° C. 0.61 g (2.55 mmol) of diphenylchlorophosphate. After stirring for one hour, 0.52 g (5.10 mmol) of triethylamine and 1.16 g (2.55 mmol) of (S)-3-amino-N-[[[2-[(3,4-dihydroxyphenyl)amino]-2-oxoethyl]amino]sulfonyl]-2-oxo-1-azetidinecarboxamide, trifluoroacetate salt were added. After stirring for 2 hours at −10° C. and one additional hour at 0° C., the dimethylformamide was evaporated in vacuo and to the residue were added 20 ml of ice water and 50 ml of ethyl acetate. The pH was adjusted with 3N hydrochloric acid to 1, the organic phase was separated, washed with dilute hydrochloric acid, water and brine and finally dried over magnesium sulfate. After the evaporation of the solvent, the residue was triturated with ether and dried in vacuo; yield: 1.15 g.

To a suspension of 1.10 g (1.41 mmol) of the protected product in 2.2 ml of anisole was added dropwise at −10° C. 11 ml of trifluoroacetic acid. After stirring for 1 hour, the excess trifluoroacetic acid and anisole were distilled off in vacuo. The residue was triturated with ether, filtered off by suction, washed with ether and dried in vacuo (0.82 g). The trifluoroacetic acid salt was dissolved in 30 ml of water:methanol (1:1) and pH brought to 6.5 with dilute sodium hydroxide. Freeze drying yielded 0.85 g of crude product which was chromatographed on XAD under MPLC conditions with water as eluent; yield of pure freeze dried product: 150 mg; melting point 230°–260° C., dec.

EXAMPLE 18

[3S(Z)]-1-[[[1-(2-Amino-4-thiazolyl)-2-[[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, disodium salt (A) 3,4-Dihydroxybenzoic acid, 1-methylhydrazide 0.11 g (0.05 mol) of 3,4-dihydroxybenzoic acid, ethyl ester and 106 ml of methylhydrazine (2 mol) were refluxed for 3 days. The reaction mixture was evaporated in vacuo and the oily residue treated with ethanol and evaporated again. This was repeated once more. After retreatment with ethanol, 3,4-dihydroxybenzoic acid, 1-methylhydrazide began to crystallize. The crude product was removed by filtration and recrystallized from ethanol; yield: 3.8 g, melting point 202°–205° C.

(B)
(S)-[1-[[[[2-(3,4-Dihydroxybenzoyl)-2-methylhydrazino]sulfonyl]amino]carbonyl]-2-oxo-3-azetidinyl]-carbamic acid, phenylmethyl ester 9.53 ml of N-methyl-N-(trimethylsilyl)trifluoroacetamide (0.051 mol) was added to a suspension of 4.2 g of 3,4-dihydroxybenzoic acid, 1-methylhydrazide (0.023 mol). After warming the suspension to 50° C. for one hour, a clear solution of 3,4-bis(trimethylsilyl)benzoic acid, 1-methylhydrazide was obtained.

5.06 g of (S)-(2-oxo-3-azetidinyl)carbamic acid, phenylmethyl ester (0.023 mol) was suspended in 100 ml of ethyl acetate and 2 ml (0.023 mol) of chlorosulfonyl isocyanate was dropped in with stirring. The mixture was stirred for 1 hour at room temperature to form a clear solution which was cooled to 0°–5° C. 50 ml of dichloromethane and 9.62 ml of triethylamine were added followed by the slow addition of the solution of 3,4-bis(trimethylsilyl)benzoic acid, 1-methylhydrazide. After stirring at room temperature overnight, ice water was added and the mixture was stirred for 30 minutes. The two phases were separated, the aqueous phase was layered with 200 ml of ethyl acetate and acidified to pH 2 by the addition of 2N hydrochloric acid. The aqueous phase was washed twice with 100 ml each of ethyl acetate, the combined organic phases were dried (magnesium sulfate) and evaporated to yield a foam, which was treated with ether; yield: 8.7 g.

(C)
(S)-3-Amino-N-[[2-(3,4-dihydroxybenzoyl)-2-methylhydrazino]sulfonyl]-1-azetidinecarboxamide, trifluoroacetate salt 8.7 g of crude (S)-[1-[[[[2-(3,4-dihydroxybenzoyl)-2-methylhydrazino]sulfonyl]amino]carbonyl]-2-oxo-3-azetidinyl]carbamic acid, phenylmethyl ester was added at 10° C. to a mixture formed from 7.6 ml of thioanisole and 32 ml of trifluoroacetic acid. The mixture was stirred overnight at 10° C. The trifluoroacetic acid was removed by evaporation in vacuo and the oily residue was treated with ether to yield 10.5 g of crude (S)-3-amino-N-[[2-(3,4-dihydroxybenzoyl)-2-methylhydrazino]sulfonyl]-1-azetidinecarboxamide, trifluoroacetate salt.

(D)
[3S(Z)]-1-[[[1-(2-Amino-4-thiazolyl)-2-[[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, diphenylmethyl ester To a solution of 7.53 g of (Z)-2-amino-α-[[(diphenylmethoxycarbonyl)-1-methylethoxy]imino]-4-thiazoleacetic acid (0.017 mol) in 150 ml of dimethylformamide was added 7.2 ml (0.051 mol) of triethylamine and the solution was cooled to −30° C., at which temperature 3.8 ml of diphenylchlorophosphate (0.017 mol) was added dropwise. The reaction mixture was stirred at −30° C. for 1 hour. Then, at the same temperature, 4.8 ml of triethylamine (0.034 mol) was added followed by 10.1 g of crude (S)-3-amino-N-[[2-(3,4-dihydroxybenzoyl)-2-methylhydrazino]sulfonyl]-1-azetidinecarboxamide, trifluoroacetate salt. The mixture was stirred for 2 hours at −10° C. and for 1 hour at 0° C. and evaporated in vacuo to remove the dimethylformamide. The residue was treated with ethyl acetate and water, which was acidified to pH 1.5–2 to form a precipitate of crude [3S(Z)]-1-[[[1-(2-amino-4-thiazolyl)-2-[[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, diphenylmethyl ester which solidified only partly. The semisolid residue was stirred with ether to yield 14.3 g of crude, solid product which was used in the next step without further purification.

(E)
[3S(Z)]-1-[[[1-(2-Amino-4-thiazolyl)-2-[[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, disodium salt 11 g of crude [3S(Z)]-1-[[[1-(2-amino-4-thiazolyl)-2-[-[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, diphenylmethyl ester was added to 22 ml of anisole. The mixture was cooled to −10° C., at which temperature 110 ml of trifluoroacetic acid was added. After stirring for 1 hour at −10° C., 400 ml of trifluoroacetic acid was added slowly with stirring while the temperature was kept at −10° C. The precipitate ([3S(Z)]-1-[[[1-(2-amino-4-thiazolyl)-2-[[1-[[[[2-[(3,4-dihydroxyphenyl)carbonyl]-2-methylhydrazino]sulfonyl]amino]carbonyl]-2-oxo-3-azetidinyl]amino]-2-oxoethylidene]amino]oxy]-2-methylpropanoic acid, trifluoroacetate salt) was filtered off to yield 7.5 g of crude material. 6.5 g of this material was converted to the sodium salt by dissolving it in acetone/water, adjusting the pH to 5.5–6 and freeze drying. The crude sodium salt (6.6 g) was purified by HP-20 chromatography; yield: 1.1 g.

EXAMPLE 19
[3S(Z)]-2-[[[1-(2-Amino-4-thiazolyl)-2-[[1-[[[[2-[2--(aminocarbonyl)-4,5-dihydroxyphenyl]amino]sulfonyl]amino]carbonyl]-2-oxo-3-azetidinyl]amino]-2-oxoethylidene]amino]oxy]-2-methylpropanoic acid, disodium salt (A) 3,4-Dimethoxy-6-nitrobenzoic acid To a suspension of 80 g (0.33 mol) of 3,4-dimethoxy-6-nitrobenzoic acid, methyl ester in 1700 ml of methanol was added 500 ml of 2N sodium hydroxide, and the mixture was warmed to 50° C. for 45 minutes. After 30 minutes, a clear solution was obtained. The methanol was evaporated in vacuo and the aqueous solution was acidified with 3N hydrochloric acid to pH 1. The resulting crystals were filtered off by suction, washed with water and dried in vacuo; yield: 72.5 g; melting point 194.9° C.

(B) 3,4-Dimethoxy-6-nitrobenzamide 23 g (0.1 mol) of 3,4-dimethoxy-6-nitrobenzoic acid was added to 200 ml of thionyl chloride, and the mixture was warmed to 60° C. for 1 hour. The excess thionyl chloride was distilled off in vacuo and the residue was triturated with petroleum ether to yield, after filtration and drying, 24.5 g of acid chloride. The acid chloride was added to 250 ml of concentrated ammonia, and the mixture was stirred overnight at room temperature. The crystals were filtered off by suction, washed twice with water and dried in vacuo; yield: 21.4 g; melting point 196.6° C.

(C) 2-Amino-4,5-dimethoxybenzamide 1.5 g of 10% palladium on charcoal was added to a suspension of 7.5 g (33 mmol) of 3,4-dimethoxy-6-nitrobenzamide in 200 ml of ethanol, and the mixture was hydrogenated for 1 hour under a pressure of 45 psi. After removal of the catalyst, the filtrate was concentrated in vacuo and the residue triturated with 80 ml of ether/petroleum ether 1:1. The crystals were filtered, washed with petroleum ether and dried in vacuo; yield: 6.15 g, melting point 142.7° C.

(D) 2-Amino-4,5-dihydroxybenzamide, monohydrochloride

To a solution of 76.6 g (306 mmol) of boron tribromide in 500 ml of dichloromethane was added dropwise at −78° C. a solution of 20 g (102 mmol) of 2-amino-4,5-dimethoxybenzamide in 1300 ml of dichloromethane. The mixture was allowed to warm slowly to room temperature with stirring overnight. Under ice cooling 250 ml of water added dropwise to the solution. The resulting precipitate was filtered off, washed with water and dried in vacuo over phosphorous pentoxide; yield of 2-amino-4-dihydroxybenzamide, monohydrochloride (contains boric acid) was 30.5 g. In order to remove the boric acid, crude 2-amino-4,5-dihydroxybenzamide, monohydrochloride (30.0 g) was suspended in 900 ml of absolute acetonitrile. Under ice cooling, 183 g bis(trimethylsilyl)acetamide were added, and the mixture was stirred for 1 hour to obtain a clear solution. The solvent was distilled off in high vacuum and the residual green oil was dissolved in 750 ml of absolute ether. After the addition of 165 ml of absolute methanol, an oil separated. The solvent was removed in vacuo and the residue evaporated in high vacuum for 45 minutes. 105 ml of water was added to the residue, and the pH was adjusted to 1 with 1N hydrochloric acid. After extraction with ether, the aqueous solution was freeze dried to yield 60.8 g of crude 2-amino-4,5-dihydroxybenzamide, monohydrochloride which contained acetamide as by-product. Crude 2-amino-4,5-dihydroxybenzamide, monohydrochloride was dissolved in 450 ml of ethanol and after the addition of 1450 ml of ether, 2-amino-4,5-dihydroxybenzamide, monohydrochloride crystallized out. After two days, the crystals were collected by filtration, washed with ether and dried in vacuo; yield: 11.3 g, melting point >300° C.

(E) (S)-[1-[[[[[2-(aminocarbonyl)-4,5-dihydroxyphenyl]amino]sulfonyl]amino]carbonyl]-2-oxo-3-azetidinyl]-carbamic acid, phenylmethyl ester To a suspension of 6.1 g (29.8 mmol) of 2-amino-4,5-dihydroxybenzamide, monohydrochloride in 240 ml of absolute acetonitrile was added 17.8 g (89.4 mmol) of N-methyl-N-(trimethylsilyl)trifluoroacetamide to obtain a blue solution. After some minutes, a precipitate was formed. The mixture was stirred for 30 minutes at room temperature and then evaporated to dryness a high vacuum for 60 minutes. The crystalline residue was dissolved in 360 ml of absolute ethyl acetate (solution A). To a suspension of 6.56 g (29.8 mmol) of (S)-(2-oxo-3-azetidinyl)carbamic acid, phenylmethyl ester in 120 ml of absolute ethyl acetate was added 4.22 g (29.8 mmol) of chlorosulfonyl isocyanate. After stirring for 1 hour, the solution was cooled to 0° C. and 90 l of dichloromethane and 9.05 g (89.4 mmol) of triethylamine were added. (Solution B).

Solution B was added in four portions to solution A at 0° C. After stirring overnight at room temperature, ice was added, and after 30 minutes, the pH was brought to 2 with 3N hydrochloric acid. The phases were separated, the aqueous phase was extracted twice with ethyl acetate, and the combined organic phases were dried over magnesium sulfate. Evaporation and trituration of the residue with ether yielded 12.2 g of (S)-[1-[[[[2-(aminocarbonyl)-4,5-dihydroxyphenyl]amino]sulfonyl]amino]carbonyl]-2-oxo-3-azeidinyl]carbamic acid, phenylmethyl ester.

(F) (S)-3-Amino-N-[[[2-(aminocarbonyl)-4,5-dihydroxyphenyl]amino]sulfonyl]-2-oxo-1-azetidinecarboxamide, trifluoroacetate ester To a mixture of 73 ml of trifluoroacetic acid and 14.5 ml of thioanisole was added 11.8 g (23.9 mmol) of (S)-[1-[[[[2-(aminocarbonyl)-4,5-dihydroxyphenyl]amino]sulfonyl]amino]carbonyl]-2-oxo-3-azetidinyl]carbamic acid, phenylmethyl ester at 0° C. in several portions. After stirring overnight, 900 ml of ether was added under ice cooling, and the resulting crystals were filtered off, washed twice with ether and triturated with dischloromethane; yield: 8.75 g.

(G) [3S(Z)]-2-[[[1-(2-Amino-4-thiazolyl)-2-[[1-[[[[2-[2--(aminocarbonyl)-4,5-dihydroxyphenyl]amino]sulfonyl]amino]carbonyl]-2-oxo-3-azetidinyl]amino]-2-oxoethylidene]amino]oxy]-2-methylpropanoic acid, diphenylmethyl ester To a solution of 2.79 g (6.33 mmol) of (Z)-2-amino-α-[[1-(diphenylmethoxycarbonyl)-1-methylethoxy]imino]-4-thiazoleacetic acid and 1.92 g (19.0 mmol) of triethylamine in 65 ml of absolute dimethylformamide was added dropwise at −30° C. and under nitrogen protection 1.70 g (6.33 mmol) of diphenylchlorophosphate. After stirring for one hour, a solution of 3.0 g (6.33 mmol) of (S)-3-amino-N-[[[2-(aminocarbonyl)-4,5-dihydroxyphenyl]amino]sulfonyl]-2-oxo-1-azetidinecarboxamide, trifluoroacetate ester in 25 ml of dimethylformamide and, subsequently, 1.28 g (12.7 mmol) of triethylamine were added. After stirring for two hours at −10° C., and one additional hour at 0° C., the dimethylformamide was evaporated in vacuo and to the residue was added 50 ml of ice water and 100 ml of ethyl acetate. When the pH was adjusted to 1.5 with hydrochloric acid, an oil separated which was isolated and dissolved in acetone. The acetone was evaporated in vacuo and the residue triturated with ether to yield 1.90 g of crude [3S(Z)]-2-[[[1-(2-amino-4-thiazolyl)-2-[[1-[[[[ 2-[2-(aminocarbonyl)-4,5-dihydroxyphenyl]amino]sulfonyl]amino]carbonyl]-2-oxo-3-azetidinyl]amino]-2-oxoethylidene]amino]oxy]-2-methylpropanoic acid, diphenylmethyl ester.

The water-ethyl acetate phases were separated, the organic phase was washed with water, dried and evaporated to dryness to yield, after trituration with ether, another 2.81 g of crude [3S(Z)]-2-[[[1-(2-amino-4-thiazolyl)-2-[[1-[[[[2-[2-(aminocarbonyl)-4,5-dihydroxyphenyl]amino]sulfonyl]amino]carbonyl]-2-oxo-3- azetidinyl]amino]-2-oxoethylidene]amino]oxy]-2-methylpropanoic acid, diphenylmethyl ester. Total yield: 4.71 g.

(H)

[3S(Z)]-2-[[[1-(2-Amino-4-thiazolyl)-2-[[1-[[[[2-[2-(-aminocarbonyl)-4,5-dihydroxyphenyl]amino]sulfonyl-]amino]carbonyl]-2-oxo-3-azetidinyl]amino]-2-oxoethylidene]amino]-oxy]-2-methylpropanoic acid, disodium salt To a suspension of 1.83 g (2.38 mmol) of [3S(Z)]-2-[[-[1-(2-amino-4-thiazolyl)-2-[[1-[[[[2-[2-(aminocarbonyl)-4,5-dihydroxyphenyl]amino]sulfonyl]amino]carbonyl]-2-oxo-3-azetidinyl]amino]-2-oxoethylidene]amino]oxy]-2-methylpropanoic acid, diphenylmethyl ester in 3.6 ml of anisole was added dropwise at 0° C. 18 ml of trifluoroacetic acid. After stirring for 1.75 hours at 0° C., the excess trifluoroacetic acid and anisole were distilled off in vacuo. Ether was added to the residue and the resulting crystalline material was filtered off, washed with water and dried in vacuo (1.43 g). The trifluoroacetic acid salt was dissolved in 40 ml of water/acetone 1:1 and the pH was brought to 6.5 with 1N sodium hydroxide. Freeze drying yielded 1.45 g of crude product which was chromatographed on XAD under MPLC conditions with water as eluent; yield of pure freeze dried product: 0.26 g.

EXAMPLE 20

[3S(Z)]-2-[[[1-[(2-Amino-4-thiazolyl)-2-[[1-[[[[2-(2-bromo-4,5-dihydroxybenzoyl)hydrazino]sulfonyl]amino]-carbonyl]-2-oxo-3-azetidinyl]amino]-2-oxoethylidene]amino]oxy]-2-methylpropanoic acid, disodium salt (A)

(S)-[1-[[[[2-(2-Bromo-4,5-dihydroxybenzoyl)hydrazino]sulfonyl]amino]carbonyl]-2-oxoazetidinyl]carbamic acid, phenylmethyl ester To a suspension of 6.2 g (25 mmol) of 2-bromo-4,5-dihydroxybenzoic acid, hydrazide in 200 ml of ethyl acetate was added 14.9 g (75 mmol) of N-methyl-N-(trimethylsilyl)trifluoroacetamide and the mixture was stirred for one hour. The clear solution was evaporated to dryness and finally dried for five minutes at 60° C./0.01 mbar. The residue was dissolved in 100 ml of ethyl acetate (solution A).

To a solution of 5.5 g (25 mmol) of (S)-(2-oxo-3-azetidinyl)carbamic acid, phenylmethyl ester in 100 ml of ethyl acetate was added 3.55 g (25 mmol) of chlorosulfonyl isocyanate. After stirring for 30 minutes, the solution was cooled to 0° C. and 7.6 g (75 mmol) of triethylamine and 100 ml of dichloromethane were added. To this mixture, solution A was added dropwise at 0° C. After stirring overnight at room temperature, ice was added and the resulting precipitate was filtered off. 150 ml of ethyl acetate was added to the filtrate, the phases were separated and the water phase extracted once with ethyl acetate. The water phase was layered with 200 ml of ethyl acetate, the pH brought to 2 with 3N hydrochloric acid and after drying and evaporating the organic phase, 11.8 g of (S)-[1-[[[[2-(2-bromo-4,5-dihydroxybenzoyl)hydrazino]sulfonyl]amino]carbonyl]-2-oxoazetidinyl]carbamic acid, phenylmethyl ester was obtained; melting point 80°–100° C., dec.

(B)

(S)-3-Amino-N-[[2-(2-bromo-4,5-dihydroxybenzoyl)hydrazino]sulfonyl]-2-oxoazetidinecarboxamide, trifluoroacetate salt At room temperature, 2.29 g (4 mmol) of (S)-[1-[[[[2-(2-bromo-4,5-dihydroxybenzoyl)hydrazino]sulfonyl]amino]carbonyl]-2-oxoazetidinyl]carbamic acid, phenylmethyl ester was added to a mixture of 4.5 ml of trifluoroacetic acid and 1.6 g of thioanisole. After stirring overnight, 50 ml of ether was added and the resulting crystals were filtered off by suction, dried and triturated with 40 ml of dichloromethane. The crystals were filtered off again and dried in vacuo; yield: 1.9 g, melting point 157° C.

(C)

[3S(Z)]-2-[[[1-(2-Amino-4-thiazolyl)-2-[[1-[[[[2-(2-bromo-4,5-dihydroxybenzoyl)hydrazino]sulfonyl]amino]carbonyl]-2-oxo-3-azetidinyl]amino]-2-oxoethylidene]amino]oxy]-2-methylpropanoic acid, diphenylmethyl ester To a solution of 1.45 g (3.5 mmol) of (Z)-2-amino-α-[[1-(diphenylmethoxycarbonyl)-1-methylethoxy]imino]-4-thiazoleacetic acid and 1.0 g (9.9 mmol) of triethylamine in 60 ml of absolute dimethylfomamide was added dropwise at −30° C. and under nitrogen protection 0.8 g (3.3 mmol) of diphenylchlorophosphate in 15 ml of dimethylformamide. After stirring for one hour, 0.65 g (6.6 mmol) of triethylamine and 1.82 g (3.3 mmol) of (S)-3-amino-N-[[2-(2-bromo-4,5-dihydroxybenzoyl)hydrazino]sulfonyl]-2-oxoazetidinecarboxamide, trifluoroacetate salt were added. After stirring for two hours at −10° C. and another 1.5 hours at 0° C., the dimethylformamide was evaporated in vacuo. To the residue were added 150 ml of ethyl acetate and 60 ml of water, and the pH was adjusted to 1 with 3N hydrochloric acid. The phases were separated, the organic phase washed with dilute hydrochloric acid, water and brine and dried over magnesium sulfate. Evaporation of the solvent and trituration of the residue with ether yielded, after drying, 2.7 g of crude [3S(Z)]-2-[[[1--(2-amino-4-thiazolyl)-2-[[1-[[[[2-(2-bromo-4,5-dihydroxybenzoyl)hydrazino]sulfonyl]amino]carbonyl]-2-oxo-3-azetidinyl]amino]-2-oxoethylidene]amino]oxy]-2-methylpropanoic acid, diphenylmethyl ester, melting point 145°–158° C., dec.

(D)

[3S(Z)]-2-[[[1-(2-Amino-4-thiazolyl)-2-[[1-[[[[2-(2-bromo-4,5-dihydroxybenzoyl)hydrazino]sulfonyl]amino]carbonyl]-2-oxo-3-azetidinyl]amino]-2-oxoethylidene]amino]oxy]-2-methylpropanoic acid, disodium salt To a suspension of 2.6 g (3.0 mmol) of [3S(Z)]-2-[[-[1-(2-amino-4-thiazolyl)-2-[[1[[[[2-(2-bromo-4,5-dihydroxybenzoyl)hydrazino]sulfonyl]amino]carbonyl]-2-oxo-3-azetidinyl]amino]-2oxoethylidene]amino]oxy]-2-methylpropanoic acid, diphenylmethyl ester in 6 ml of anisole was added dropwise at 0° C. 12 ml of trifluoroacetic acid. After stirring for two hours, the excess trifluoroacetic acid and anisole were distilled off in vacuo. Ether was added to the residue and the resulting crystalline material was filtered off, washed with ether and dried in vacuo (1.56 g). The crude product was suspended in 20 ml of water and the pH was brought to 6.5 with 1N sodium hydroxide. After freeze drying of the obtained solution, the product (1.62 g) was chromatographed on XAD (under MPLC conditions) with water as eluent; yield of freeze dried product: 0.29 g; melting pint 227°–249° C., dec.

EXAMPLE 21

[3S(Z)]-2-[[[[3-[[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-4,5-dihydroxybenzoic acid, disodium salt (A)

[3S(Z)]-2-Amino-N-[1-[[[[3-[[(1,1-dimethylethoxy)carbonyl]amino]-2-oxo-1-imidazolidinyl]sulfonyl]amino]carbonyl]-2-oxo-3-azetidinyl]-α-(methoxyimino)-4-thiazoleacetamide, monosodium salt To a solution of 8.23 g (15 mmol) of (S)-[1-[[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt in 275 ml of dimethylformamide was added 4.1 g palladium on charcoal and hydrogen was bubbled through the mixture for 40 minutes. The catalyst was filtered off and to the filtrate was added a solution of 4.77 g (15 mmol) of (Z)-2-amino-α-(methoxyimino)-4-thiazoleacetic acid, N-hydroxybenzotriazole ester in 135 ml of dimethylformamide. After stirring overnight, the dimethylformamide was evaporated in vacuo and the residue triturated with ether. The resulting crystalline material was filtered off, washed with ether and dried in vacuo; yield: 9.85 g.

(B)

[3S(Z)]-2-Amino-N-[1-[[[(3-amino-2-oxo-1-imidazolidinyl)sulfonyl]amino]carbonyl]-2-oxo-3-azetidinyl]-α-(methoxyimino)-4-thiazoleacetamide, monosodium salt To a solution of 4.79 g (8 mmol) of [3S(Z)]-2-amino-N-[1-[[[[3-[[(1,1-dimethylethoxy)carbonyl]amino]-2-oxo-1-imidazolidinyl]sulfonyl]amino]carbonyl]-2-oxo-3-azetidinyl]-α-(methoxyimino)-4-thiazoleacetamide, monosodium salt in 15 ml of anisole was added dropwise 30.5 ml of trifluoroacetic acid at 0° C. After stirring for two hours, anisole and trifluoroacetic acid were distilled off and the residue was triturated with ether. The crystals were filtered off and dried to yield 4.26 g of crude material which was dissolved in methanol/water 1:1. The pH was adjusted to 6.5 with 1N sodium hydroxide and after the evaporation of the methanol, the aqueous solution was freeze dried; yield: 4.39 g. This material was chromagraphed in three portions (each 1.4 g) on XAD with water as eluent under MPLC conditions; yield of pure [3S(Z)]-2-amino-N-[1-[[[(3-amino-2-oxo-1imidazolidinyl)sulfonyl]amino]carbonyl]-2-oxo-3-azetidinyl]-α-(methoxyimino)-4-thiazoleacetamide, monosodium salt: 1.36 g.

(C)

[3S(Z)]-2-[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-4,5-dihydroxybenzoic acid, disodium salt To a solution of 0.68 g (1.5 mmol) of [3S(Z)]-2-amino-N-[1-[[[(3-amino-2-oxo-1-imidazolidinyl)sulfonyl]amino]carbonyl]-2-oxo-3-azetidinyl]-α-(methoxyimino)-4-thiazoleacetamide, monosodium salt in 12 ml of dimethylformamide was added 0.30 g (1.65 mmol) of 4,5-dihydroxyphthalic anhydride. After stirring overnight, the dimethylformamide was evaporated in vacuo and the residue was dissolved in water. The pH was adjusted to 6.5 with 1N sodium hydroxide, and after freeze drying of this solution, the crude material (1.23 g) was chromatographed on XAD under MPLC conditions with water as eluent; yield: 0.47 g. A second chromatography was necessary to obtain biologically pure material.

EXAMPLE 22

[3S(Z)]-2-[[[1-(2-Amino-4-thiazolyl)-2-[[1-[[[[2-[(3,4-dihydroxyphenyl)methylene]hydrazino]sulfonyl]amino]carbonyl]-2-oxo-3-azetidinyl]amino]-2-oxoethylidene]amino]oxy]-2-methylpropanoic acid, sodium salt and

[3S(Z)]-2-[[[1-(2-Amino-4-thiazolyl)-2-[[1-[[(hydrazinosulfonyl)amino]carbonyl]-2-oxo-3-azetidinyl]amino]-2-oxoethylidene]amino]oxy]-2-methylpropanoic acid, monosodium salt (A)

2-[(3,4-Dihydroxyphenyl)methylene]hydrazinecarboxylic acid, 1,1-dimethylethyl ester To a solution of 5.30 g (40 mmol) of (t-butoxycarbonyl)hydrazine in 40 ml of 80% aqueous ethanol was added a solution of 5.52 g of 3,4-dihydroxybenzaldehyde in 40 ml of the same solvent. After stirring for three hours at room temperature, the mixture was clarified with charcoal, filtered and the filtrate evaporated in vacuo. The residue was triturated with petroleum ether, filtered off by suction and dried in vacuo; yield: 8.5 g.

(B) 4-(Hydrazonomethyl)-1,2-benzenediol, trifluoroacetate salt

A suspension of 29.01 g (115 mmol) of 2-[(3,4-dihydroxyphenyl)methylene]hydrazinecarboxylic acid, 1,1-dimethylethyl ester in 150 ml of dichloromethane was cooled to −10° C., and 250 ml of trifluoroacetic acid was added. The resulting clear solution was stirred for two hours at −10° C. and the excess trifluoroacetic acid evaporated in vacuo. The residue was triturated with a mixture of ether and petroleum ether (1:1), filtered off by suction and dried in vacuo; yield: 25.4 g.

(C)

(S)-[1-[[[[2-[(3,4-Dihydroxyphenyl)methylene]hydrazino]sulfonyl]amino]carbonyl]-2-oxo-3-azetidinyl]-carbamic acid, phenylmethyl ester To a suspension of 7.99 g (30 mmol) of 4-(hydrazonomethyl)-1,2-benzenediol, trifluoroacetate salt in 60 ml of ethyl acetate were added 11.13 ml (60 mmol) of N-methyl-N-(trimethylsilyl)trifluoroacetamide and 4.18 ml (30 mmol) of triethylamine. The mixture was stirred for one hour at 60° C., and the solvent and most of the N-methyltrifluoroacetamide were evaporated in vacuo at 60° C. The resulting residue was suspended in 45 ml of ethyl acetate (solution A).

To a suspension of 6.61 g (30 mmol) of (S)-(2-oxo-3-azetidinyl)carbamic acid, phenylmethyl ester in 90 ml of ethyl acetate was added 2.62 ml (30 mmol) chlorosulfonyl isocyanate, and the mixture was stirred for one hour at room temperature. After the addition of 45 ml of dichloromethane, the solution was cooled to 0° C., and 12.54 ml (90 mmol) of triethylamine was added, followed by solution A. The mixture was stirred over the weekend at room temperature and the precipitate filtered off by suction. To the filtrate were added 100 ml of ice water, and the mixture was washed two times with ethyl acetate. The aqueous phase was adjusted to pH 2 by adding 2N hydrochloric acid and extracted three times with ethyl acetate. The organic layer was dried over magnesium sulfate, filtered and evaporated in vacuo. The residue was triturated with ether, filtered off by suction and dried in vacuo; yield: 5.58 g.

(D)

(S)-3-Amino-N-[[2-[(3,4-dihydroxyphenyl)-methylene]-hydrazino]sulfonyl]-2-oxo-1-azetidinecarboxamide, trifluoroacetate salt A mixture of 22 ml of trifluoroacetic acid and 5.8 ml of thioanisole was cooled to 0° C., and 5.5 g (11.5 mmol) of (S)-[1-[[[[2-[(3,4-dihydroxyphenyl)methylene]hydrazino]sulfonyl]amino]carbonyl]-2-oxo-3-azetidinyl]]-carbamic acid, phenylmethyl ester were added. After stirring overnight at room temperature, the excess trifluoroacetic acid was evaporated in vacuo and the residue triturated with ether. The trifluoroacetic acid salt was filtered off by suction and dried in vacuo; yield: 2.64 g.

(E)

[3S(Z)]-2-[[[1-(2-Amino-4-thiazolyl)-2-[[1-[[[[2-[(3,4-dihydroxyphenyl)methylene]hydrazino]sulfonyl]amino]carbonyl]-2-oxo-3-azetidinyl]amino]-2-oxoethylidene]amino]oxy]-2-methylpropanoic acid, diphenylmethyl ester 2.46 g (5.6 mmol) of (Z)-2-amino-α-[[1-(diphenylmethoxycarbonyl)-1-methylethoxy]imino]-4-thiazoleacetic acid was dissolved in 70 ml of dimethylformamide, and the solution was cooled to −30° C. At this temperature, 2.34 ml (16.8 mmol) of triethylamine and 1.16 ml (5.6 mmol) of diphenylchlorophosphate were added. After stirring for one hour, 1.56 ml (11.2 mmol) of triethylamine and 2.56 g (5.6 mmol) of (S)-3-amino-N-[[2-[(3,4-dihydroxyphenyl)methylene]hydrazino]sulfonyl]-2-oxo-1-azetidinecarboxamide, trifluoroacetate salt were added. The mixture was stirred for two hours at −10° C. and one hour at 0° C. After evaporation of the solvent in vacuo, the residue was dissolved in a mixture of ethyl acetate and water. The pH was adjusted to 2 by adding 2N hydrochloric acid. A small amount of oil was formed (0.74 g) which was separated. The aqueous phase was extracted three times with ethyl acetate. The combined organic layers were washed once with 1N hydrochloric acid, twice with water and dried over magnesium sulfate. After filtration, the solvent was evaporated in vacuo and the residue triturated with petroleum ether; yield: 3.12 g. Since the TLC of this material was identical with that of the oil which separated during acidification, both the solid and the oily material were combined; total yield: 3.84 g.

(F)

[3S(Z)]-2-[[[1-(2-Amino-4-thiazolyl)-2-[[1-[[[[2-[(3,4-dihydroxyphenyl)methylene]hydrazino]sulfonyl]amino]carbonyl]-2-oxo-3-azetidinyl]amino]-2-oxoethylidene]amino]oxy]-2-methylpropanoic acid, sodium salt and
[3S(Z)]-2-[[[1-(2-Amino-4-thiazolyl)-2-[[1-[[(hydrazinosulfonyl)amino]carbonyl]-2-oxo-3-azetidinyl]amino]-2-oxoethylidene]amino]oxy]-2-methylpropanoic acid, monosodium salt 3.84 g (5.3 mmol) of [3S(Z)]-2-[[[1-(2-amino-4-thiazolyl)-2-[[1-[[[[2-[(3,4-dihydroxyphenyl)methylene]hydrazino]sulfonyl]amino]carbonyl]-2-oxo-3-azetidinyl]amino]-2-oxoethylidene]amino]oxy]-2-methylpropanoic acid, diphenylmethyl ester was suspended in 8 ml of anisole. After cooling to −10° C., 40 ml of trifluoroacetic acid was added, and the mixture was stirred for one hour. 100 ml of ether was added, and the precipitate was filtered off by suction. The product was dissolved in methanol-water, and the pH adjusted to 6.5 by adding 2N sodium hydroxide. The methanol was evaporated in vacuo and the aqueous phase freeze dried. The resulting crude product (2.26 g) was first chromatographed on HP-20 (water) and further purified by MPLC on XAD; yield: 90 mg very impure [3S(Z)]-2-[[[1-(2-amino-4-thiazolyl)-2-[[1-[[[[2-[(3,4-dihydroxyphenyl)methylene]hydrazino]sulfonyl]amino]carbonyl]-2-oxo-3-azetidinyl]amino]-2-oxoethylidene]amino]oxy]-2-methylpropanoic acid, sodium salt and 120 mg of [3S(Z)]-2-[[[1-(2-amino-4-thiazolyl)-2-[[1-[[(hydrazinosulfonyl)amino]carbonyl]-2-oxo-3-azetidinyl]amino]-2-oxoethylidene]amino]oxy]-2-methylpropanoic acid, monosodium salt.

EXAMPLE 23

[3S(Z)]-2-[[[1-(2-Amino-4-thiazolyl)-2-[[1-[[[[[3-(3,4-dihydroxyphenyl)-2-oxo-1-imidazolidinyl]carbonyl]amino]sulfonyl]amino]carbonyl]-2-oxo-3-azetidinyl]amino]-2-oxo-ethylidene]amino]oxy]-2-methylpropanoic acid, disodium salt (A)

1-Chloro-2-[[[(3,4-dimethoxyphenyl)amino]carbonyl]amino]ethane

To a solution of 51.9 g (0.34 mol) of 3,4-dimethoxyaniline in 500 ml of ethyl acetate was added dropwise a solution of 35.8 g (0.34 mol) of 2-chloroethylisocyanate in 100 ml of ethyl acetate. The reaction mixture was stirred for one hour at ambient temperature and the precipitate filtered off by suction (crop 1). The filtrate was evaporated to dryness and the resulting residue washed with ether (crop 2). The two crops were combined and dried in vacuo; yield: 83.7 g, melting point 117° C.

(B) 1-(3,4-Dimethoxyphenyl)-2-imidazolidinone

To a solution of 82.6 g (0.32 mol) of 1-chloro-2-[[[(3,4-dimethoxyphenyl)amino]carbonyl]amino]ethane in 800 ml of ethanol was added dropwise a solution of 21.5 g (0.383 mol) of potassium hydroxide in 400 ml of ethanol. The mixture was stirred for two days at room temperature and the precipitate filtered off by suction. The crude product was recrystallized from 1.5 l of ethyl acetate containing 10% methanol; yield, 52.5 g; melting point 168° C.

(C)

1-(Aminocarbonyl)-3-(3,4-dimethoxyphenyl)-2-imidazolidinone

A solution of 13.33 g (60 mmol) of 1-(3,4-dimethoxyphenyl)-2-imidazolidinone in 150 ml of ethyl acetate was cooled to 0° C., and 8.92 g (63 mmol) of chlorosulfonylisocyanate was added dropwise. The mixture was stirred for one hour at room temperature. To the resulting thick suspension was added 50 ml of water, and the mixture was stirred until two clear layers were formed. The aqueous phase was separated and stored in the refrigerator overnight. The precipitate was filtered off by suction, washed with water and dried in vacuo; yield: 11.04 g; melting point 240° C.

(D)
1-(Aminocarbonyl)-3-(3,4-dihydroxyphenyl)-2-imidazolidinone

A solution of 14 g (52.8 mmol) of 1-(aminocarbonyl)-3-(3,4-dimethoxyphenyl)-2-imidazolidinone in 700 ml of dichloromethane was cooled to −78° C., and 39.7 g (158 mmol) of boron tribromide was added dropwise. The dry-ice bath was removed and the reaction mixture was stirred overnight at ambient temperature. The mixture was cooled to 0° C., and 20 ml of water was added dropwise. The precipitate was filtered off by suction and stirred with water for one hour. The product was filtered off and dried in vacuo; yield: 8.51 g; melting point >250° C.

(E)
(S)-[1-[[[[[3-(3,4-dihydroxyphenyl)-2-oxo-1-imidazolidinyl]carbonyl]amino]sulfonyl]amino]carbonyl]-2-oxo-3-azetidinyl]carbamic acid, phenylmethyl ester, monosodium salt A mixture of 8.51 g (35.87 mmol) of 1-(aminocarbonyl)-3-(3,4-dihydroxyphenyl)-2-imidazolidinone and 28.60 g (143.5 mmol) of N-methyl-N-(trimethylsily)trifluoroacetamide in 300 ml of ethyl acetate was stirred for one hour at 60° C. The resulting clear solution was evaporated in vacuo at 60° C. and the residue dissolved in 100 ml of ethyl acetate (solution A).

To a suspension of 7.90 g (35.87 mmol) of (S)-(2-oxo-3-azetidinyl)carbamic acid, phenylmethyl ester in 300 ml of ethyl acetate was added 5.08 g (35.87 mmol) of chlorosulfonyl isocyanate. After stirring for one hour at room temperature solution A was added. The mixture was stirred overnight at room temperature and washed with brine. 100 ml of water was added, and the pH was adjusted to 6.5 by adding 2N sodium hydroxide. An oil was formed which was separated and triturated with ether to afford 15.25 g of (S)-[1-[[[[[3-(3,4-dihydroxyphenyl)-2-oxo-1-imidazolidinyl]carbonyl]amino]sulfonyl]amino]carbonyl]-2-oxo-3-acetidinyl]carbamic acid, phenylmethyl ester, monosodium salt.

The aqueous phase was acidified to pH 2 with hydrochloric acid and extracted three times with ethyl acetate. The combined organic layers were washed with brine, dried over sodium sulfate and evaporated in vacuo. The residue was triturated with ether and filtered off by suction.

(F)
(S)-3-Amino-N-[[[[3-(3,4-dihydroxyphenyl)-2-oxo-1-imidazolidinyl]carbonyl]amino]sulfonyl]-2-oxo-1-azetidinecarboxamide, trifluoroacetate salt A mixture of 20 ml of thioanisole and 75 ml of trifluoroacetic acid was cooled to 0° C. and 15.25 g of (S)-[1-[[[[[3-(3,4-dihydroxyphenyl)-2-oxo-1-imidazolidinyl]-carbonyl]amino]sulfonyl]amino]carbonyl]-2-oxo-3-azetidinyl]carbamic acid, phenylmethyl ester, monosodium salt was added. After stirring overnight at room temperature, the excess trifluoroacetic acid was evaporated in vacuo and the residue triturated with ether. The precipitate was filtered off by suction, washed with ether, and dried in vacuo; yield: 15.69 g.

(G)
[3S(Z)]-2-[[[1-(2-Amino-4-4-thiazolyl)-2-[[1-[[[[[3-(3,4-dihydroxyphenyl)-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester A solution of 7.79 g (17.78 mmol) of (Z)-2-amino-α-[[1-(diphenylmethoxycarbonyl)-1-methylethoxy]imino]-4-thiazoleacetic acid in 200 ml of dimethylformamide was cooled to −30° C., and 5.40 g (53.33 mmol) of triethylamine was added, followed by 4.78 g (17.78 mmol) of diphenylchlorophosphate. After stirring for one hour at −30° C., 3.60 (35.55 mmol) of triethylamine and 10.0 g (17.78 mmol) of (S)-3-amino-N-[[[[3-(3,4-dihydroxyphenyl)-2-oxo-1-imidazolidinyl]carbonyl]amino]sulfonyl]-2-oxo-1-azetidinecarboxamide, trifluoroacetate salt were added. The mixture was stirred for two hours at −10° C. and for 1.5 hours at 0° C. The solvent was evaporated in vacuo, the residue dissolved in a mixture of ethyl acetate and water and adjusted to pH 1.5 by the addition of 2N hydrochloric acid. An oil was formed which was separated and triturated with ether. The precipitate was filtered off by suction, washed with ether and dried in vacuo; yield: 10.71 g.

(H)
[3S(Z)]-2-[[[1-(2-Amino-4-thiazolyl)-2-[[1-[[[[[3-(3,4-dihydroxyphenyl)-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, disodium salt A suspension of 10.7 g (12.6 mmol) of [3S(Z)]-2-[[[1-(-2-amino-4-thiazolyl)-2-[[1-[[[[[3-(3,4-dihydroxyphenyl)-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester in 21.4 ml of anisole was cooled to −10° C. and 110 ml of trifluoroacetic acid was added. After stirring for one hour at −10° C., the excess trifluoroacetic acid was evaporated and the residue triturated with ether. The precipitate was filtered off by suction and dissolved in a mixture of methanol and water. The pH was adjusted to 6.5 by adding 2N sodium hydroxide. Methanol was evaporated in vacuo and the aqueous solution freeze dried to afford 9.77 g of crude [3S(Z)]-2-[[[1-(2-amino-4-thiazolyl)-2-[[1-[[[[[3-(3,4-dihydroxyphenyl)-2-oxo-1-imidazolidinyl]carbonyl]amino]sulfonyl]amino]carbonyl]-2-oxo-3-azetidinyl]amino]-2-oxoethylidene]amino]oxy]-2-methylpropanoic acid, disodium salt. The crude product was purified three times by MPLC on XAD (water); yield: 60 mg, melting point >250° C.

EXAMPLE 24

[3S(Z)]-2-[[[1-[(2-Amino-4-thiazolyl)-2-[[1-[[[2-[(3,4-dihydroxyphenyl)amino]sulfonyl]amino]carbonyl]-2-oxo-3-azetidinyl]amino]-2-oxoethylidene]amino]oxy]-2-methylpropanoic acid, disodium salt (A)
(S)-[1-[[[[(3,4-Dihydroxyphenyl)amino]sulfonyl]amino]carbonyl]-2-oxo-3-azetidinyl]carbamic acid, phenylmethyl ester 16.27 g (81.7 mmol) of N-methyl-N-(trimethylsilyl)-trifluoroacetamide was added to a solution of 9.76 g (40.8 mmol) of 4-amino-1,2-benzenediol, trifluoroacetate salt in 100 ml of ethyl acetate, and the mixture was stirred for one hour at room temperature. The solvent and most of the N-methyltrifluoroacetamide were evaporated at 60° C. The residue was dissolved in 100 ml of ethyl acetate (solution A).

To a suspension of 8.99 g (40.8 mmol) of (S)-(2-oxo-3-azetidinyl)carbamic acid, phenylmethyl ester in 100 ml of ethyl acetate was added 5.78 g (40.8 mmol) of chlorosulfonyl isocyanate, and the mixture was stirred for one hour at room temperature. After the addition of 100 ml of dichloromethane, the solution was cooled to 0° C. 16.52 g (163.3 mmol) of triethylamine and, subsequently, solution A were added. The resulting mixture was stirred overnight at room temperature. After addition of 200 ml of ice water, the pH was adjusted to 2 by adding 2N hydrochloric acid. The organic layer was separated and the aqueous phase extracted three times with ethyl acetate. The combined organic layers were washed with brine and dried over magnesium sulfate. The solvent was removed in vacuo and the residue triturated with petroleum ether; yield: 11.40 g.

(B)

(S)-Amino-N-[[(3,4-dihydroxyphenyl)amino]sulfonyl]-2-oxo-1-azetidinecarboxamide, trifluoroacetate salt A mixture of 10 ml of thioanisole and 40 ml of trifluoroacetic acid was cooled to 0° C., and 8.36 g (20 mmol) of (S)-[1-[[[[(3,4-dihydroxyphenyl)amino]sulfonyl]amino]carbonyl]-2-oxo-3-azetidinyl]carbamic acid, phenylmethyl ester was added. The reaction mixture was stirred overnight at room temperature and the trifluoroacetic acid evaporated in vacuo. The oily residue was triturated with ether and the precipitate filtered off by suction. The crude product was washed with ether, dichloromethane and isopropanol and dried in vacuo; yield: 6.86 g.

(C)

[3S(Z)]-2-[[[1-(2-amino-4-thiazolyl)-2-[[1-[[[[(3,4-dihydroxyphenyl)amino]sulfonyl]amino]carbonyl]-2-oxo-3-azetidinyl]amino]-2-oxoethylidene]amino]oxy]-2-methylpropanoic acid, diphenylmethyl ester A solution of 6.73 g (15.3 mmol) of (Z)-2-amino-α-[[1-(diphenylmethoxycarbonyl)-1-methylethoxy]imino]-4-thiazoleacetic acid in 100 ml of dimethylformamide was cooled to −30° C. 4.66 g (46 mmol) of triethylamine and 4.12 g of (15.3 mmol) diphenylchlorophosphate were added. After stirring for one hour at −30° C., 3.10 g (30.7 mmol) of triethylamine was added, followed by 6.60 g (15.3 mmol) of (S)-amino-N-[[(3,4-dihydroxyphenyl)amino]sulfonyl]-2-oxo-1-azetidinecarboxamide, trifluoroacetate salt. The mixture was stirred for two hours at −10° C. and for 90 minutes at 0° C. The solvent was evaporated in vacuo, and the oily residue dissolved in a mixture of ethyl acetate and water and adjusted to pH 1.5 by the addition of 2N hydrochloric acid. The organic layer was separated and the aqueous phase extracted three times with ethyl acetate. The combined organic layers were dried over magnesium sulfate, and the solvent was evaporated in vacuo. The residue was triturated with ether, filtered off by suction and dried in vacuo; yield: 9.76 g.

(D)

[3S(Z)]-2-[[[1-[(2-Amino-4-thiazolyl)-2-[[1-[[[2-[(3,4-dihydroxyphenyl)amino]sulfonyl]amino]carbonyl]-2-oxo-3-azetidinyl]amino]-2-oxoethylidene]amino]oxy]-2-methylpropanoic acid, disodium salt A suspension of 9.60 g (13 mmol) of [3S(Z)]-2-[[[1-(2--amino-4-thiazolyl)-2-[[1-[[[[(3,4-dihydroxyphenyl)amino]sulfonyl]amino]carbonyl]-2-oxo-3-azetidinyl]amino]-2-oxoethylidene]amino]oxy]-2-methylpropanoic acid, diphenylmethyl ester in 18 ml of anisole was cooled to −10° C., and 95 ml of trifluoroacetic acid was added. After stirring for one hour at −10° C., 200 ml of ether was added. The precipitate was filtered off by suction and dissolved in a mixture of methanol and water. The pH was adjusted to 6.5 by adding 2N sodium hydroxide. Methanol was evaporated in vacuo and the aqueous phase freeze dried to afford 5.95 g of (74%) crude [3S(Z)]-2-[[[1-(2-amino-4-thiazolyl)-2-[[1-[[[[(3,4-dihydroxyphenyl)amino]sulfonyl]amino]carbonyl]-2-oxo-3-azetidinyl]amino]-2-oxoethylidene]amino]oxy]-2-methylpropanoic acid, diphenylmethyl ester. The crude product was purified three times by MPLC on XAD (water).

EXAMPLE 25

[3S(Z)]-2-[[[1-(2-Amino-4-thiazolyl)-2-[[1-[[[3-(3,4-dihydroxyphenyl)-2-oxo-1-imidazolidinyl]sulfonyl]amino]amino]carbonyl]-2-oxo-3-azetidinyl]amino]-2-oxoethylidene]amino]oxy]-2-methylpropanoic acid, disodium salt (A)

1-[3,4-Bis[(trimethylsilyl)oxy]phenyl]-3-(trimethylsilyl)-2-imidazolidinone

To a solution of 3.4 g (17.5 mmol) of 1-(3,4-dihydroxyphenyl)-2-imidazolidinone in 10 ml of ethyl acetate was added 7.6 g (70 mmol) of chlorotrimethylsilane, and subsequently 7.0 g (70 mmol) of triethylamine. After stirring overnight at room temperature, the precipitate was filtered off under nitrogen and the filtrate evaporated to dryness in vacuo; yield: 7.14 g.

(B)

(S)-[1-[[[[3-(3,4-Dihydroxyphenyl)-2-oxo-1-imidazolidinyl]sulfonyl]amino]carbonyl]-2-oxo-3-azetidinyl]carbamic acid, phenylmethyl ester To a suspension of 3.9 g (17.8 mmol) of (S)-(2-oxo-3-azetidinyl)carbamic acid, phenylmethyl ester in 30 ml of ethyl acetate was added 2.5 g (17.8 mmol) of chlorosulfonyl isocyanate. The reaction mixture was stirred for one hour at room temperature and a solution of 7.14 g (17.8 mmol) of 1-[3,4-bis[(trimethylsilyl)oxy]phenyl]-3-(trimethylsilyl)-2-imidazolidinone in 30 ml of ethyl acetate was added dropwise. After stirring overnight at room temperature, the mixture was washed with brine, dried over sodium sulfate and evaporated in vacuo; yield: 8.46 g.

(C)

(S)-3-Amino-N-[[3-(3,4-dihydroxyphenyl)-2-oxo-1-imidazolidinyl]sulfonyl]-2-oxo-1-azetidinecarboxamide, trifluoroacetate salt A mixture of 16 ml of trifluoroacetic acid and 4 ml of thioanisole was cooled to 0° C., and 4 g (7.7 mmol) of (S)-[1-[[[[3-(3,4-dihydroxyphenyl)-2-oxo-1-imidazolidinyl]sulfonyl]amino]carbonyl]-2-oxo-3-azetidinyl]carbamic acid, phenylmethyl ester was added. The mixture was stirred overnight at room temperature, evaporated in vacuo, and the residue triturated with ether. The precipitate was filtered off by suction, washed with ether, dichlormethane and isopropanol and dried in vacuo; yield: 3.19 g.

(D)

[3S(Z)]-2-[[[1-(2-Amino-4-thiazolyl)-2-[[1-[[[[3-(3,4-dihydroxyphenyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a solution of 6.2 g (14.2 mmol) of (Z)-2-amino-α-[[1-(diphenylmethoxycarbonyl)-1-methylethoxy]imino]-4-thiazoleacetic acid in 200 ml of dimethylformamide was added 4.3 g (42.6 mmol) of triethylamine. The mixture was cooled to −30° C., and 3.8 g (14.2 mmol) of diphenylchlorophosphate was added. After stirring for one hour at −30° C., 2.9 g (28.4 mmol) of triethylamine and 7.1 g (14.2 mmol) of (S)-3-amino-N-[[3-(3,4-dihydroxyphenyl)-2-oxo-1-imidazolidinyl]sulfonyl]-2-oxo-1-azetidinecarboxamide, trifluoroacetate salt were added. The mixture was stirred for two hours at −10° C. and for one hour at 0° C. The solvent was evaporated in vacuo and the residue dissolved in a mixture of ethyl acetate and water. The solution was adjusted to pH 1.5 by the addition of 2N hydrochloric acid. An oil was formed which was separated and triturated with ether to afford solid [3S(Z)]-2-[[[1-(2-amino-4-thiazolyl)-2-[[1-[[[[3-(3,4-dihydroxyphenyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester; yield: 11.2 g.

(E)

[3S(Z)]-2-[[[1-(2-Amino-4-thiazolyl)-2-[[1-[[[[3-(3,4-di hydroxyphenyl)-2-oxo-1-imidazolidinyl]sulfonyl]amino]amino]carbonyl]-2-oxo-3-azetidinyl]amino]-2-oxoethylidene]amino]oxy]-2-methylpropanoic acid, disodium salt A solution of 11.1 g (13.5 mmol) of [3S(Z)]-2-[[[1-(2-amino-4-thiazolyl)-2-[[1-[[[[3-(3,4-dihydroxyphenyl)-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester in 22.2 ml of anisole was cooled to −10° C., and 111 ml of trifluoroacetic acid was added. The mixture was stirred for one hour at −10° C. and the excess trifluoroacetic acid evaporated in vacuo. The residue was triturated with ether, the precipitate filtered off by suction and dissolved in a mixture of methanol and water. The solution was adjusted to pH 6.5 by the addition of 2N sodium hydroxide and, after the evaporation of the methanol, freeze dried. The resulting crude compound (10 g) was purified by MPLC on XAD (water) to afford 0.32 g of still impure material. 0.24 g of this material was further purified by a second MPLC on XAD (water); yield: 34 mg, melting point 247° C., dec.

EXAMPLE 26

[3S(Z)]-2-[[[1-(2-Amino-4-thiazolyl)-2-[[1-[[[[2-(2,3-dihydroxybenzoyl)hydrazino]sulfonyl]amino]carbonyl]-2-oxo-3-azetidinyl]amino]-2-oxoethylidene]amino]oxy]-2-methylpropanoic acid, disodium salt (A) 2,3-bis(Acetyloxy)benzoic acid 2,3-Dihydroxybenzoic acid (25 g) was suspended in 100 ml of water. After cooling to 5° C., a solution of 20.3 g of sodium hydroxide in 50 ml of water was dropped in. To the formed dark solution was added dropwise 38.2 ml of acetic anhydride. After stirring for 1 hour, 2N hydrochloric acid was added until the pH was 2.5. Product crystallized from the solution and was isolated by filtration, washed with 50 ml of ice water and dried in vacuo over phosphorous pentoxide. 31 g of product (beige crystals) was obtained after recrystallization from toluene; melting point 134° C. (dec.).

(B) 2,3-bis(Acetyloxy)benzoyl chloride 24 g of 2,3-bis(acetyloxy)benzoic acid was suspended in 100 ml of dichloromethane and, at −10° C., 23 g of phosphorous pentachloride was added. The hydrogen chloride gas that formed was removed The resulting clear solution was then evaporated in an oil-pump vacuum yielding a brown honey. This was dissolved in 300 ml of petroleum ether and filtered over active carbon. After distilling off the solvent, the title compound was obtained in the form of white crystals (25.1 g); melting point 97°–99° C. (dec.)

(C) [2,3-bis(Acetyloxy)benzoyl]hydrazinecarboxylic acid, t-butyl ester

N-[(t-Butyloxy)carbonyl]hydrazine (12 g) and 10 g of triethylamine were dissolved in 200 ml of dichloromethane and, at 0° C., 24 g of 2,3-bis(acetyloxy)benzoyl chloride in 50 ml of dichloromethane was added dropwise with stirring (30 minutes). After continuous stirring for one hour, the reaction mixture was extracted with 200 ml of ice water, 50 ml of 1% sodium bicarbonate and 100 ml of 5% citric acid. The organic phase was then washed with 100 ml of water, dried over sodium sulfate, and the solvent distilled off. The remaining oil crystallized after stirring with hexane. The result was beige crystals, 26.3 g; melting point 117° C.

(D) (2,3-Dihydroxybenzoyl)hydrazinecarboxylic acid, t-butyl ester

[2,3-bis(Acetyloxy)benzoyl]hydrazinecarboxylic acid, t-butyl ester (25 g) was dissolved in 100 ml of methanol containing 6 g of ammonia. After standing over 24 hours at 0° C., the solvent was removed in vacuo and the residue stirred with 100 ml of ice water yielding (2,3-dihydroxybenzoyl)hydrazinecarboxylic acid, t-butyl ester as beige crystals, 17.8 g; melting point 158°–160° C.

(E) (2,3-Dihydroxybenzoyl)hydrazine, trifluoroacetate salt (2,3-Dihydroxybenzoyl)hydrazine carboxylic acid, t-butyl ester (17 g) was dissolved in 50 ml of trifluoroacetic acid/anisole (4:1) at 0° C. and stirred for 30 minutes. Diethyl ether (200 ml) was added, and (2,3-dihydroxybenzoyl)hydrazine, trifluoroacetate salt crystallized from the solution. After washing with ether and drying over silica gel, 17.2 g of (2,3-dihydroxybenzoyl)- hydrazine, trifluoroacetate salt were obtained as beige, fine crystals; melting point 212° C.

(F)

(S)-3-[[(Phenylmethoxy)carbonyl]amino]-N-[[2-(2,3-dihydroxybenzoyl)hydrazino]sulfonyl]-2-oxo-1-azetidinecarboxamide (2,3-Dihydroxybenzoyl)hydrazine, trifluoroacetate salt (2.82 g) was suspended in 50 ml of acetonitrile and 13.5 g of N-methyl-N-(trimethylsilyl)trifluoroacetamide were added. After stirring for one hour at 40° C., the solvent and trifluoroacetic acid, trimethylsilyl ester formed were distilled off in vacuo. The remaining oil was dissolved again in 50 ml of dried acetonitrile, cooled to 0° C. and added dropwise to a solution of 3.48 g of an adduct of chlorosulfonylisocyanate and (S)-(2-oxo-3-azetidinyl)carbamic acid, phenylmethyl ester in 100 ml of acetonitrile at 0° C. with stirring. After continuous stirring overnight, the solvent was distilled off in vacuo and the residue stirred (1 hour) with 200 ml of isopropanol. (S)-3-[[(Phenylmethoxy)carbonyl]amino]-N-[[2-(2,3-dihydroxybenzoyl)hydrazino]sulfonyl]-2-oxo-1-azetidinecarboxamide precipitated from the solution. Isolation by filtration and washing with ether yielded 3.87 g of white powder.

(G)

(S)-3-Amino-N-[[2-(2,3-dihydroxybenzoyl)hydrazino]-sulfonyl]-2-oxo-1-azetidinecarboxamide, trifluoroacetate salt At room temperature, 3.7 g of (2,3-dihydroxybenzoyl)hydrazine, trifluoroacetate salt was stirred in 50 ml of trifluoroacetic acid/anisole (3:2) overnight. The product was precipitated with ether/isopropanol (8:2) from the reaction solution. Beige powder was obtained after washing with ether and drying over silica gel; melting point 167°-169° C. (dec.).

(H)

[3S(Z)]-2-[[[1-(2-Amino-4-thiazolyl)-2-[[1-[[[[2-(2,3-dihydroxybenzoyl)hydrazino]sulfonyl]amino]carbonyl]-2-oxo-3-azetidinyl]amino]-2-oxoethylidene]amino]oxy]-2-methylpropanoic acid, disodium salt.

(Z)-2-Amino-α-[[1-(diphenylmethoxycarbonyl)-1-methylethoxy]imino]-4-thiazoleacetic acid (2.2 g) was dissolved in 50 ml of dimethylformamide; 1.5 ml of triethylamine was added and, after cooling at −30° C., 1.35 g of diphenylchlorophosphate was dropped into the solution. After stirring for one hour at −30° C. again, 1 ml of triethylamine was added followed by a solution of 2.37 g of (S)-3-amino-N-[[2-(2,3-dihydroxybenzoyl)hydrazino]sulfonyl]-2-oxo-1-azetidinecarboxamide, trifluoroacetate salt in 10 ml of dimethylformamide. After stirring for two hours at −10° C. and one hour at 0° C., the dimethylformamide was evaporated in vacuo. The oily residue was dissolved in 50 ml of ethyl acetate and 40 ml of ice water, stirred for 5 minutes and the pH was then adjusted to 2.0. The organic phase was separated and the water phase was twice extracted, each time with 50 ml of ethyl acetate. The organic phases were dried over sodium sulfate and concentrated to 20 ml. This was dropped into 200 ml ether. A precipitate of 3.3 g was obtained.

This was suspended in 10 ml of anisole and, at −10° C., 35 ml of trifluoroacetic acid was dropped in under stirring. The clear solution formed after 45 minutes of stirring was dropped into 200 ml of ether and a crude precipitate of 1.7 g of crude product was obtained (free acid), 1 g of this material was suspended in 5 ml of ice water and the pH was adjusted to 6.5 with sodium bicarbonate. The solution was filtered and chromatographed on HP-20 with water as an eluent, yielding 280 mg of the title product.

What is claimed is:
1. A compound having the formula

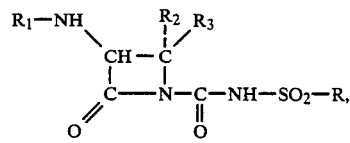

or a pharmaceutically acceptable salt thereof wherein R is

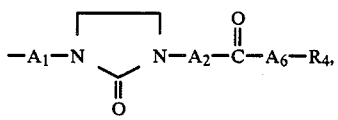

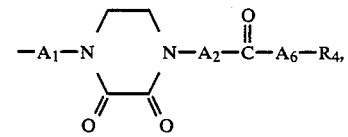

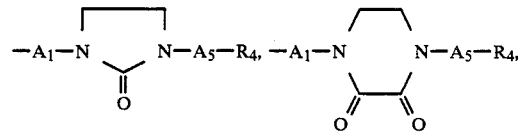

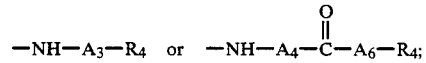

$R_1$ is an acyl group derived from a carboxylic acid;
$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl,

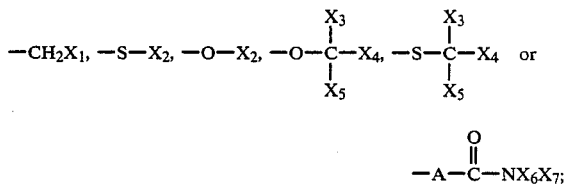

$R_4$ is

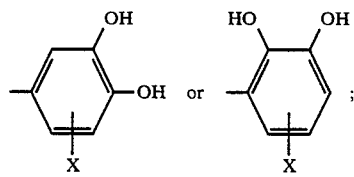

X is hydrogen, halogen, sulfo, carboxyl, aminosulfonyl, carbamoyl, cyano, alkyl, alkanoyl or alkoxycarbonyl;

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

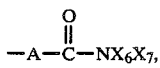

—S—$X_2$, or —O—$X_2$;

$X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

A is —CH=CH—, —(CH$_2$)$_m$—, —(CH$_2$)$_m$—O—, —(CH$_2$)$_m$—NH— or —CH$_2$—S—CH$_2$—;

m is 0, 1 or 2;

$A_1$ is a single bond,

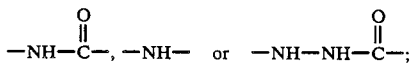

$A_2$ is a single bond,

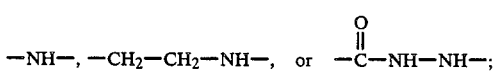

$A_3$ is

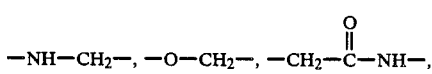

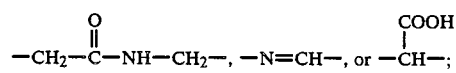

$A_4$ is

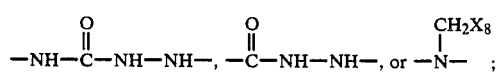

$A_5$ is

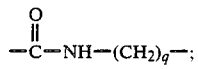

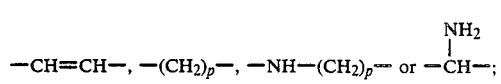

$A_6$ is

—CH=CH—, —(CH$_2$)$_p$—, —NH—(CH$_2$)$_p$— or —CH(NH$_2$)—;

p is 0, 1, 2, 3 or 4;
y is 2, 3 or 4;
q is 0 or 1; and
$X_8$ is hydrogen, carboxyl or carbamoyl;

wherein the term "substituted alkyl" refers to alkyl groups substituted with azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted amino" refers to a group having the formula —NX$_8$X$_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4,5,6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atom, groups.

2. A compound in accordance with claim 1 wherein R is

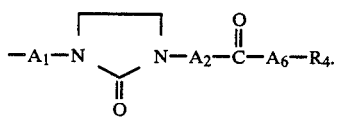

3. A compound in accordance with claim 1 wherein R is

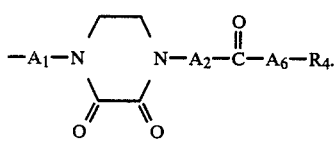

4. A compound in accordance with claim 1 wherein R is

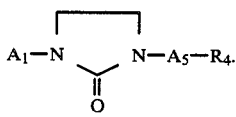

5. A compound in accordance with claim 1 wherein R is

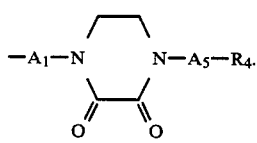

6. A compound in accordance with claim 1 wherein R is $-NH-A_3-R_4$.

7. A compound in accordance with claim 1 wherein R is

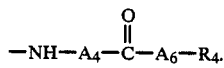

8. A compound in accordance with claim 1 wherein $R_4$ is

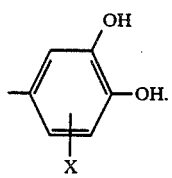

9. A compound in accordance with claim 1 wherein $R_4$ is

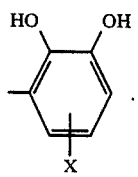

10. A compound in accordance with claim 8 wherein X is hydrogen.

11. A compound in accordance with claim 9 wherein X is hydrogen.

12. A compound in accordance with claim 1 wherein $R_1$ is

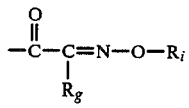

and $R_g$ is 2-amino-4-thiazolyl and $R_i$ is methyl, ethyl, carboxymethyl, 1-carboxy-1-methylethyl, 1-carboxy-1-ethyl, or

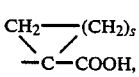

wherein s is 1, 2 or 3.

13. A compound in accordance with claim 1 wherein $R_1$ is

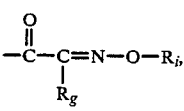

$R_g$ is 2-amino-4-thiazolyl and $R_i$ is carboxymethyl, 1-carboxy-1-methylethyl, 1-carboxy-1-ethyl, or

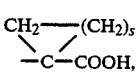

wherein s is 1, 2 or 3.

14. A compound in accordance with claim 2 wherein $R_1$ is

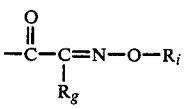

and $R_g$ is 2-amino-4-thiazolyl and $R_i$ is methyl, ethyl, carboxymethyl, 1-carboxy-1-methylethyl, 1-carboxy-1-ethyl or

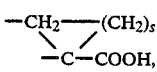

wherein s is 1, 2 or 3.

15. A compound in accordance with claim 2 wherein $R_1$ is

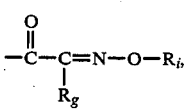

$R_g$ is 2-amino-4-thiazolyl and $R_i$ is carboxymethyl, 1-carboxy-1-methylethyl, 1-carboxy-1-ethyl or

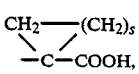

wherein s is 1, 2 or 3.

* * * * *